US012527887B2

(12) United States Patent
Mauzerall et al.

(10) Patent No.: US 12,527,887 B2
(45) Date of Patent: Jan. 20, 2026

(54) MOBILE STERILIZATION APPARATUS AND METHOD FOR USING THE SAME

(71) Applicant: SteriCUBE Surgical Systems, LLC, Grapevine, TX (US)

(72) Inventors: Michele Mauzerall, St. Petersburg, FL (US); Maryellen Keenan, St. Petersburg, FL (US)

(73) Assignee: STERICUBE SURGICAL SYSTEMS, LLC, Grapevine, TX (US)

( * ) Notice: Subject to any disclaimer, the term of this patent is extended or adjusted under 35 U.S.C. 154(b) by 0 days.

(21) Appl. No.: 16/442,234

(22) Filed: Jun. 14, 2019

(65) Prior Publication Data

US 2020/0030470 A1 Jan. 30, 2020

Related U.S. Application Data

(60) Provisional application No. 62/689,206, filed on Jun. 24, 2018.

(51) Int. Cl.
*A61L 2/07* (2006.01)

(52) U.S. Cl.
CPC ............ *A61L 2/07* (2013.01); *A61L 2202/24* (2013.01)

(58) Field of Classification Search
CPC ....................... A61L 2202/122; A61L 2202/24
See application file for complete search history.

(56) References Cited

U.S. PATENT DOCUMENTS 3,088,180 A 5/1963 Lauterbach
4,105,407 A 8/1978 Sanderson
4,228,914 A 10/1980 Sanderson
4,238,447 A 12/1980 Wolff
(Continued)

FOREIGN PATENT DOCUMENTS

DE 3202430 7/1983
DE 4125673 7/1992
(Continued)

OTHER PUBLICATIONS

CMS Clarifies Sterilization Guidelines for Ophthalmic ASCs—2015, Feb. 26, 2015, MLN Connects™ Provider eNews, https://www.aao.org/clinical-statement/cms-clarifies-sterilization-guidelines-ophthalmic-#:~:text=IUSS%20is%20the%20term%20currently%20accepted%20to% . . . (Accessed Aug. 5, 2021) (Year: 2015).*
(Continued)

*Primary Examiner* — Elizabeth A Robinson
*Assistant Examiner* — Changru Chen
(74) *Attorney, Agent, or Firm* — Knobbe, Martens, Olson & Bear, LLP

(57) ABSTRACT

A sterilization cabinet, comprising a top panel, at least two side panels, and a floor panel forming a part of a chamber of the sterilization cabinet; at least one door connected to at least one of the at least two side panels of the sterilization cabinet; a vent formed in at least one of the two side panels; at least one first filter covering the vent and a filter cover configured to hold the first filter against the vent; a drain positioned in the floor panel, wherein the floor panel has a slope configured to cause condensate within the chamber to flow into the drain and wherein the drain is the only outlet for the condensate along the floor panel; and a second filter covering the drain such that condensate flowing into the drain passes through the second filter.

24 Claims, 55 Drawing Sheets

(56) References Cited

U.S. PATENT DOCUMENTS

| | | | |
|---|---|---|---|
| 4,247,517 | A | 1/1981 | Sanderson et al. |
| 4,251,482 | A | 2/1981 | Sanderson et al. |
| 4,450,968 | A | 5/1984 | Muellner |
| 4,551,311 | A | 11/1985 | Lorenz |
| 4,617,178 | A | 10/1986 | Nichols |
| 4,626,971 | A | 12/1986 | Schultz |
| 4,643,303 | A | 2/1987 | Arp et al. |
| 4,670,227 | A | 6/1987 | Smith |
| 4,671,943 | A | 6/1987 | Wahlquist |
| 4,704,254 | A | 11/1987 | Nichols |
| 4,716,025 | A | 12/1987 | Nichols |
| 4,762,688 | A | 8/1988 | Berry |
| 4,783,321 | A | 11/1988 | Spence |
| 4,915,913 | A | 4/1990 | Williams et al. |
| 4,915,918 | A | 4/1990 | Nichols |
| 4,955,318 | A | 9/1990 | Melhorn et al. |
| 4,997,240 | A | 3/1991 | Schmalzl et al. |
| 5,019,345 | A | 5/1991 | Lorenz |
| 5,072,960 | A | 12/1991 | Sperko |
| 5,202,098 | A | 4/1993 | Nichols |
| 5,205,627 | A | 4/1993 | Davison et al. |
| 5,223,229 | A | 6/1993 | Brucker |
| 5,232,277 | A | 8/1993 | Cassady et al. |
| 5,281,400 | A | 1/1994 | Berry |
| 5,324,489 | A | 6/1994 | Nichols et al. |
| 5,346,075 | A | 9/1994 | Nichols et al. |
| 5,352,416 | A | 10/1994 | Wagner |
| 5,369,892 | A | 12/1994 | Dhaemers |
| 5,372,787 | A | 12/1994 | Ritter |
| 5,387,063 | A | 2/1995 | Napierkowski et al. |
| 5,415,846 | A | 5/1995 | Berry |
| 5,523,519 | A | 6/1996 | Weber et al. |
| 5,535,141 | A | 7/1996 | Lussi |
| 5,588,623 | A | 12/1996 | Leduc |
| 5,732,821 | A | 3/1998 | Stone et al. |
| 5,843,388 | A | 12/1998 | Arroyo et al. |
| 5,893,618 | A | 4/1999 | Lepage et al. |
| 5,923,432 | A | 7/1999 | Kral |
| 5,968,459 | A | 10/1999 | Nalepa et al. |
| 6,000,486 | A | 12/1999 | Romick et al. |
| 6,073,547 | A | 6/2000 | Westbrooks et al. |
| 6,164,738 | A | 12/2000 | Dane et al. |
| 6,218,796 | B1 | 4/2001 | Kozlowski |
| 6,319,479 | B1 | 11/2001 | Houston |
| 6,464,872 | B1 | 10/2002 | Honda |
| 6,589,477 | B1 | 7/2003 | Frieze et al. |
| 6,620,390 | B1 | 9/2003 | Wagner |
| 6,622,862 | B1 | 9/2003 | Corrado |
| 6,789,815 | B2 | 9/2004 | Moss et al. |
| 6,793,715 | B1 | 9/2004 | Sandberg |
| 6,867,393 | B1 | 3/2005 | Lewis |
| 6,926,874 | B2 | 8/2005 | Ongaro |
| 7,001,441 | B2 | 2/2006 | Bauer |
| 7,198,760 | B1 | 4/2007 | Wagner |
| 7,214,354 | B2 | 5/2007 | Ongaro |
| 7,544,915 | B2 | 6/2009 | Hu |
| 8,100,281 | B2 | 1/2012 | Sands et al. |
| 8,454,901 | B1 | 6/2013 | Snyder |
| 8,505,959 | B2 | 8/2013 | Darling |
| 9,439,992 | B2 | 9/2016 | Webb et al. |
| 9,616,143 | B2 | 4/2017 | Snyder et al. |
| 9,694,093 | B2 | 7/2017 | Snyder et al. |
| 9,724,439 | B2 | 8/2017 | Webb et al. |
| 9,808,545 | B2 | 11/2017 | Mauzerall et al. |
| 9,833,524 | B2 | 12/2017 | Mauzerall et al. |
| 10,086,100 | B1 | 10/2018 | Mauzerall et al. |
| 10,111,972 | B2 | 10/2018 | Mauzerall et al. |
| 10,166,305 | B2 | 1/2019 | Mauzerall et al. |
| 10,179,183 | B2 | 1/2019 | Snyder et al. |
| 10,406,252 | B2 | 9/2019 | Graves et al. |
| 10,413,628 | B2 | 9/2019 | Mauzerall et al. |
| 10,786,589 | B2 | 9/2020 | Mauzerall et al. |
| 10,828,383 | B2 | 11/2020 | Snyder et al. |
| 11,071,796 | B2 | 7/2021 | Mauzerall et al. |
| 11,110,187 | B2 | 9/2021 | Mauzerall et al. |
| 11,331,401 | B2 | 5/2022 | Mauzerall et al. |
| 11,654,206 | B2 | 5/2023 | Mauzerall et al. |
| 11,839,692 | B2 | 12/2023 | Mauzerall et al. |
| 11,890,389 | B2 | 2/2024 | Snyder et al. |
| 12,194,165 | B2 | 1/2025 | Mauzerall et al. |
| 12,257,360 | B2 | 3/2025 | Mauzerall et al. |
| 2003/0116636 | A1 | 6/2003 | Burkett et al. |
| 2004/0011689 | A1 | 1/2004 | Bauer |
| 2004/0096355 | A1 | 5/2004 | Ishibiki |
| 2004/0101456 | A1 | 5/2004 | Kuroshima et al. |
| 2004/0222116 | A1 | 11/2004 | Bauer |
| 2004/0227315 | A1 | 11/2004 | Van Landingham |
| 2005/0132924 | A1 | 6/2005 | Bothun et al. |
| 2005/0153052 | A1 | 7/2005 | Williams et al. |
| 2006/0032770 | A1 | 2/2006 | Orbay et al. |
| 2006/0108757 | A1 | 5/2006 | Brookmire et al. |
| 2006/0249313 | A1 | 11/2006 | Kamen et al. |
| 2007/0039294 | A1 | 2/2007 | Airey |
| 2007/0160494 | A1 | 7/2007 | Sands |
| 2008/0063580 | A1 | 3/2008 | Von Lersner |
| 2008/0087231 | A1 | 4/2008 | Gabriel et al. |
| 2008/0172295 | A1 | 7/2008 | Watson |
| 2010/0078905 | A1 | 4/2010 | Holtan |
| 2012/0061332 | A1 | 3/2012 | Kas |
| 2012/0082589 | A1 | 4/2012 | Ladison |
| 2012/0103482 | A1 | 5/2012 | Simmons |
| 2013/0236354 | A1 | 9/2013 | Taylor et al. |
| 2013/0272925 | A1 | 10/2013 | Ozdamar |
| 2013/0322004 | A1 | 12/2013 | Park |
| 2014/0030144 | A1 | 1/2014 | Krosney et al. |
| 2014/0079589 | A1 | 3/2014 | Landgrebe et al. |
| 2015/0023839 | A1 | 1/2015 | Snyder et al. |
| 2015/0078960 | A1 | 3/2015 | Krosney et al. |
| 2015/0107627 | A1 | 4/2015 | Snyder et al. |
| 2015/0209455 | A1 | 7/2015 | Turbett et al. |
| 2015/0209456 | A1 | 7/2015 | Turbett |
| 2015/0209462 | A1 | 7/2015 | Turbett et al. |
| 2015/0284018 | A1 | 10/2015 | Krosney |
| 2015/0314026 | A1 | 11/2015 | Mauzerall et al. |
| 2016/0008503 | A1 | 1/2016 | Webb et al. |
| 2016/0346415 | A1 | 12/2016 | Webb et al. |
| 2017/0080115 | A1 | 3/2017 | Mauzerall et al. |
| 2017/0128602 | A1 | 5/2017 | Snyder et al. |
| 2017/0189843 | A1 | 7/2017 | Turbett et al. |
| 2017/0274107 | A1 | 9/2017 | Snyder et al. |
| 2018/0015190 | A1 | 1/2018 | Turbett |
| 2018/0021464 | A1 | 1/2018 | Mauzerall et al. |
| 2018/0085480 | A1 | 3/2018 | Mauzerall et al. |
| 2018/0221803 | A1 | 8/2018 | Turbett et al. |
| 2019/0030198 | A1 | 1/2019 | Mauzerall et al. |
| 2019/0060494 | A1 | 2/2019 | Mauzerall et al. |
| 2019/0175774 | A1 | 6/2019 | Snyder et al. |
| 2020/0016289 | A1 | 1/2020 | Mauzerall et al. |
| 2021/0000993 | A1 | 1/2021 | Mauzerall et al. |
| 2021/0046202 | A1 | 2/2021 | Snyder et al. |
| 2021/0077640 | A1 | 3/2021 | Mauzerall et al. |
| 2021/0346536 | A1 | 11/2021 | Mauzerall et al. |
| 2022/0370672 | A1 | 11/2022 | Mauzerall et al. |
| 2023/0310669 | A1 | 10/2023 | Mauzerall et al. |
| 2024/0115750 | A1 | 4/2024 | Mauzerall et al. |
| 2024/0181103 | A1 | 6/2024 | Snyder et al. |
| 2024/0350686 | A1 | 10/2024 | Mauzerall |
| 2025/0135054 | A1 | 5/2025 | Mauzerall |

FOREIGN PATENT DOCUMENTS

| | | | | | |
|---|---|---|---|---|---|
| DE | 4125673 | C2 | | 9/1997 | |
| DE | 202008001263 | | | 7/2008 | |
| EP | 1566185 | | | 8/2005 | |
| EP | 1379816 | B1 | | 11/2005 | |
| EP | 1839683 | | | 10/2007 | |
| EP | 2179746 | A1 | | 4/2010 | |
| GB | 2333959 | A | * | 8/1999 | .............. A61L 2/07 |
| JP | S63-503363 | A | | 12/1988 | |
| JP | 05-061266 | U | | 8/1993 | |
| JP | 05-337081 | A | | 12/1993 | |
| JP | H07-505798 | | | 6/1995 | |
| JP | 10-27141 | A | | 1/1998 | |
| JP | 2001-234697 | A | | 8/2001 | |

(56) References Cited

FOREIGN PATENT DOCUMENTS

| | | | |
|---|---|---|---|
| JP | 2009-214736 | | 9/2009 |
| JP | 2001-112857 | | 8/2011 |
| JP | 4762432 | B2 | 8/2011 |
| JP | 2012-180733 | A | 9/2012 |
| JP | 2013-027707 | A | 2/2013 |
| KR | 10-0815569 | B1 | 3/2008 |
| WO | WO 1992/007588 | | 5/1992 |
| WO | WO 1999/049903 | | 10/1999 |
| WO | WO 2007/000639 | | 1/2007 |
| WO | WO 2010/128408 | | 11/2010 |
| WO | WO 2015/153084 | | 10/2015 |
| WO | WO 2016/032853 | | 6/2016 |
| WO | WO 2017/024260 | | 2/2017 |
| WO | WO 2019/023710 | | 1/2019 |
| WO | WO 2020/005844 | | 1/2020 |

OTHER PUBLICATIONS

"Food for Thought: Flash Sterilization", Aug. 2008, OR Manager, vol. 24 No. 8, https://www.ormanager.com/wp-content/uploads/pdfx/ORMVol24No8flashSterilization.pdf, Accessed Mar. 3, 2025 (Year: 2008).*
AMSCO Material Handling Accessories—Small Sterlizers and Aerators, 2 pages, Sep. 1, 2010, STERIS Corporation.
Getinge 4003 Floor Loading Carts Product Specification, 2 pages, Getinge Group, date unknown.
Operator Manual, AMSCO C Series Small Steam Sterilizers, 154 pages, May 7, 2012, STERIS Corporation.
Operator Manual, AMSCO Century Medium Steam Sterlizer, 186 pages, Jul. 16, 2007, STERIS Corporation.
Operator Manual, AMSCO Century Medium Steam Sterlizers, 135 pages, Dec. 16, 2005, STERIS Corporation.
SCORES 510k Summary Pursuant to 21 CFR 807.92, 6 pages, Jul. 26, 2012, AmMed Surgical Equipment, LLC/FDA.
SCORES Cabinet Landing Page, 1 page AmMed Surgical Equipment, LLC, date unknown.
Scores FAQ, 2 pages, AmMed Surgical Equipment, LLC, date unknown.
SCORES Instructions for Use, 22 pages, AmMed Surgical Equipment, LLC, , date unknown.
SCORES Savings Analysis, 2 pages, AmMed Surgical Equipment, LLC, date unknown.
SCORES Testing Summary, 1 page, AmMed Surgical Equipment, LLC, date unknown.
SCORES Unit Images in Open Configurations and Landing Page Information About the SCORES Unit, 2 pages, AmMed Surgical Equipment, LLC, date unknown.
The Amsco Loading Car and Transfer Carriage—III data sheet, 2 pages, Jul. 10, 1998, STERIS Corporation.
The SCORES Advantage: Time Energy & Cost Savings, 1 page, AmMed Surgical Equipment, LLC, date unknown.
The Steris Amsco Sterilization Container System User's Guide, ©2003-2006.
Steris Loading Equipment for Amsco Evolution and Evolution—L Steam Sterilizers—North America data sheet, ©2011.
Prophy-Mate. Datasheet (online). NSK, 2002, Retrieved from the internet: URL:http://www.nsktech.com .au/uploads/704 72/ufiles/Prophy _Mate .pdf, 2 pages, [retrieved on Aug. 28, 2019].
Wagner Gmbh: "www.wagner-steriset.de", Apr. 5, 2013, XP055413087, retrieved from the Internet: URL:http://www.wanger-steriset.de/fileadmin/pdf/Steriset_PCD034. pdf [retrieved on Oct. 5, 2017]. (PDF dated Sep. 28, 2016).
WagnerGmbh: "The 134 °drain (standard)", Apr. 11, 2004, XP055413196, retrieved from the Internet: URL:http://www.wagner-steriset.de/en/the-steriset-system/sterisets-concept/the-134-c-drain- standard/ [retrieved on Oct. 6, 2017]. (PDF dated Nov. 15, 2017).
Build a Do-It-Yourself air Purifer for About $40, Michigan Medicine, Jun. 28, 2011. https://www.youtube.com/watch?v=kH5APw_SLUU.
Comprehensive guide to steam sterilization and sterility assurance in health care facilities, American National Standard, ANSI/AAMI ST79:2017/(R)2022 & 2020 Amendments A1, A2, A3, A4 (Consolidated Text).
SteriTite Rigid Sterilization Container Instructions for Use / Case Medical, CaseMedical, Feb. 10, 2011. https://www.youtube.com/watch?v=petDUyyPmA4.
Anonym: 11 Druckgesteuert—waschbar—zerlegbar 11, Wagner-Steriset, Retrieved from the Internet: URL:http://www.wagner-steriset.de/fileadmin/pdf/SterisetPCD034.pdf, Apr. 5, 2013 [retrieved on Oct. 5, 2017].
Anonym: 11 The 134 ~C drain (standard) 11, Wagner Gmbh, Retrieved from the Internet: URL:http://www.wagner-steriset.de/en/the-steriset-system/sterisets-concept/the-134-c-drain-standard/, Apr. 11, 2004 [retrieved on Oct, 6, 2017].
Wagner Sterilsystem, The SteriSet System, pp. 6-7, May 6, 2005, https://web.archive.org/ web/20050506101217/http://www.wagner-steriset.de/html/mOI E23.htm.
Wagner Sterilsysteme, "Or Filter After All?", pp. 4-5, Aug. 25, 2005, https://web.archive.org/web/20110112052317/http://www.wagner-steriset.de/images/PDFs/Container/Steri Set_Ru ndfi Iter 2003.pdf.
Wagner Sterilsysteme, The SteriSet System, pp. 1-3, Aug. 25, 2005, https://web.archive.org/web/20050825213235/http://www.wagner-steriset.de/html/mOI E21.htm.

* cited by examiner

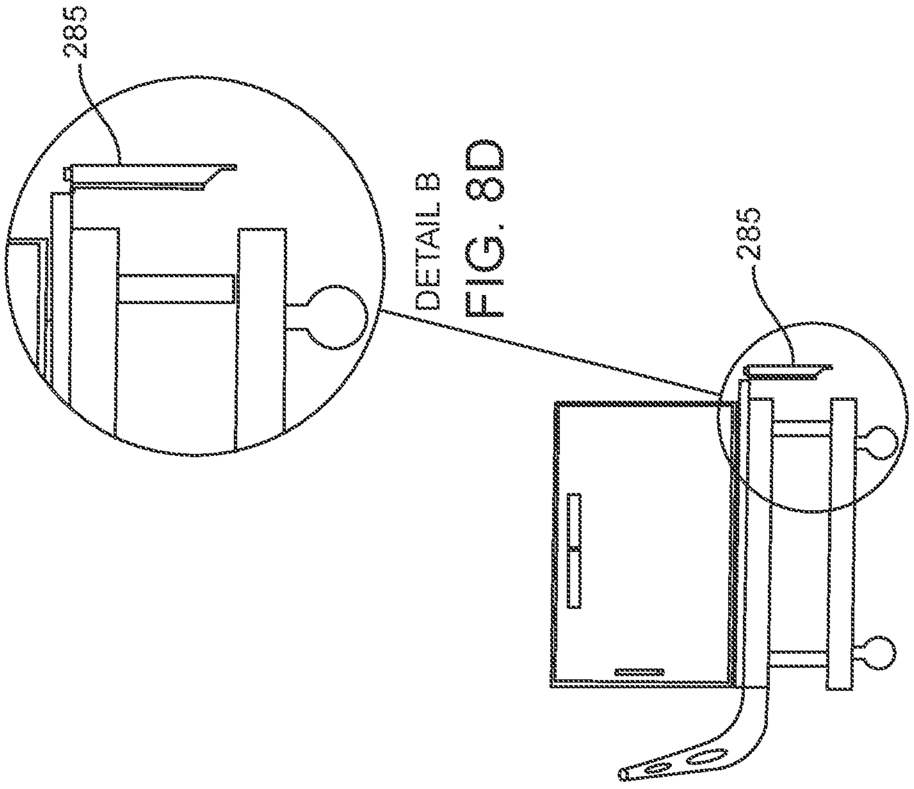
FIG. 8D
FIG. 8C
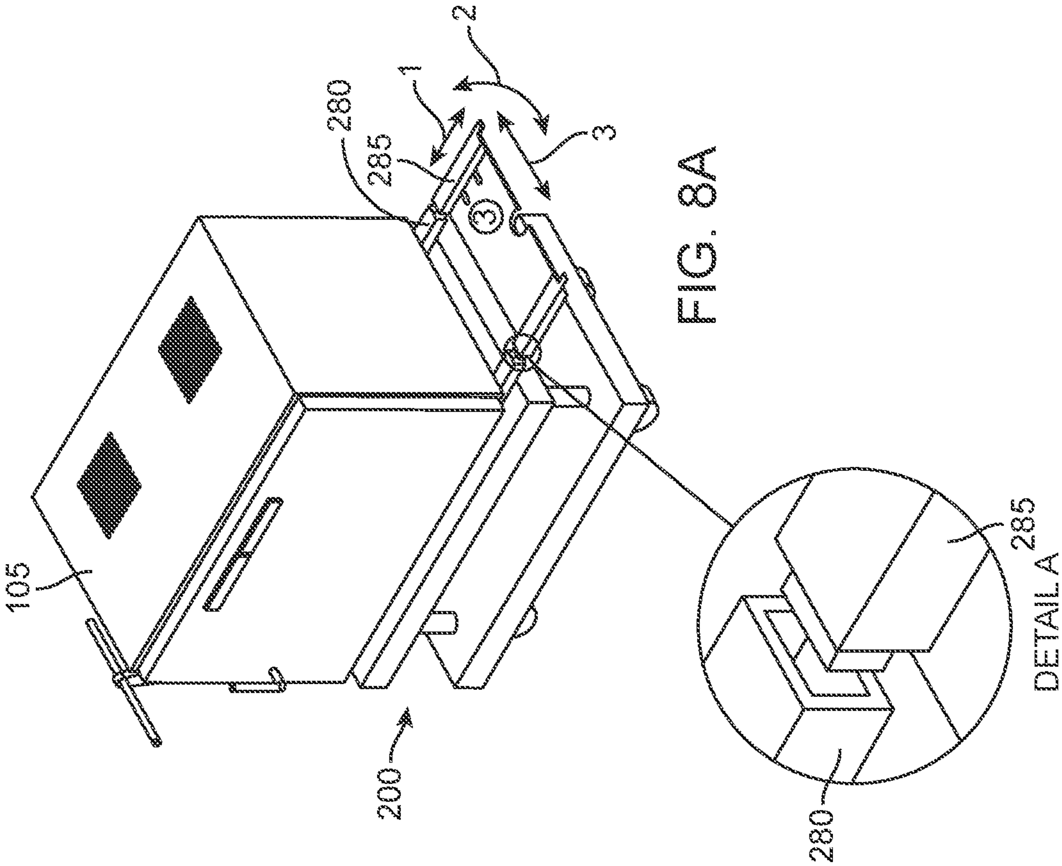
FIG. 8A
FIG. 8B

MOBILE STERILIZATION APPARATUS AND METHOD FOR USING THE SAME

CROSS-REFERENCE TO RELATED APPLICATIONS

This application claims benefit of priority to U.S. Provisional Patent Application No. 62/689,206, filed Jun. 24, 2018, the content of which is incorporated herein by reference in its entirety.

FIELD OF THE TECHNOLOGY

This invention relates to medical devices and procedures in general, and more particularly to sterilization apparatus and procedures for sterilizing medical instruments and/or devices and maintaining sterility until their intended use.

BACKGROUND

Many medical procedures require the use of sterile instruments and/or devices to perform the medical procedure. Providing sterile instruments and/or devices for these medical procedures is currently a time-consuming and expensive undertaking that requires, among other things, many man-hours, specialized equipment, etc.

In the past, hospitals (and/or other surgical facilities, e.g., surgicenters, etc.) have used an instrument tray sterilization system, in which trays containing the required instruments and/or devices for a given procedure are wrapped with a specially manufactured disposable wrap. The wrapped trays are then autoclaved and processed to the manufacturers' recommendations. The trays are then removed from the autoclave, allowed to cool, and then stored until the contents are needed for a procedure. Prior to the use of the instruments and/or devices, additional man-hours are expended to inspect the wraps so as to ensure that there is no damage that might lead to the contents being deemed non-sterile.

In part to address some of the shortcomings discussed above, mobile sterilization cabinets have been introduced. FIGS. 1-3 show an exemplary prior art mobile sterilization cabinet 5. Sterilization cabinet 5 typically comprises a rectangular-shaped interior chamber 10 (FIG. 2) surrounded by a cabinet bottom 25, cabinet side walls 26, a cabinet back wall 27 and a cabinet top 40. Cabinet 5 may further comprise one or more doors 30 to selectively open up or close off interior chamber 10 of cabinet 5. See, for example, FIG. 2 which shows a cabinet 5 with one door 30 in the open position, and FIG. 3 which shows cabinet 5 with two doors 30 in the closed position. Cabinet 5 may further comprise a gasket (not shown) at the interface of the door(s) and frame of cabinet 5 for sealing cabinet 5 when the door(s) is (are) closed.

Interior chamber 10 of cabinet 5 is preferably also equipped with shelves 45 for supporting surgical trays within chamber 10.

Furthermore, cabinet 5 comprises one or more vents 35 formed in the cabinet top 40 and/or cabinet bottom 25. Vent 35 is covered by a filter 50, and a filter cover 55 holds filter 50 in place against vent 35.

In order to move cabinet 5 into an autoclave or into an operating room or storage room, cabinet 5 comprises wheels 20 mounted directly to cabinet bottom 25. In use, medical instruments and/or instrument trays are positioned on shelves 45, and the shelves are loaded into interior chamber 10 of cabinet 5. Alternatively, shelves 45 may be loaded into cabinet 5 and then the medical instruments and/or instrument trays positioned on shelves 45. Then the entire cabinet 5 is wheeled into an autoclave which is subsequently activated. The hot air and steam generated by the autoclave is able to penetrate into interior chamber 10 of cabinet 5 by way of vents 35, thereby sterilizing cabinet 5 and its contents. At the end of the autoclaving cycle, cabinet 5 is removed from the autoclave, allowed to cool, and then moved to a storage space or directly to an operating room or other space for use in connection with a medical procedure. Sterilized cabinet 5 is kept closed until such time that its contents are required for a medical procedure. So long as cabinet 5 is kept closed, the contents will remain sterile, inasmuch as filters 50 prevent the passage of contaminants through vents 35 into the interior of the cabinet.

While the introduction of mobile sterilization cabinets has allowed for significant savings and efficiencies in hospital sterilization procedures, several shortcomings remain. For example, existing prior art cabinets can be difficult to maneuver into and out of an autoclave and can be difficult to maneuver around a hospital (e.g., to a storage area or an operating room).

Further, existing cabinets 5 can be difficult to store in increasingly crowded hospitals where space is frequently at a premium. In addition, opening existing cabinets at the desired time can significantly expand the footprint of the existing cabinets, inasmuch as space must be allocated to accommodate the swing radius of the door(s).

In addition, existing cabinets can sometimes retain water in the bottom of the cabinet at the end of the autoclave cycle. This is undesirable for several reasons, one of which is that the water can serve as a conduit through which contaminants can be "pulled" (e.g., by a wicking action, through a filter 50 in cabinet bottom 25 and into interior chamber 10).

It can also be difficult for medical personnel to visually assess the current status of existing cabinets or their contents. For example, it is difficult for personnel to know whether an existing cabinet that has been autoclaved is still too hot to handle or whether it has cooled to the point where it may be safely handled. Similarly, it can be difficult for personnel to visually ascertain or verify the status and/or inventory of the contents inside of an existing cabinet without having to open the cabinet and thereby violate the sterile field.

Additional shortcomings of existing cabinets include cumbersome interior shelving, an inability to sufficiently isolate smaller areas within the cabinet, difficulty in accessing and changing filters, etc.

There is also need for equipment that meets the increasing demand for "immediate use sterilization" and/or "flash" sterilization. Immediate-use steam sterilization ("IUSS"), previously referred to as flash sterilization, is often discouraged given that the process was complex and created more opportunities for compromised sterility, required a facility to consistently follow all the necessary steps each time to ensure the sterility of the instruments to the point of use with little room for error, and still the process of IUSS resulted in higher infection rates. Improper techniques during sterilization of medical items resulted in the use of contaminated instruments in surgery. This can result in serious consequences including, but not limited to, surgical site infections (SSI).

The serious consequence of an SSI is the greatest concern of improper use of immediate-use steam sterilization. The risks of SSI include an increased mortality rate. Estimates place SSI's as affecting 2 percent to 5 percent of all patients undergoing surgery and patients with an SSI are believed to have a 3 percent mortality rate. Aside from the increased mortality rate, SSIs can increase a patient's hospital stay significantly. As a result, SSI's not only account for increased patient harm but also an increase in healthcare costs.

Immediate-use steam sterilization can be a safe and effective process if used correctly and if the procedures are simplified. However, the standard of care does not recommend immediate use sterilization as a matter of convenience. Instead, given the complexity, the present recommendation is to reduce the reliance and use of the immediate use sterilization process. If the process of immediate use steam sterilization were as safe and effective as the general process of traditional terminal sterilization (during which instruments are processed on a full length cycle in accordance with their manufacturer's Instructions for Use), then healthcare would benefit as a whole as hospitals could increase their throughput with shorter sterilization cycles and patients could get much needed surgical procedures without painfully waiting for months to be scheduled.

In view of the above, there is a need for a mobile sterilization apparatus and improved methods of sterilizing using this technology to safely and effectively sterilize medical items (such as medical instruments, implants and/or devices). Furthermore, the improved apparatus should allow for both immediate use sterilization, where the medical item is not stored but used immediately after the sterilization process, and traditional terminal sterilization where the medical items are sterilized and then stored until delivered to a location where a medical procedure will be performed.

SUMMARY

The present invention provides new and improved methods for confirming the integrity of one or more seals on a mobile sterilization apparatus and devices for confirming the integrity. These methods and devices allow for sterilizing medical instruments and devices, for storing the sterilized medical instruments and devices in a sterile condition until use, and then delivering the sterilized medical instruments and devices to a location where a medical procedure will be performed.

The present invention includes methods of sterilizing medical instruments using immediate use sterilization, where the sterilization agent can comprise a steam or any other agent that is delivered into a sterilization container to sterilize the medical items placed therein, and then evacuated from the sterilization container. For example, the agent can comprise hydrodgen peroxide, paracidic acid, ethylene oxide (EtO), oxone, heat, etc. In one example the method includes positioning at least one medical instrument within an enclosed sterilization area of a sterilization cabinet, the sterilization cabinet includes a plurality of walls and a floor, an opening to permit accessing to the enclosed sterilization area, a door configured to close the sterilization cabinet by forming a seal that closes the opening, at least one vent in the sterilization cabinet, a filter covering the vent on an exterior of the sterilization cabinet; closing door on the sterilization cabinet to seal the enclosed sterilization area; positioning the sterilization cabinet in an autoclave; initiating a sterilization cycle to sterilize the medical instruments within the sterilization cabinet by subjecting the sterilization cabinet to least one steam application within the autoclave; drawing a vacuum within the enclosed sterilization area to pull condensate away from the medical instruments wherein any condensate remaining within the enclosed sterilization area is driven by gravity to a region of the cabinet that prevents flowing of the condensate out of the opening when the door is opened; ending the sterilization cycle; and relocating the cabinet from the autoclave to a staging area such that the medical instruments are available for immediate use.

The method can further include positioning at least one tamper evident lock on the door after closing the door. A variation of the method can include relocating the cabinet from the autoclave to the staging area prior to a drying cycle of the autoclave.

In another variation, the method can include a cabinet wherein the floor is angled towards the door and the door comprises a fluid trap to collect any condensate which prevents flowing of the condensate out of the opening when the door is opened.

The method of relocating the cabinet from the autoclave can occur without initiating a dry cycle of the autoclave.

A variation of the method includes relocating the cabinet from the autoclave occurs after initiating a shortened dry cycle of the autoclave.

Another variation of the method includes a floor that is angled to collect the condensate away from the opening to prevent flowing of the condensate out of the opening when the door is opened.

A variation of the method includes use of a cabinet where a floor of the sterilization cabinet is pitched causing any condensate remaining within the enclosed sterilization area to be driven by gravity to a lowest portion the floor. Such a method can further include a drain in the cabinet and where the floor is pitched toward the drain such that condensate is directed by gravity towards the drain, and wherein the drain is covered by a second filter. Another variation of the method can further comprise positioning a condensate filter in fluid communication with the drain that prevents condensate from passing through the filter or through the drain.

In another variation of the method the condensate filter is positioned on an exterior of the sterilization cabinet. The condensate filter can also comprise a plug in the drain that prevents condensation from escaping after ending the sterilization cycle. Alternatively, the condensate filter can comprise a thermostatic controlled apparatus that opens to release condensation from the drain during an increased temperature of the sterilization cycle and closes the drain when a temperature within the sterilization cabinet lowers after the sterilization cycle.

Another variation of the method includes placement of a material at the bottom of the cabinet that behaves like a sponge allowing moisture to be wicked away from the interior of the cabinet and the material can retain the moisture within the one or more layer of its material.

Another variation of the method includes providing a sterilization cabinet having a chamber with a plurality of walls surrounding the chamber, where the plurality of walls form an opening for placement of the medical item within the chamber, the sterilization cabinet is configured to use gravity to direct a condensate that is generated during a sterilization process along a floor of the sterilization cabinet to a lowest point in the cabinet; closing a door to the sterilization cabinet when the medical items is within the enclosed chamber to seal the enclosed chamber; positioning the sterilization cabinet within a sterilization unit; initiating the sterilization unit to perform a shortened sterilization cycle; applying a vacuum cycle to the sterilization cabinet to pull air and condensate out of the sterilization cabinet; stopping the sterilization cycle and removing the sterilization cabinet from the sterilization unit; and delivering the medical item to a surgical area without storing the medical item.

Another variation includes a method of performing an immediate use sterilization for surgical items. For example, such a method can include providing a cabinet comprising: a plurality of walls surrounding an interior chamber, the plurality of walls defining an opening for positioning the surgical item into the interior chamber; a pitched floor that directs condensation to a lowest point in the pitched floor; a door configured to close the opening to seal the cabinet; a plurality of vented sections located on at least two walls such that at least a top of the cabinet and a wall of the cabinet are vented, where each vented section comprises a plurality of openings while retaining structural integrity of the panel; a plurality of filters, each filter covering at least one of the plurality of vented sections, and a drain formed in a lowest point of the pitched floor panel, such that any condensate is directed by gravity towards the drain, and wherein the drain is covered by a second filter; closing the door of the cabinet to seal the cabinet once the surgical items are introduced within the cabinet; placing the cabinet into an autoclave; introducing an agent into the cabinet during a sterilization cycle; initiating a drying cycle by pulling a vacuum within the cabinet immediately following the sterilization cycle, wherein the drain, pitched floor panel and the plurality of vented sections allows for elimination of all moisture from the interior sterilization area within a maximum of 5 minutes of a start of the drying cycle.

Yet another variation of a method can include providing a sterilization cabinet comprising: a plurality of panels, wherein at least one of the plurality of panels is a floor panel, a door configured to seal the sterilization cabinet, a vent defined on at least one of the plurality of panels and a first filter covering the vent, and a drain defined on the floor panel, wherein the floor panel is pitched toward the drain such that any condensate is directed by gravity towards the drain, and wherein the drain is covered by a second filter; closing the door of the sterilization cabinet to seal the sterilization cabinet once the medical instruments are introduced within the sterilization cabinet; introducing the sterilization cabinet into an autoclave; sterilizing the medical instruments within the sterilization cabinet using the autoclave at an immediate use sterilization temperature and an immediate use sterilization pressure for between about 3 minutes and 10 minutes.

A variation of the method includes an immediate use sterilization temperature between about 130 degrees celsius and about 190 degrees celsius and an immediate use sterilization pressure is between about 20 psi and about 40 psi.

In another variation, the method includes providing a sterilization cabinet comprising: a plurality of panels, wherein at least one of the plurality of panels is a floor panel, a door configured to seal the sterilization cabinet, a vent defined on at least one of the plurality of panels and a first filter covering the vent, and a drain defined on the floor panel, wherein the floor panel is pitched toward the drain such that any condensate is directed by gravity towards the drain, and wherein the drain is covered by a second filter; closing the door of the sterilization cabinet to seal the sterilization cabinet once the medical instruments are introduced within the sterilization cabinet; introducing the sterilization cabinet into an autoclave; sterilizing the medical instruments within the sterilization cabinet by subjecting the sterilization cabinet to least one steam sterilization cycle within the autoclave; and drying the medical instruments within the sterilization cabinet by pulling air and condensate out of the autoclave under vacuum.

Yet another method can include providing a sterilization cabinet comprising: a plurality of panels, wherein at least one of the plurality of panels is a floor panel, a door configured to seal the sterilization cabinet, a vent defined on at least one of the plurality of panels and a first filter covering the vent, and a drain defined on the floor panel, wherein the floor panel is pitched toward the drain such that any condensate is directed by gravity towards the drain, and wherein the drain is covered by a second filter; placing the sterilization cabinet on a transfer cart, the transfer cart comprising a pair of transfer cart tracks and adaptor railings; introducing the medical instruments into the sterilization cabinet; closing the door of the sterilization cabinet to seal the sterilization cabinet once the medical instruments are introduced within the sterilization cabinet; sliding the sterilization cabinet from the transfer cart into the autoclave over the pair of transfer cart tracks and the adaptor railings, wherein the adaptor railings are configured to connect the pair of transfer cart tracks with an interior of the autoclave; sterilizing the medical instruments within the sterilization cabinet by subjecting the sterilization cabinet to least one steam sterilization cycle within the autoclave; and drying the medical instruments within the sterilization cabinet by pulling air and condensate out of the autoclave under vacuum.

The following applications are incorporated by reference herein: Ser. No. 14/644,094 now U.S. Pat. No. 9,808,545; Ser. No. 14/861,620 now U.S. Pat. No. 9,439,992; Ser. No. 15/369,713 now U.S. Pat. No. 9,833,524; Ser. No. 15/233,384 now U.S. Pat. No. 9,724,439; Ser. No. 15/831,144 Publication No. US20180085480; Ser. No. 15/716,329 Publication No. US20180021464; Ser. No. 13/944,875 now U.S. Pat. No. 9,616,143; Ser. No. 15/411,361 now U.S. Pat. No. 9,694,093; Ser. No. 15/608,739 Publication No. US20170274107; Ser. No. 12/387,673 now U.S. Pat. No. 8,454,901; Ser. No. 14/680,333 Publication No. US20150284018; and Ser. No. Ser. No. 15/663,230 filed on Jul. 28, 2017

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 4-6, 7A-7D and 8A-8D are schematic views showing a novel mobile sterilization system comprising a novel sterilization cabinet and a novel transfer cart;

DETAILED DESCRIPTION

The present invention provides a new and improved mobile sterilization apparatus and method for sterilizing medical instruments and devices, for storing the sterilized medical instruments and devices in a sterile condition until use, and then delivering the sterilized medical instruments and devices to a location where a medical procedure will be performed.

Figure 1:
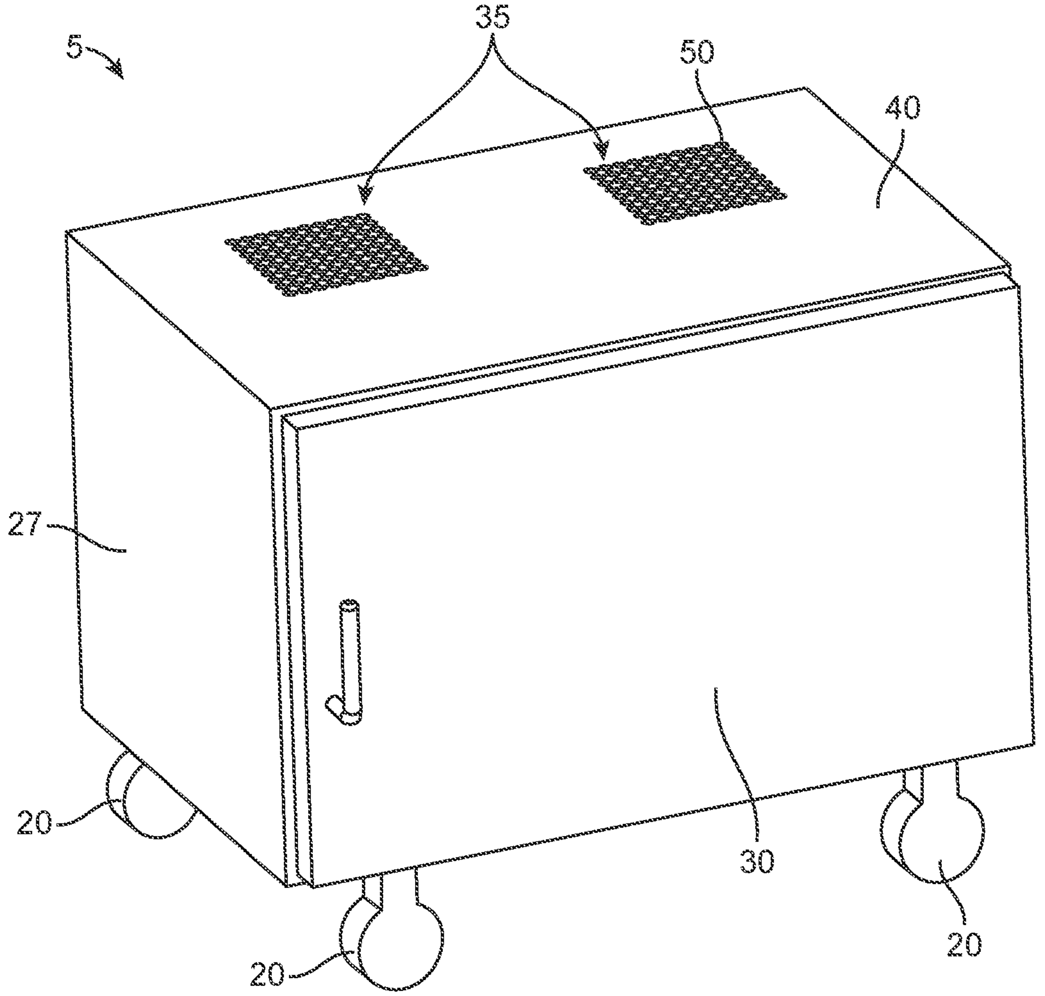
FIG. 1 (PRIOR ART)
FIGS. 1-3 are schematic views showing a prior art mobile sterilization cabinet.
Figure 2:
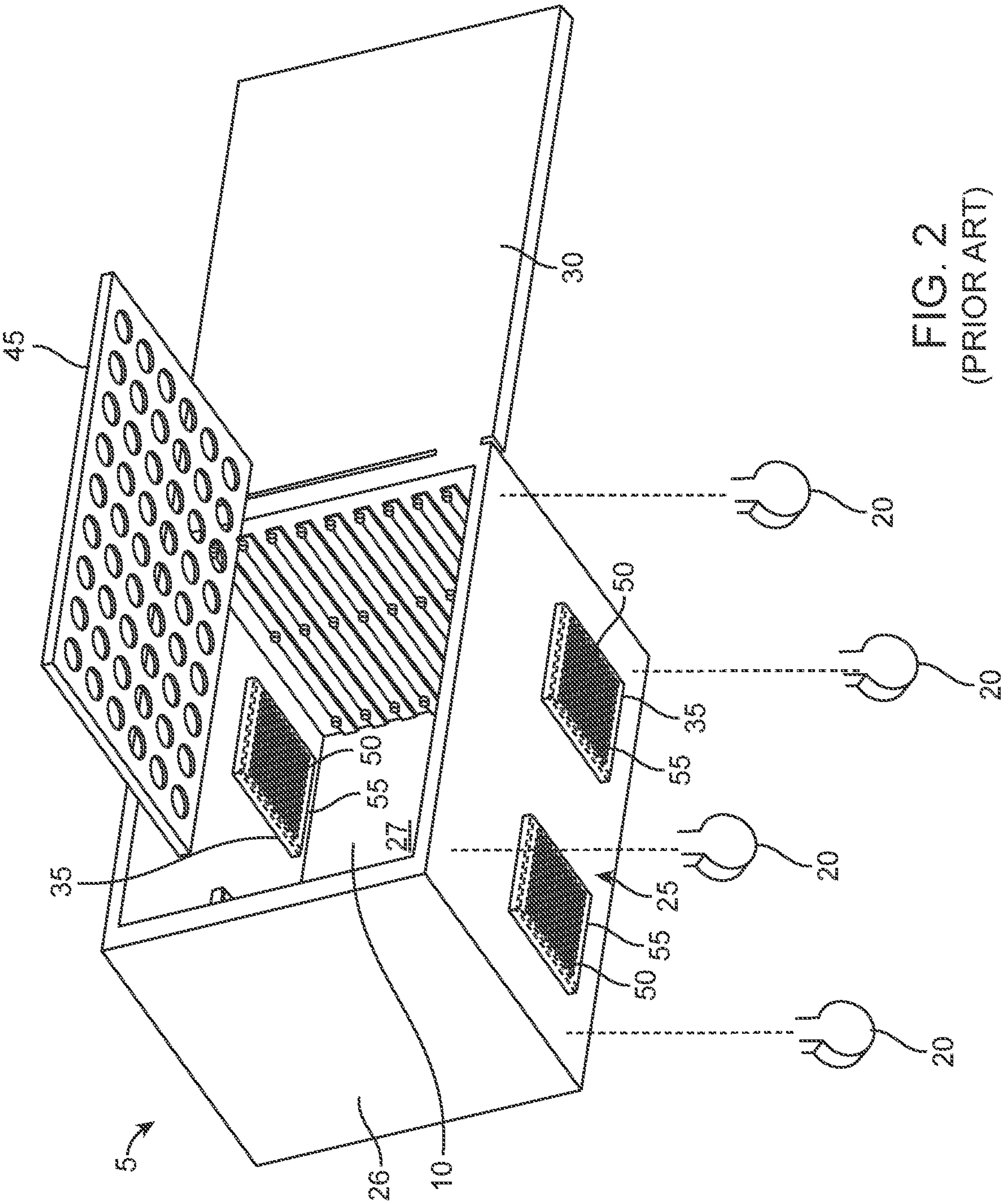
FIG. 2 (PRIOR ART)
Figure 3:
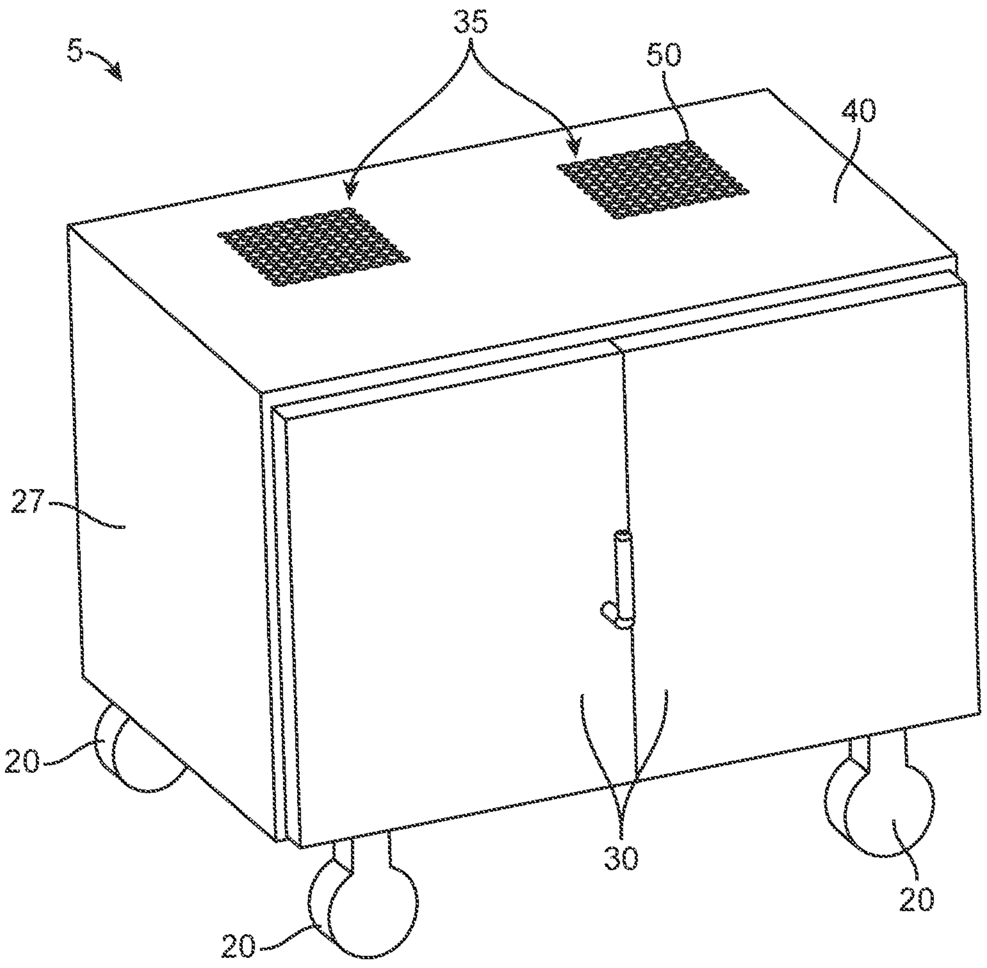
FIG. 3 (PRIOR ART)
Figure 4:
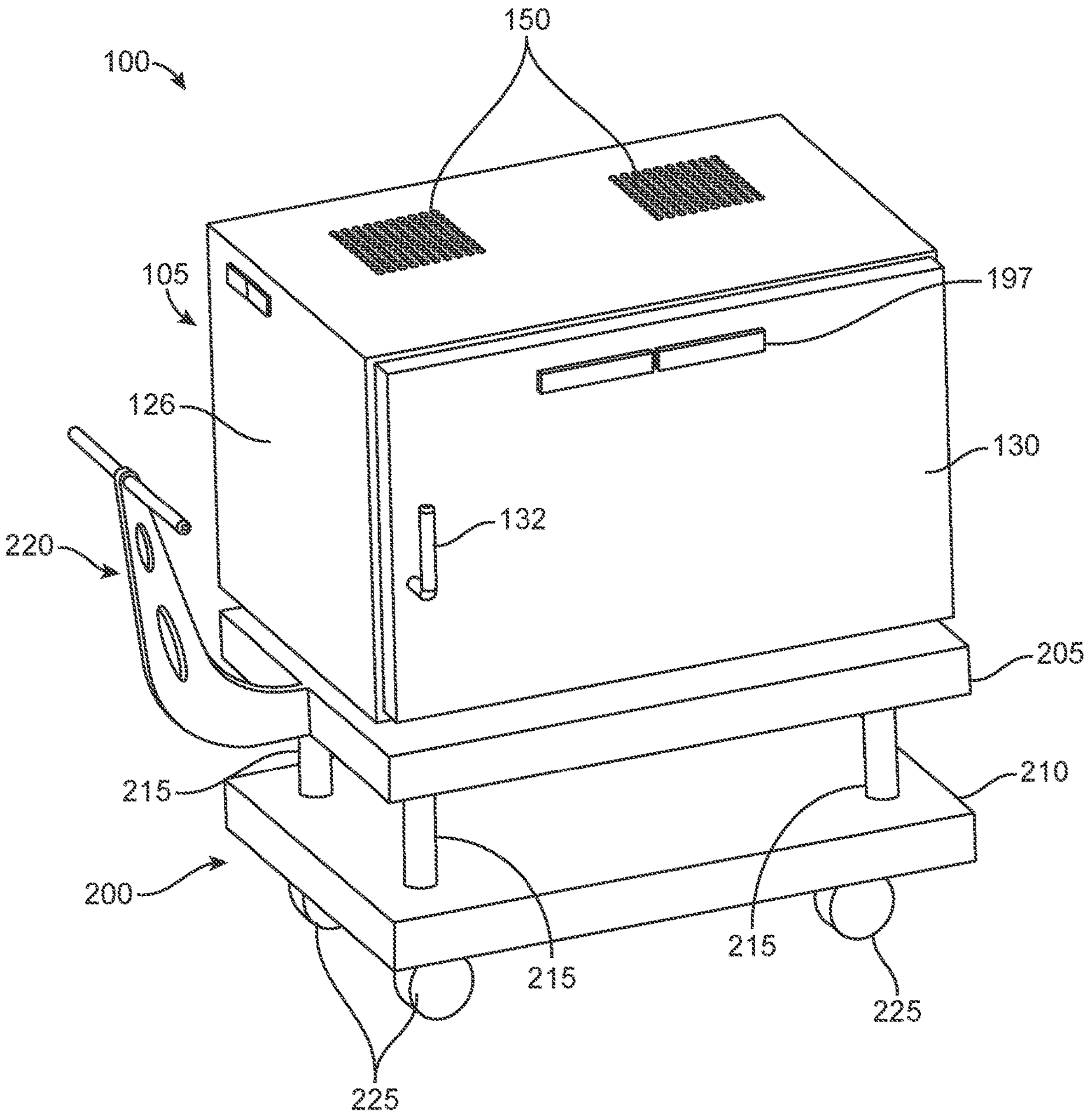

Looking now at FIG. 4, there is shown a novel mobile sterilization system 100 comprising a novel sterilization cabinet 105 and a novel transfer cart 200.

Sterilization cabinet 105 typically comprises a rectangular-shaped interior chamber 110 (FIG. 13) surrounded by a cabinet bottom 125, cabinet side walls 126, a cabinet back wall 127 and a cabinet top 140. Cabinet 105 may further comprise one or more doors 130 to selectively open up or close off interior chamber 110 novel mobile sterilization system 100 of cabinet 105. Cabinet 105 may further comprise a gasket (not shown) at the interface of the door(s) and frame of cabinet 105 for sealing cabinet 105 when the door(s) are closed.

Interior chamber 110 of cabinet 105 is preferably also equipped with shelves 145 (FIG. 23) for supporting surgical trays or instruments, etc. within chamber 110.

Furthermore, cabinet 105 comprises one or more vents 135 formed in at least one of the cabinet side walls 126, cabinet back wall 127, the cabinet top 140 and cabinet bottom 125. Vent 135 is covered by a filter 150, and a filter cover 155 (FIG. 23) holds filter 150 in place over vent 135. Further details of sterilization cabinet 105 (e.g., improvements to doors 130, filters 150, shelves 145, etc.) will be discussed in further detail below.

In order to move sterilization cabinet 105 along a surface (e.g., along a floor, along transfer cart 200, etc.), sterilization cabinet 105 comprises a plurality of casters or wheels 160 (generally shown in the figures in schematic form). In one preferred form of the invention, casters or wheels 160 are mounted to cabinet bottom 125, e.g., via a wheel or caster bracket (see below) of the sort well known in the art. Note that casters or wheels 160 are not visible in a number of the figures due to the angle of view of those figures. However, wheels or casters 160 can be clearly seen in FIGS. 7C, 13, 22A, 22B, 23, 24, 25A, 27, 29D, 30D, 36, 37, 39, 41, 43 and 44.

While sterilization cabinet 105 can be moved along a floor via its casters or wheels 160, in many situations it can be desirable to move sterilization cabinet 105 on transfer cart 200, e.g., into an autoclave or into an operating room or storage room.

More particularly, transfer cart 200 provides a platform upon which sterilization cabinet 105 may be positioned for transport between locations. By way of example but not limitation, transfer cart 200 may be used to move sterilization cabinet 105 from one part of a facility to another (e.g., a sterile processing department or an autoclave to an operating room). In addition, and again by way of example but not limitation, transfer cart 200 may be used to transfer sterilization cabinet 105 into and out of storage, and/or to move sterilization cabinet 105 into and out of an autoclave, and/or to move sterilization cabinet 105 between facilities or hospital rooms.

Transfer cart 200 generally comprises an upper platform 205 (FIG. 4) for receiving sterilization cabinet 105, a lower platform 210 to which a mechanism (e.g., wheels) for moving the transfer cart between locations is mounted. Vertical risers 215 extend between upper platform 205 and lower platform 210. Transfer cart 200 preferably also comprises a handle 220 for maneuvering transfer cart 200 between locations.

Figure 5:
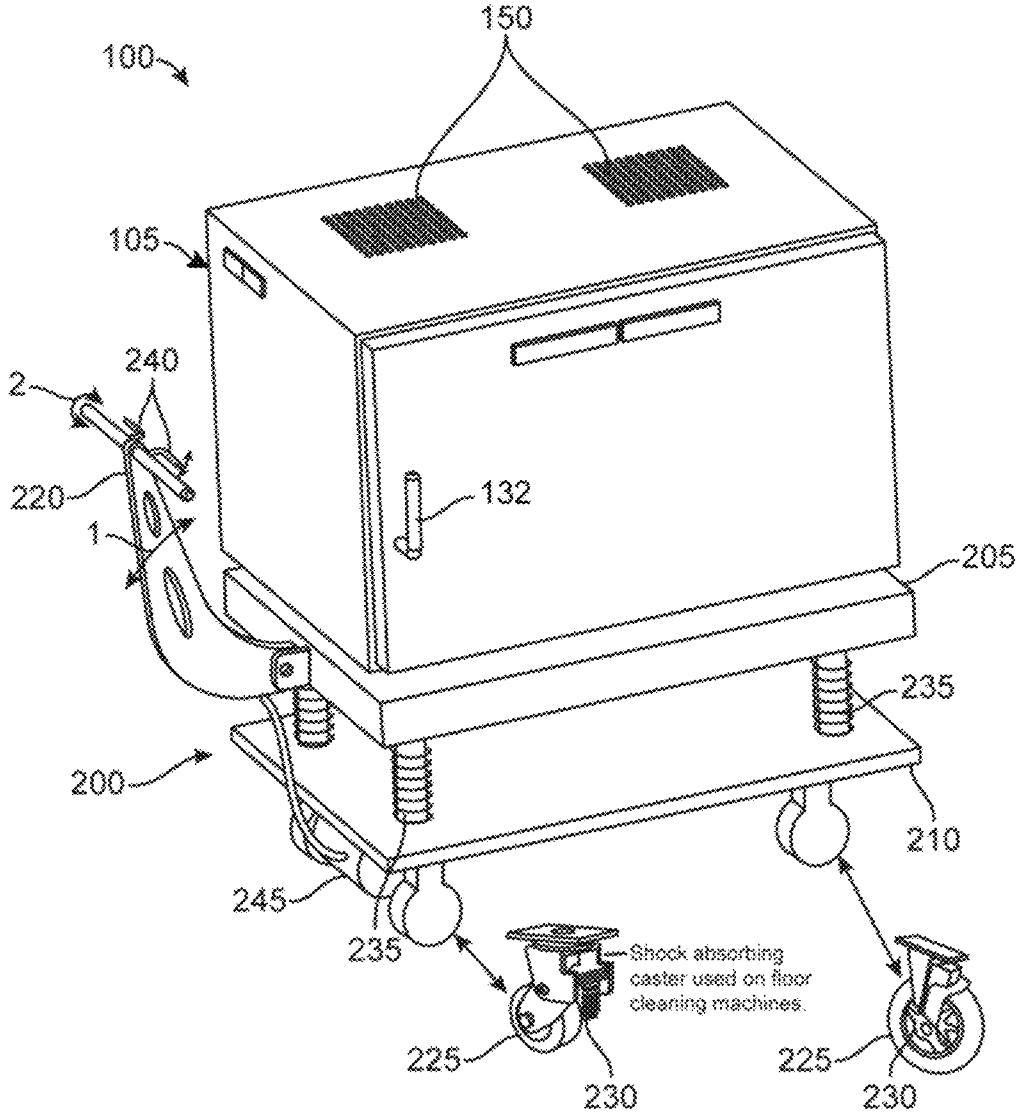

Looking now at FIGS. 4 and 5, transfer cart 200 comprises swiveling casters 225 for moving transfer cart 200 between locations. Casters 225 may be adjusted between a swiveling condition and a non-swiveling condition by way of easily-accessed, foot-operated pedal adjustment(s) on casters 225, or by way of adjustments performed from a handle 220. In other words, a user is able to adjust casters 225 from a first configuration wherein the casters are swivelable and a second configuration wherein the casters 225 are locked against swiveling. This feature allows a user to exercise additional control over transfer cart 200 when it is being moved between locations. Casters 225 can also be anti-static as an added safety feature.

Preferably, transfer cart 200 may be provided with a compliant shock-absorbing suspension system that enables a smoother "ride" over varying terrain and inclines as well as during shipping with, and without, instrument trays (loaded with medical instrumentation or other contents) being positioned in sterilization cabinet 105.

By way of example but not limitation, mobile sterilization system 100 may be transported fully loaded by remotely-located sterile processing companies to and from medical or other facilities that are sometimes hundreds of miles away from a remotely-located sterile processing facility. The shock-absorbing suspension system allows for improved safety and security of the loaded medical instrument trays to limit possible damage and/or displacement caused during transportation.

As shown in FIG. 5, a shock-absorbing suspension system may comprise shock-absorbing suspension springs 230 positioned on casters 225 and/or resilient springs 235 mounted between upper platform 205 and lower platform 210 in place of vertical risers 215.

Alternatively, vertical risers 215 may be formed in a telescopic configuration and resilient springs 235 may be disposed around and/or inside telescopic vertical risers 215. Resilient springs 235 are set so as to bias upper platform 205 and lower platform 210 away from one another, so as to provide shock absorption functionality for upper platform 205 (and sterilization cabinet 105) when casters 225 encounter a bump or some other surface abnormality that would cause a shock to transfer cart 200. Additional shock-absorbing springs 230 or resilient springs 235 may be mounted to any other load-bearing parts of transfer cart 200 so as to provide shock absorption during transportation of mobile sterilization system 100.

Transfer cart 200 may also comprise a "dead man's" safety grip and/or auto-braking system. More particularly, and still looking at FIG. 5, there is shown a dead man's safety grip 240. Dead man's safety grip 240 is connected (either electronically, mechanically or otherwise) to one or more wheel brakes capable of preventing casters (or other wheels) from moving (not shown). In one form of the invention, the wheel brakes are configured so that their default position is with the brakes applied to casters 225 of transfer cart 200, thereby prohibiting movement of transfer cart 200. When dead man's safety grip 240 is actuated by a user, the wheel brakes are moved to a second configuration, whereby to allow the wheels to roll freely. Accordingly, the wheels (and, by extension, the transfer cart) are prevented from rolling unless dead man's safety grip 240 is actuated. This feature provides foolproof braking during loading and unloading of sterilization cabinet 105 onto transfer cart 200, and during loading and unloading of the contents of sterilization cabinet 105.

Transfer cart 200 may also comprise a power assist mechanism 245 (FIG. 4) which can be built into, or otherwise attached to, transfer cart 200. As shown in FIG. 5, power assist mechanism 245 may comprise a motor configured to drive casters 225 when a motor/servo power assist handle or other control (not shown) is actuated by a user (e.g., by turning the handle, in the manner of a motorcycle throttle grip). Power assist mechanism 245 may assist in the transportation of heavier loads for longer distances, on inclines and/or over uneven surfaces. Power assist mechanism 245 may drive the wheels either forward or in reverse.

Figure 6:
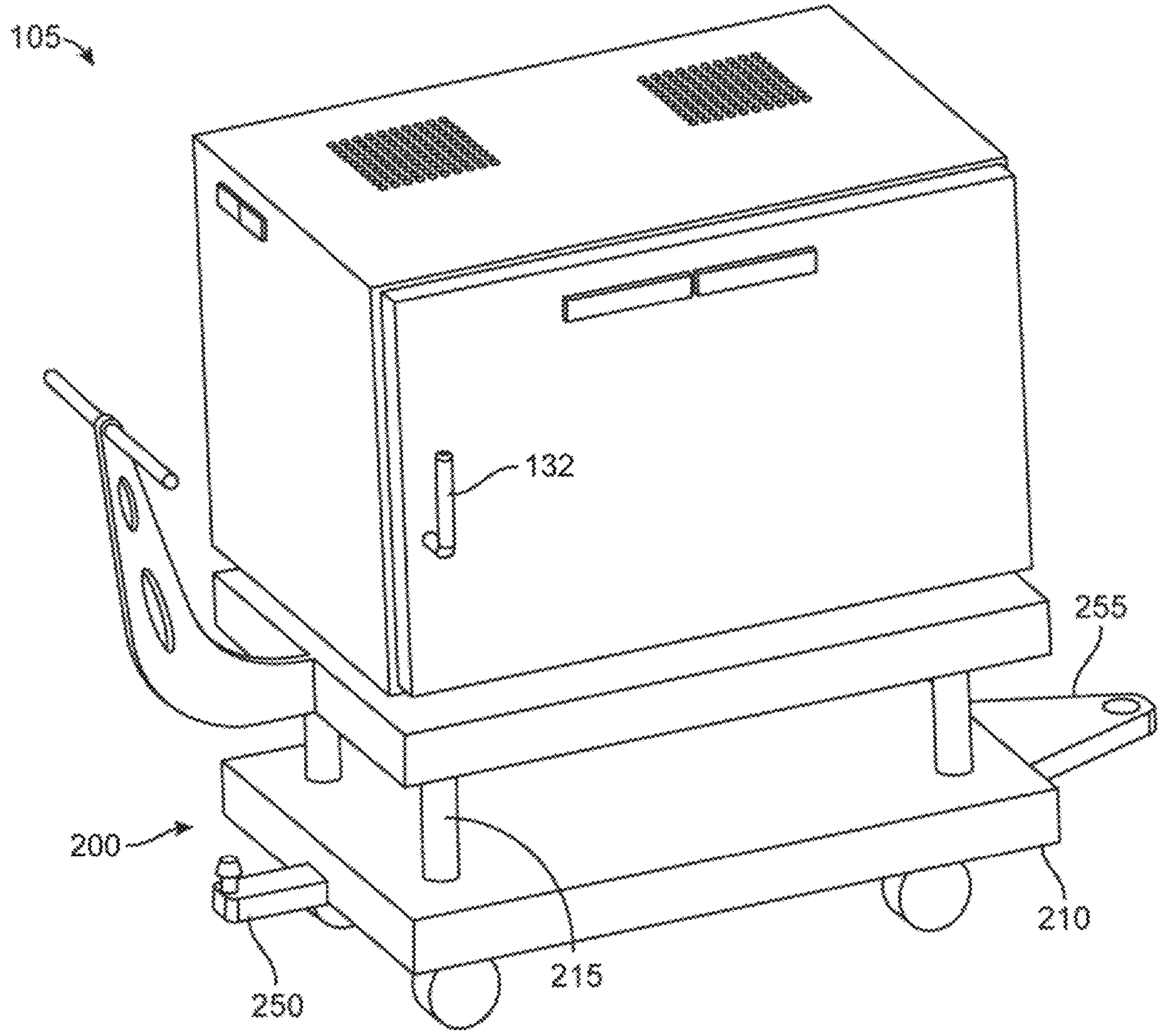
Figures 7A, 7B, 7C, 7D:
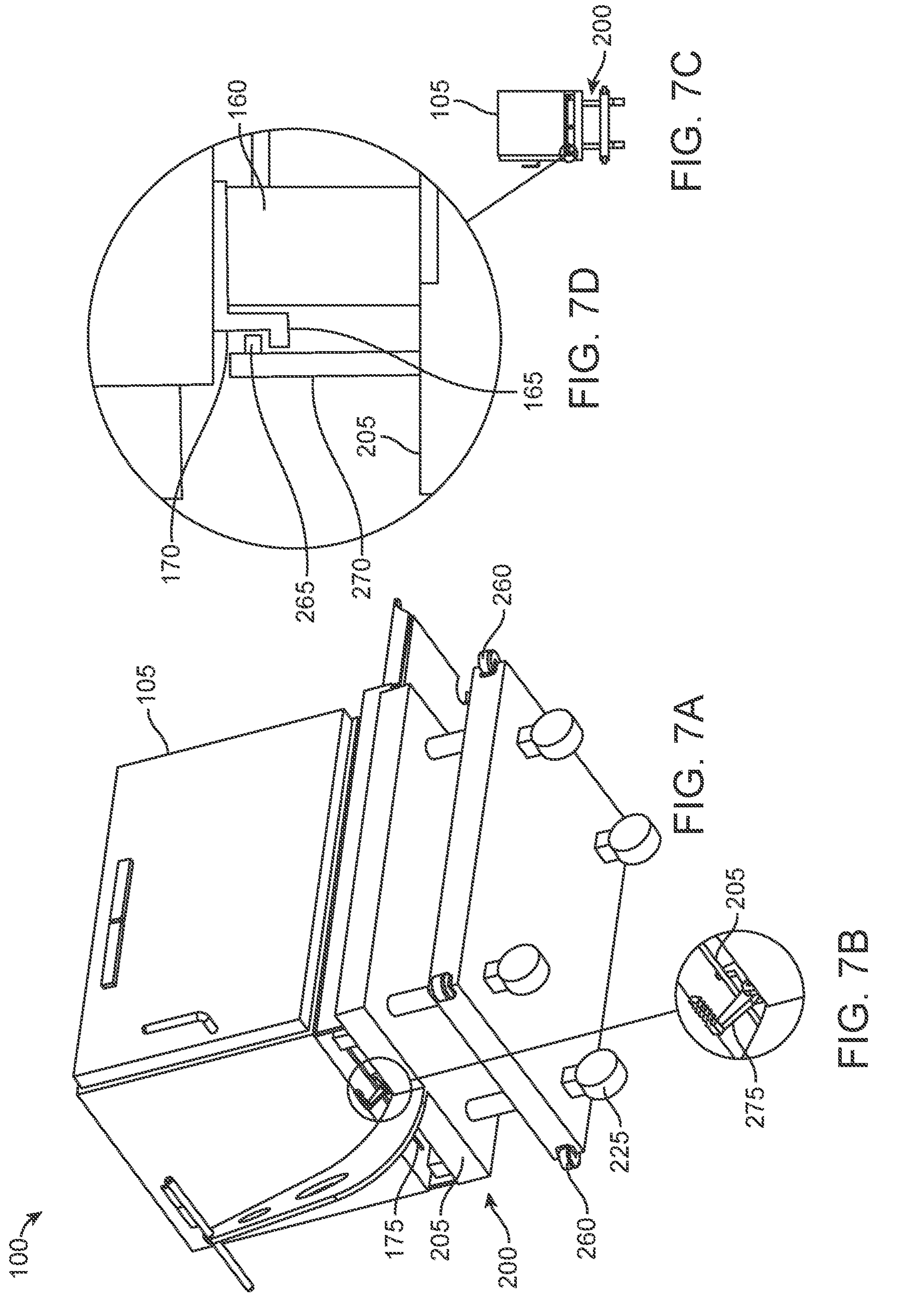

In one embodiment, and looking now at FIG. 6, transfer cart 200 may be provided with a mechanism for linking the transfer cart to one or more other transfer carts 200 so that the transfer cart may be used to tow (or push) another transfer cart during transport between locations. To effectuate such linking capability, transfer cart 200 may be provided with a male component 250 at one end of lower platform 210 of transfer cart 200 and a female component 255 disposed at the opposite end of lower platform 210 of transfer cart 200, whereby to allow the male or female component of a given cart to be linked with the complementary male or female component on another cart. One or both of male component 250 and female component 255 can be retracted or folded under transfer cart 200 when the transfer cart or tugging/linking feature is not in use.

In one embodiment, transfer cart 200 may also be configured with bumpers and/or rollers 260 (FIG. 7A) to protect transfer cart 200 and/or other objects, and to otherwise facilitate movement of transfer cart 200 from one location to another (e.g., during transportation through a hospital hallway).

Looking now at FIGS. 7A-7D, transfer cart 200 is preferably releasably secured to cabinet 105 by a combination of complimentarily configured tracks or rails and a locking latch or similar device.

Preferably, transfer cart 200 is provided with an improved safety feature of interlocking tracks or rails to catch interlocking caster brackets (which mount to casters or wheels 160 to cabinet 105). More particularly, lips 265 extend inboard from a pair of transfer cart tracks or rails 270, which themselves extend upward from a side or top surface of upper platform 205 of transfer cart 200 (i.e., with one track or rail 270 extending along each side of transfer cart 200). Lips 265 are configured to slidably engage elongated projection 165 of cabinet caster or wheel bracket 170 so as to prevent sterilization cabinet 105 from moving either laterally (i.e., side-to-side), or up-and-down, with respect to transfer cart 200 while cabinet 105 is positioned on transfer cart 200.

Transfer cart 200 and sterilization cabinet 105 are preferably formed so as to provide autolocking features to keep cabinet 105 secured to transfer cart 200. More particularly, and looking now at FIGS. 7A and 7B, transfer cart 200 may be configured with a center locking latch 275 that is mounted to upper platform 205 of transfer cart 200. Center locking latch 275 may be configured to receive a bar 175 which extends across the bottom of sterilization cabinet 105 such that, after bar 175 is received by latch 275, sterilization cabinet 105 is prohibited from moving forward or backward with respect to transfer cart 200.

Transfer cart 200 is preferably configured so as to be "universal" by providing railings and attachments that are adjustable so as to be able to accommodate the dimensions of different sterilization cabinets or other cargo, and/or the dimensions of different destinations of sterilization cabinet 105 (e.g., different autoclaves or storage racks).

More particularly, and looking now at FIGS. 8A-8D, transfer cart 200 may be configured with universal railings 280 which are of adjustable width along directional arrow 1 or 3 shown in FIG. 8A, and a detachable adapter 285 which is also configured to be of adjustable width. Adjustable rails 280 and adapter 285 may be fit together, such as in the male/female configuration shown in FIG. 8B, so as to allow for a smooth surface for the transfer of sterilization cabinet 105 from transfer cart 200 to a destination (e.g., a storage rack, autoclave, etc.). The width of universal rails 280 and adapter 285 is determined at least in part by reference to the width of the corresponding features at the destination (e.g., it may be determined by the width of a storage rack or the relevant components of an autoclave).

Adapter 285 may be configured to extend straight out above upper platform 205 (such as is shown in FIG. 8A), or to fold down (such as is shown in FIGS. 8C and 8D) so as to not protrude at the end of transfer cart 200. Alternatively, adapter 285 may be configured so as to be entirely removable from the transfer cart. Where detachable adapter 285 is configured to be removable from transfer cart 200, adapter 285 may be further configured to be stowed in an unobtrusive location on transfer cart 200, or it may be configured to be stored near a destination location for ready use.

The universal fit feature described above improves production capacity, lowers cost, and enhances the ease and safety of moving mobile sterilization system 100 (e.g., through hospital hallways). When adapter 285 is removed and/or folded away (such as shown in FIGS. 8C and 8D), a blunt-nosed, shorter and less dangerous cart front is presented at the front end of mobile sterilization system 100. As discussed previously, adapter 285 may either stay with each transfer cart 200 as a folding or stowable component or it may be left at a desired destination (e.g., in a sterile processing department to be stored adjacent to the autoclave or next to a storage rack or rack system).

In another embodiment of the present invention, an alternative transfer cart is provided which is capable of being vertically adjusted so as to raise and lower the upper platform of a transfer cart (and, in turn, a sterilization cabinet 105 secured to the upper platform) in order to meet the needs of a user. By way of example, the upper platform of the transfer cart can be lowered for easier visibility during transportation between locations, and then raised to a desired height when the sterilization cabinet is opened at a desired location.

The vertically-adjustable transfer cart may be raised and lowered mechanically (e.g., such with a scissor lift, as will be discussed in further detail below) electronically, hydraulically, pneumatically, by a battery-operated power device, or by some other appropriate means.

Figure 9:
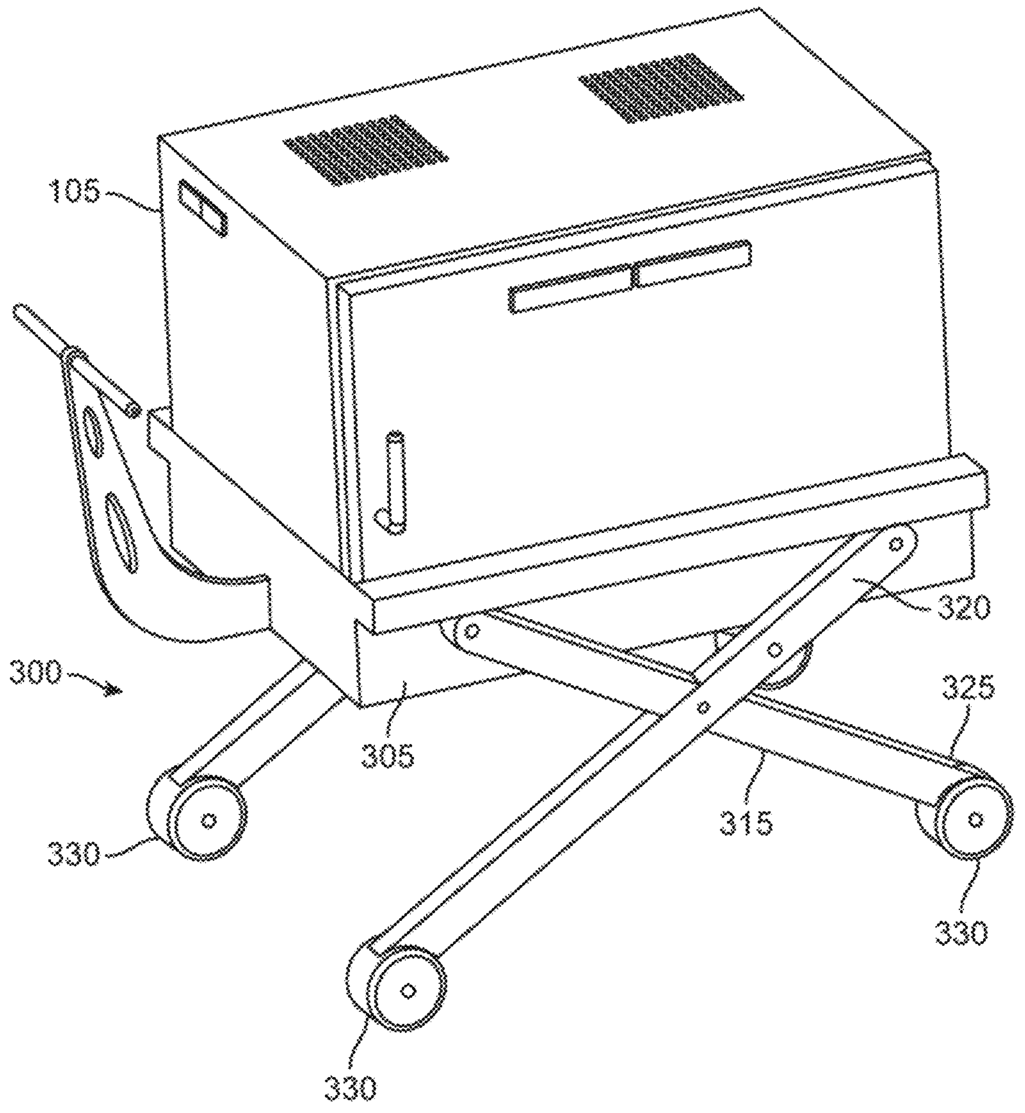
FIG. 9 is a schematic view showing a further embodiment of the novel sterilization cart of the present invention.

To this end, and looking now at FIG. 9, a vertically-adjustable transfer cart 300 is provided.

Vertically-adjustable transfer cart 300 is generally similar to transfer cart 200 discussed above, except that vertical risers 215 and lower platform 210 are replaced by a scissor lift 315 having an upper end 320 and a lower end 325.

Sterilization cabinet 105 is configured to be secured to upper platform 305 of transfer cart 300 in the same manner discussed above. Scissor lift 315 is connected to upper platform 305 at its upper end 320 and to wheels 330 at its lower end 325 for moving the transfer cart between locations.

In accordance with this aspect of the invention, scissor lift 315 may be actuated so as to enable upper platform 305 to be lowered until it is substantially flush with the floor.

Figure 10:
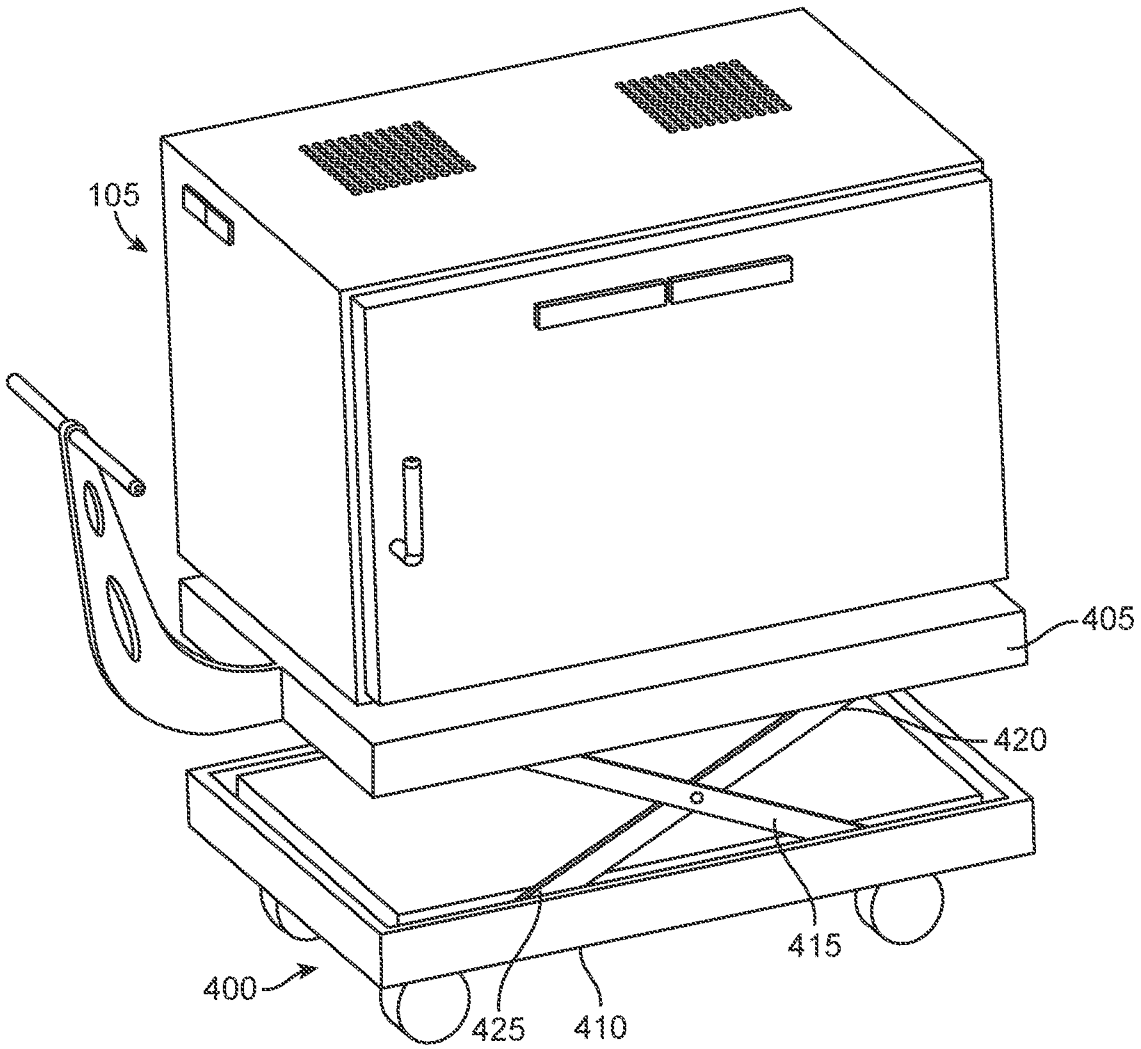
FIG. 10 is a schematic view showing another embodiment of the novel sterilization cart of the present invention.

In another embodiment of the present invention, and looking now at FIG. 10, a vertically-adjustable transfer cart 400 is provided. Transfer cart 400 is generally similar to transfer cart 200 discussed above, except that vertical risers 215 are replaced by a scissor lift 415 having an upper end 420 and a lower end 425.

More particularly, transfer cart 400 comprises an upper platform 405 which is configured to be secured to sterilization cabinet 105 as discussed above, a lower platform 410 and a scissor lift 415 extending between upper platform 405 and lower platform 410.

Actuation of scissor lift 415 in this embodiment will move upper platform 405 up and down, as described above, however, upper platform 405 is not lowered all the way to ground level (i.e., it is lowered to the level of lower platform 410). This embodiment can provide additional stability for transfer cart 400.

Scissor lifts 315 and 415 of transfer carts 300 and 400, respectively, may be actuated (i.e., raised and lowered) by a lift mechanism that can be a mechanical hand-crank or hydraulic or pneumatic hand-pump, or which may be power-assisted (mechanical, hydraulic, pneumatic, etc.) via electric or battery operation.

In addition, transfer carts 300 and 400 may comprise an electronic control system (such as that shown in FIG. 11 and discussed in more detail below) which may allow a user to pre-program specific heights into the electronic control system, which will direct the transfer cart to assume a desired height (e.g., for loading the sterilization cabinet into a particular autoclave, or a preferred height for operating room or sterile processing department staff who will unload, load or transport the sterilization cabinet). This feature allows for height adjustments, thereby providing ergonomic benefits without compromising the sterile field on account of the nurse or scrub technician's physical stature.

An additional benefit of the height adjustment feature described above is that the sterilization cabinet can be lowered to allow for better line of sight over the top of the cabinet during transportation and to provide a lower center of gravity so as to reduce the possibility of tipping. The pre-programmed heights may be set by the user as discussed above. The systems of the present disclosure can include a robotic or automated lift for the sterilization unit 100 and transfer cart, which allows the unit 100 to be raised and lowered to different heights. In use, the unit 100 is transferred to the robotic lift (or the lift can be positioned on the transfer cart) where the robotic lift lowers the unit 100 to match the height of the autoclave entrance. For instance, some autoclaves are six inches off the ground, while others are table height or higher. The cart and robotic lift are removed from the unit 100 during sterilization and then can be connected back to the unit 100 so that the unit can be transferred to any other structure and adjust for the height of that structure. In addition, any of the systems described herein can include a conveyor belt or roller system to move the unit 100 into an autoclave or sterilization unit.

Figure 11:
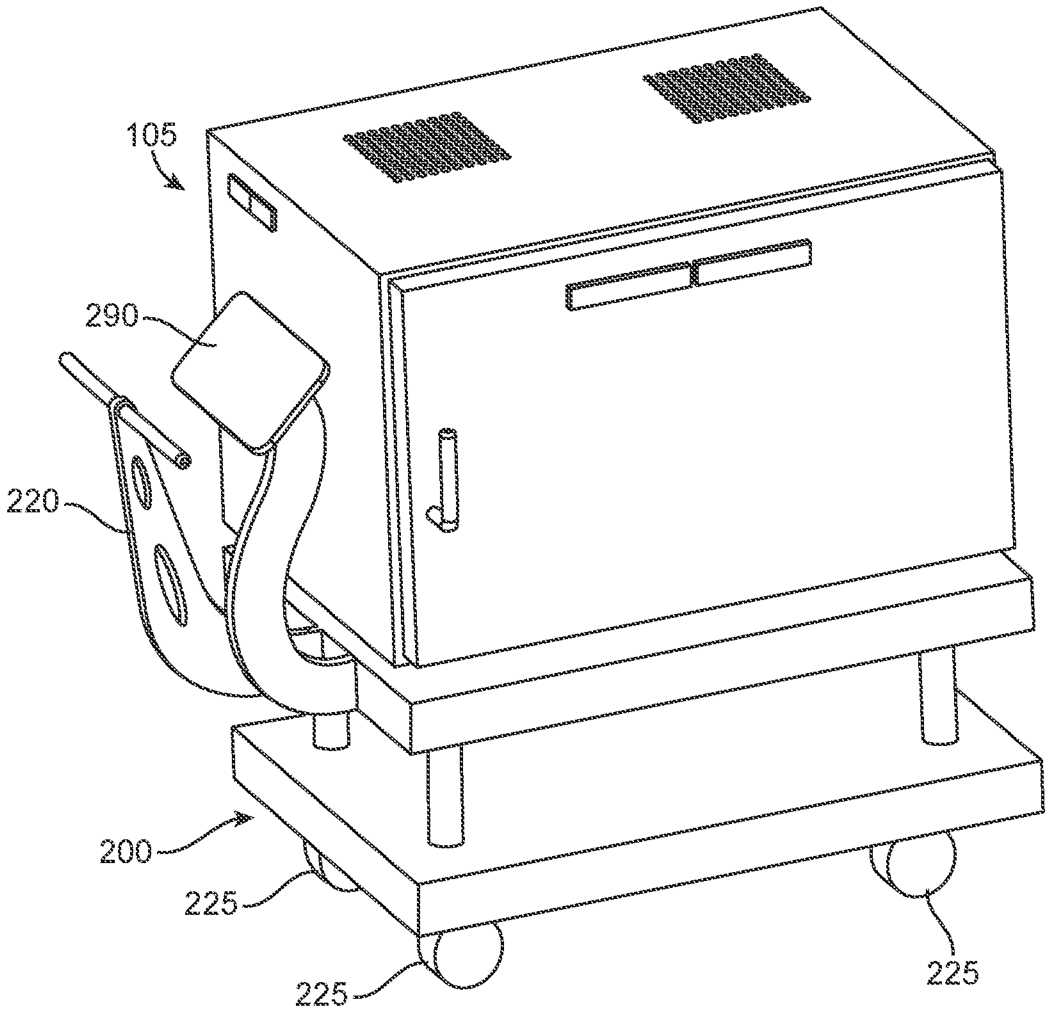
FIG. 11 is a schematic view showing an electronic control system of the mobile sterilization system of the present invention.

Looking now at FIG. 11, the transfer cart of the present invention (e. g., transfer carts 200, 300 and 400) may also be provided with an electronic control system 290 for tracking and/or identifying the transfer cart and the contents of sterilization cabinet 105.

More particularly, electronic control system 290 of the transfer cart of the present invention preferably has the ability to be electronically traced with a LOJACK®-like device, or a similar tracing-type system. In other words, the location of the transfer cart (e.g., building, floor, room) may be remotely monitored by use of a global positioning system (GPS), radio-frequency identification (RFID), or other location-tracking device.

In addition, electronic control system 290 may use RFID, or other identification technology, to identify a particular sterilization cabinet 105, the contents of that sterilization cabinet 105 (e.g., trays or instruments), its location, current temperature, and/or sterilization status (e.g., pre-or post-sterilization, sterile or non-sterile, etc.). Electronic control system 290 may also provide additional information such as date, operator, cycles, cycle type, and contents inside sterilization cabinet 105, among other things.

The information provided by electronic control system 290 may be displayed on a screen to a user, or audibly delivered through a speaker to a user.

Figure 12:
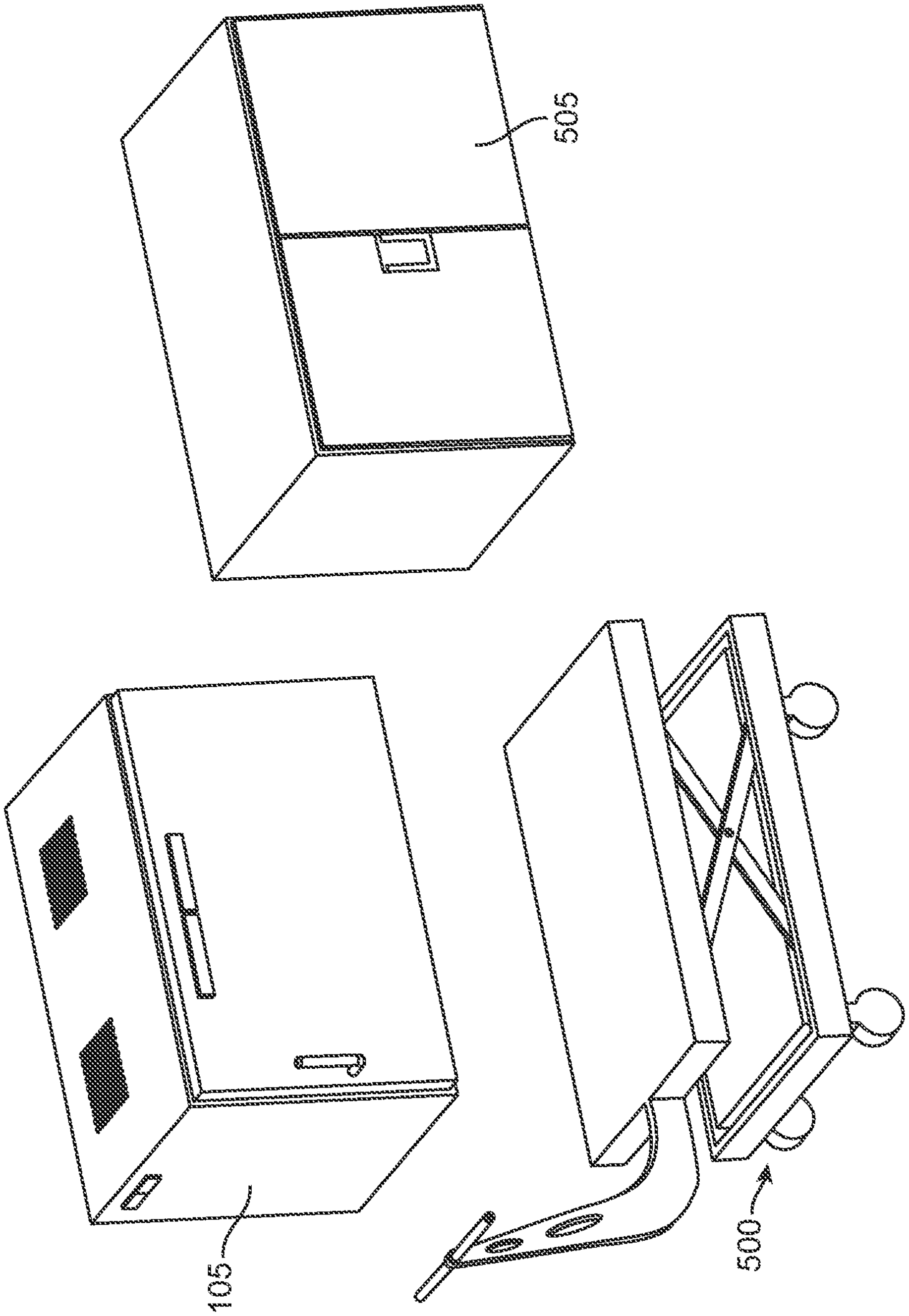
FIG. 12 is a schematic view showing a universal transfer cart formed in accordance with the present invention.
Figure 20:
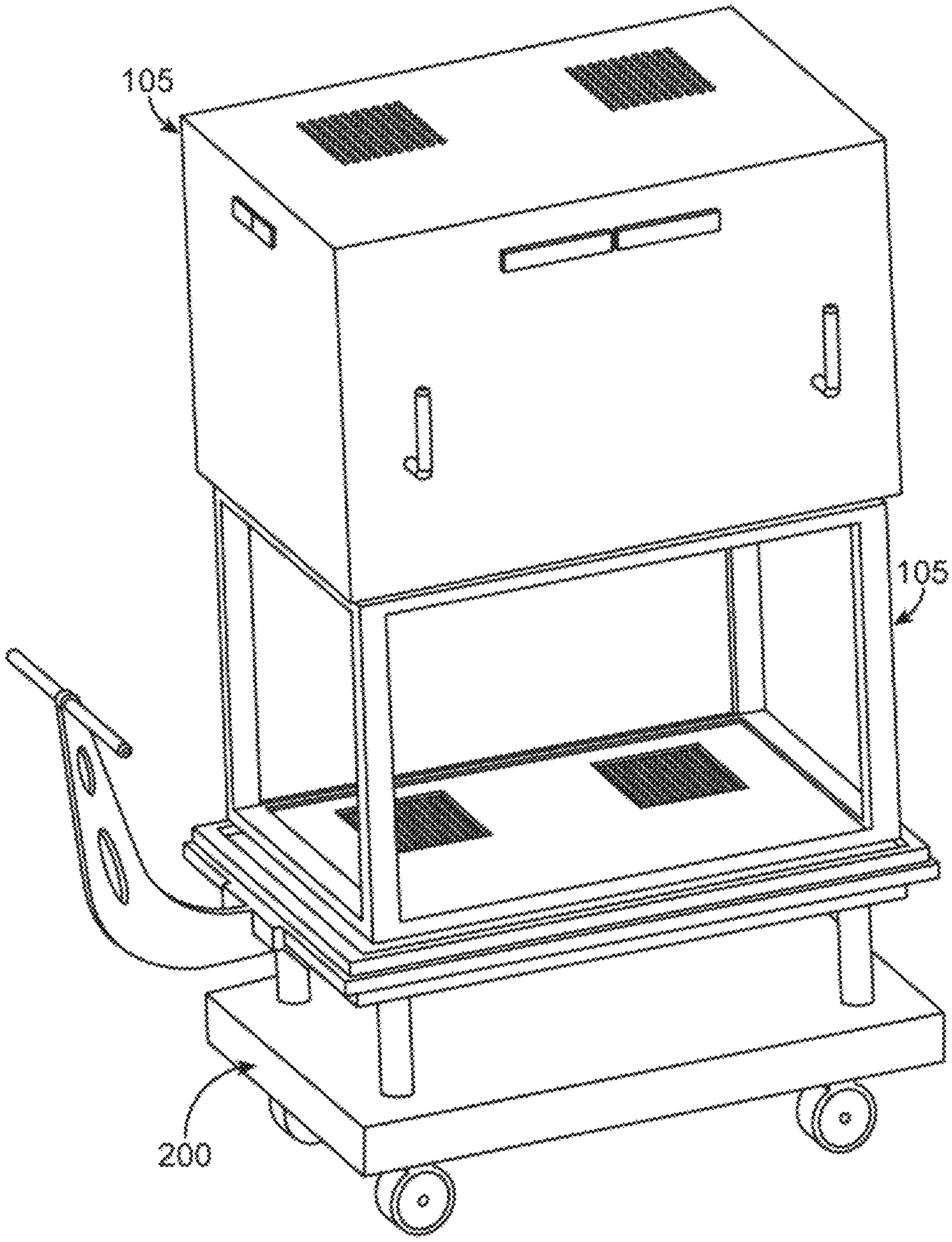

Looking now at FIG. 12, a universal transfer cart 500 is provided. Universal transfer cart 500 may act as a transfer cart for other apparatus (e.g., an interchangeable case cart component 505 for holding instrument trays, but not sterilizing instrument trays) in addition to acting as a transfer cart for sterilization cabinet 105. Sterilization cabinets and case cart components can be vertically stacked on storage racking systems, e.g., up to 4 cabinets high. See, for example, FIG. 20, which shows (schematically) two sterilization cabinets 105 vertically stacked on top of one another. Alternatively, the case cart 505 can be configured to be a bottom portion of a transfer cart 200 such that a sterilization cube 100 can be positioned on a case cart rather than a transfer cart. The case cart can then be used to contain other goods needed for the cube-specific surgery that were not sterilized within the cube itself (for instance, disposable goods like gowns, drapes, gloves, sutures, etc.). The cube can contain the instrument trays and the case cart can contain the rest of the needed equipment and materials for that surgery.

Looking now at FIGS. 13-27, additional features of sterilization cabinet 105 will now be discussed in further detail.

In a preferred form of the present invention, door 130 can be provided in a variety of configurations in order to minimize the footprint needed when access to the interior of sterilization cabinet chamber 105 is required.

Figure 13:
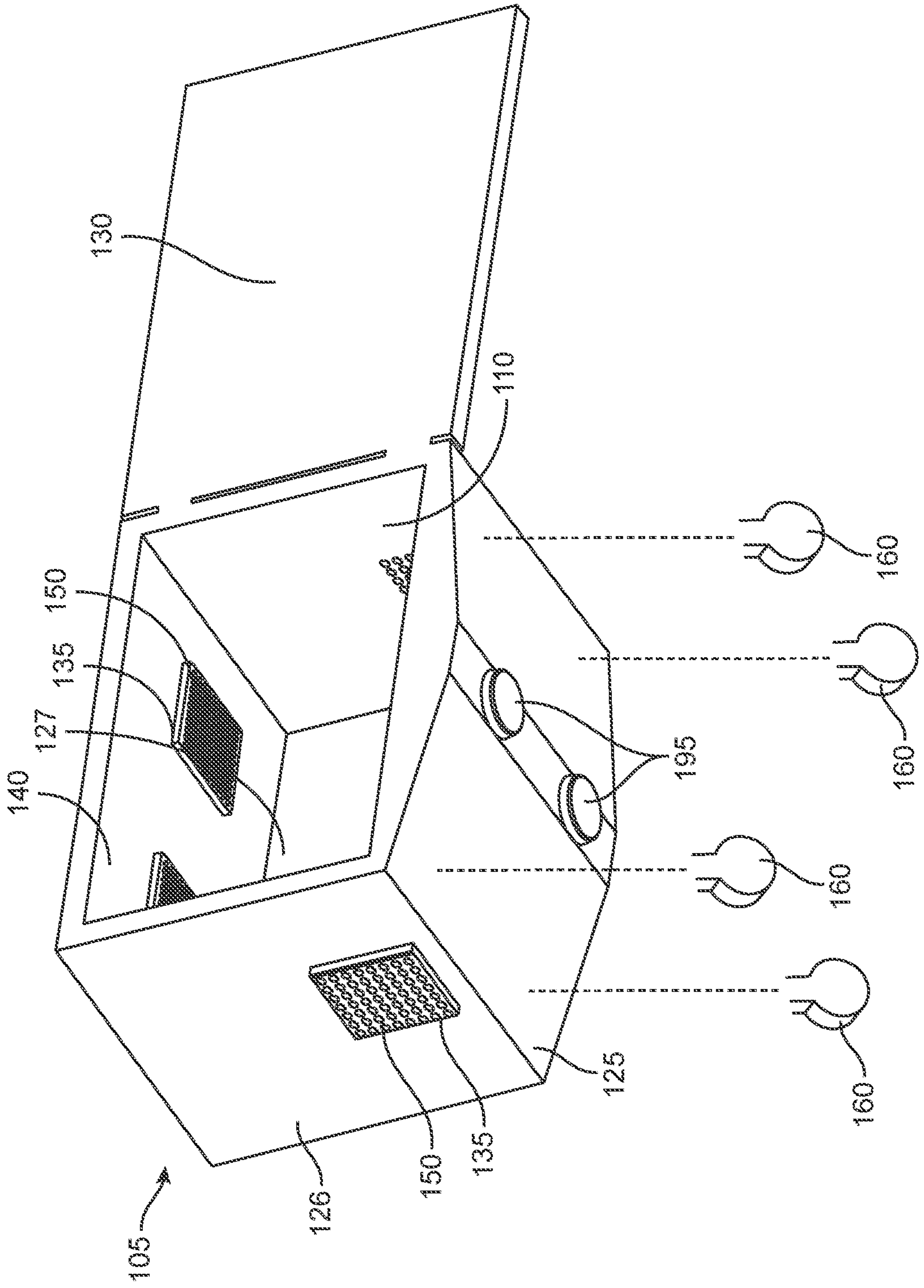
FIGS. 13-21, 22A, 22B, 23, 24, 25A and 25B are schematic views showing further details of the mobile sterilization system of the present invention.

In one embodiment of the present invention, and looking now at FIG. 13, door 130 can be hinged to one side of sterilization cabinet 105 and opened 180 degrees.

Figure 14:
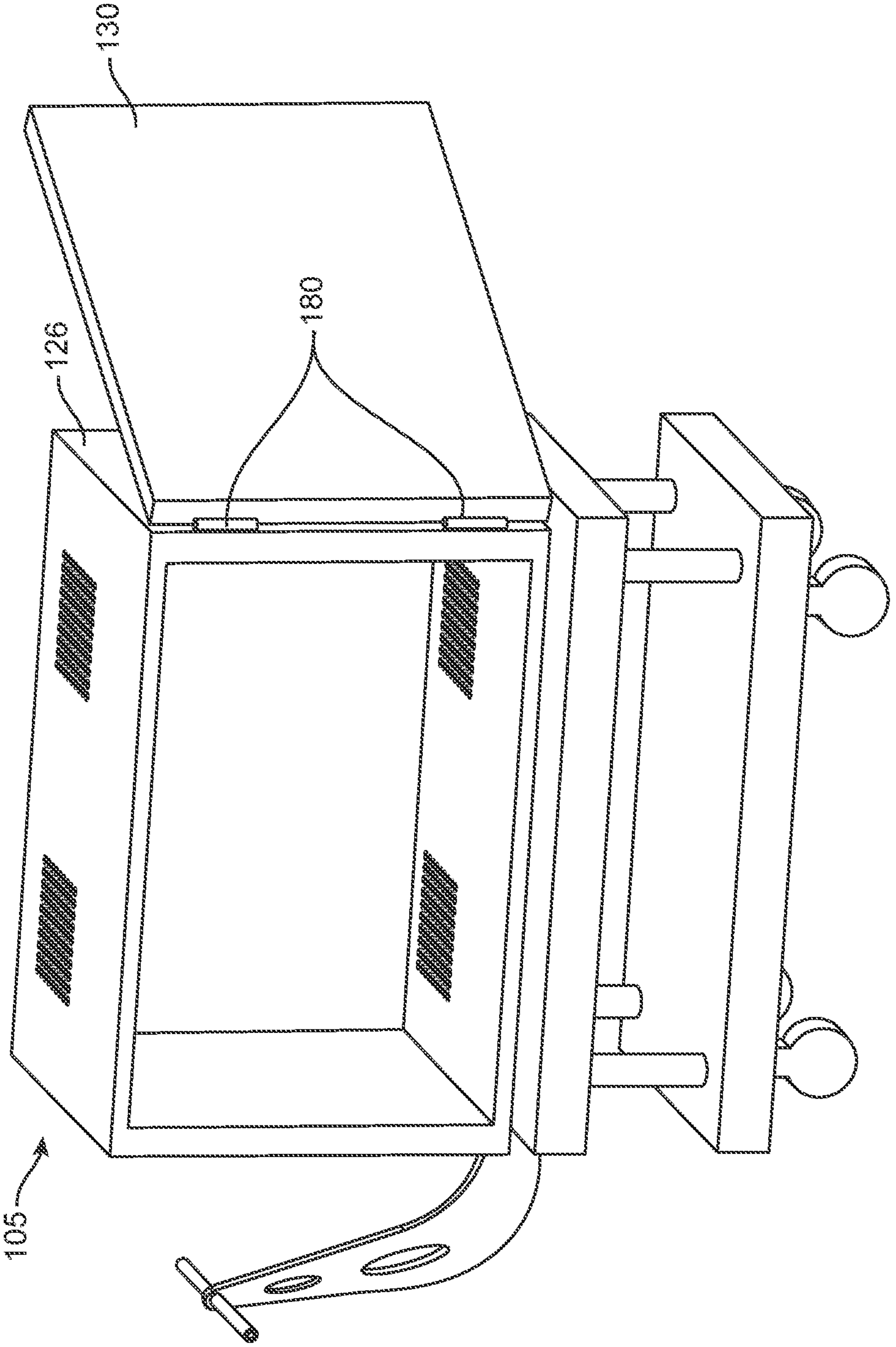

In another embodiment of the present invention, and looking now at FIG. 14, door 130 can be mounted to cabinet side wall 126 with hinges 180 so as to allow door 130 to open 270 degrees. If desired, door 130 and side wall 126 may be equipped with apparatus (e.g., a "hook and mesh" fastener, such as a Velcro™ fastener) so as to allow door 130 to be releasably secured to side wall 126 of cabinet 105 in order to keep the open door proximate to (and roughly parallel to) side wall 126 of cabinet 105, thereby reducing the overall footprint of cabinet 105 when door 130 is open.

Figure 15:
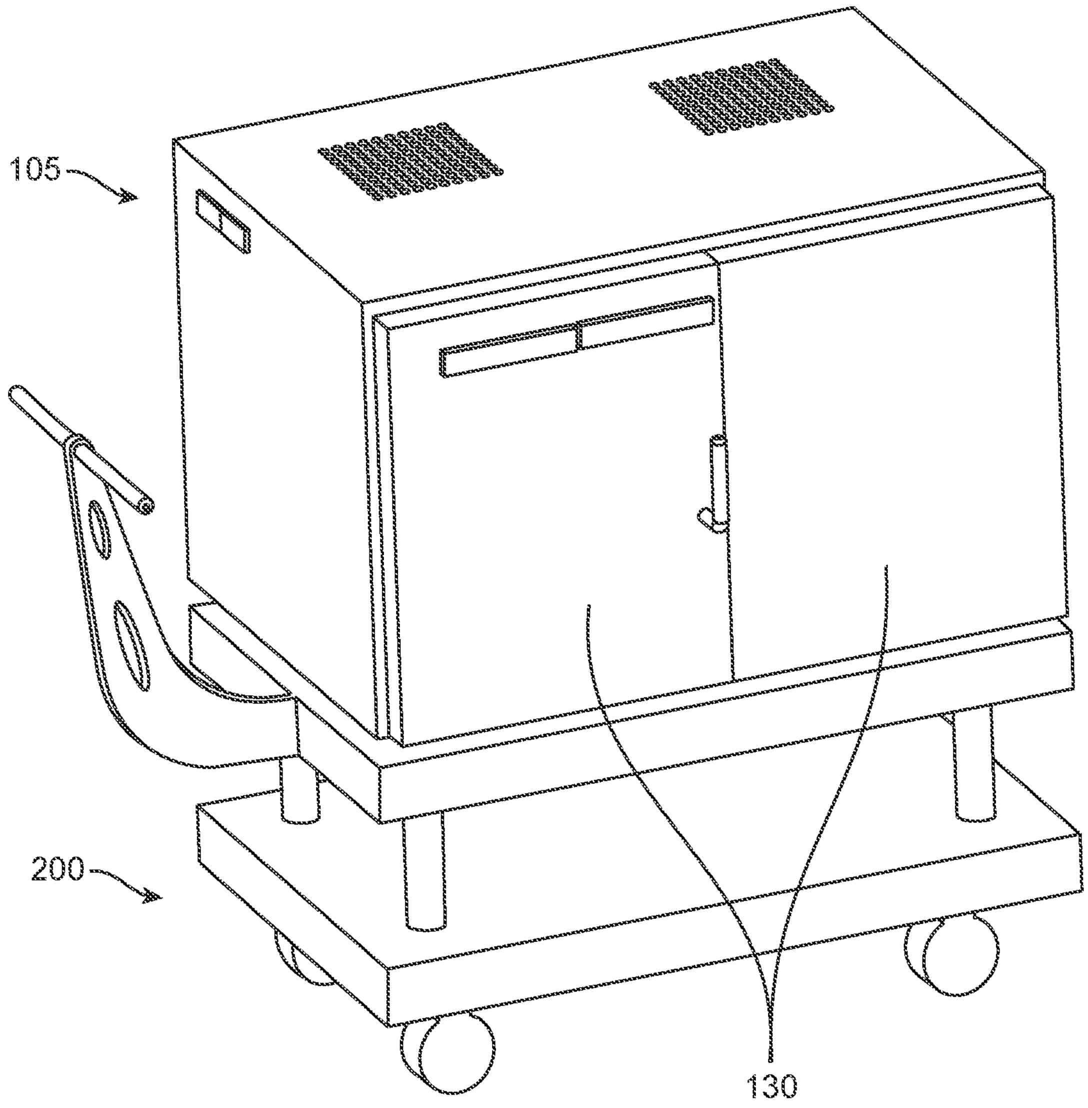

In another embodiment of the present invention, and looking now at FIG. 15, door 130 can comprise a pair of French doors 130, with a gasket or other sealing closure in the middle of, and around, each door 130 (not shown), and with both French doors 130 optionally being configured to be opened and releasably attached to the side of the cabinet in the manner described above.

Figure 16:
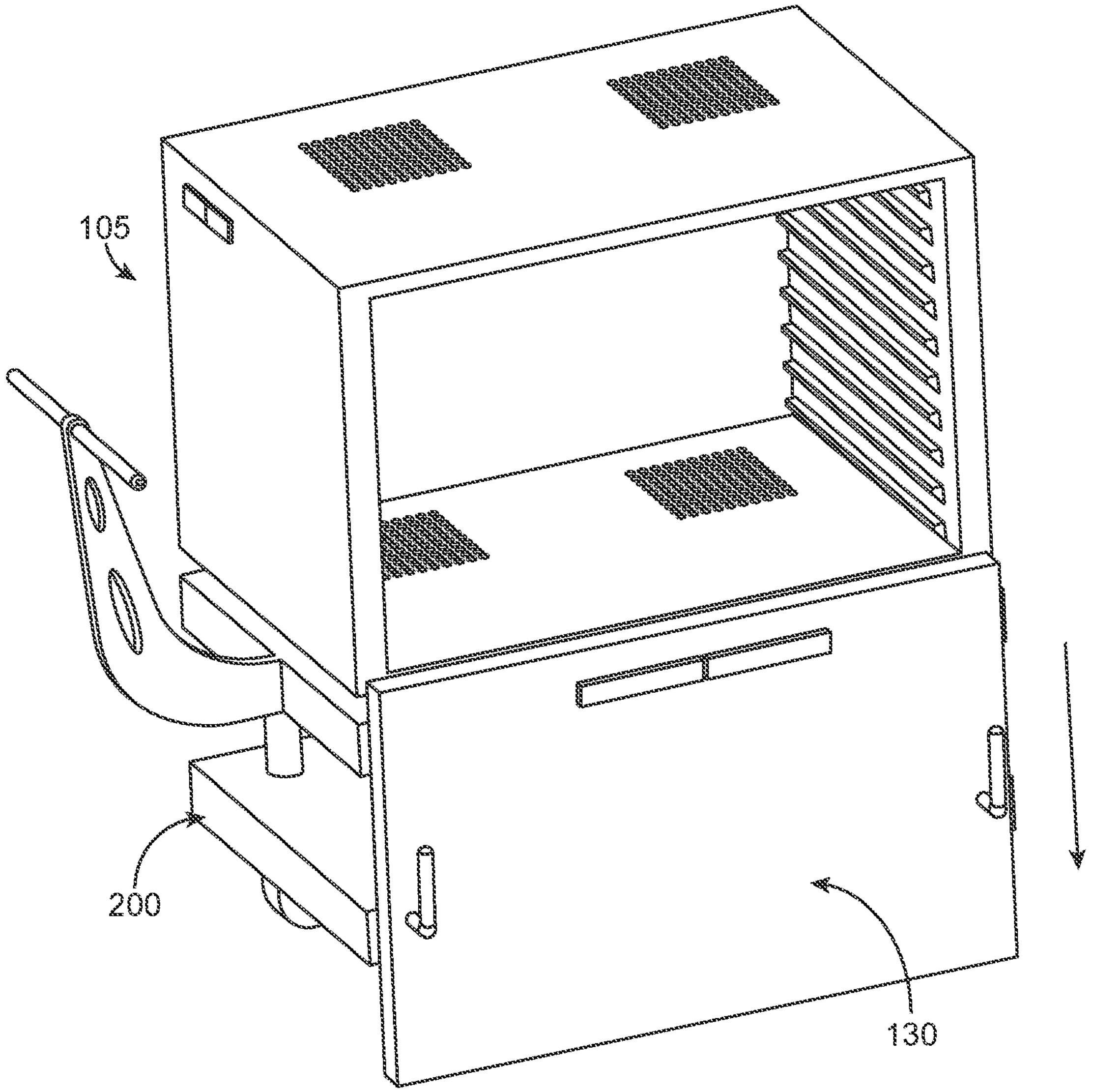
Figure 17:
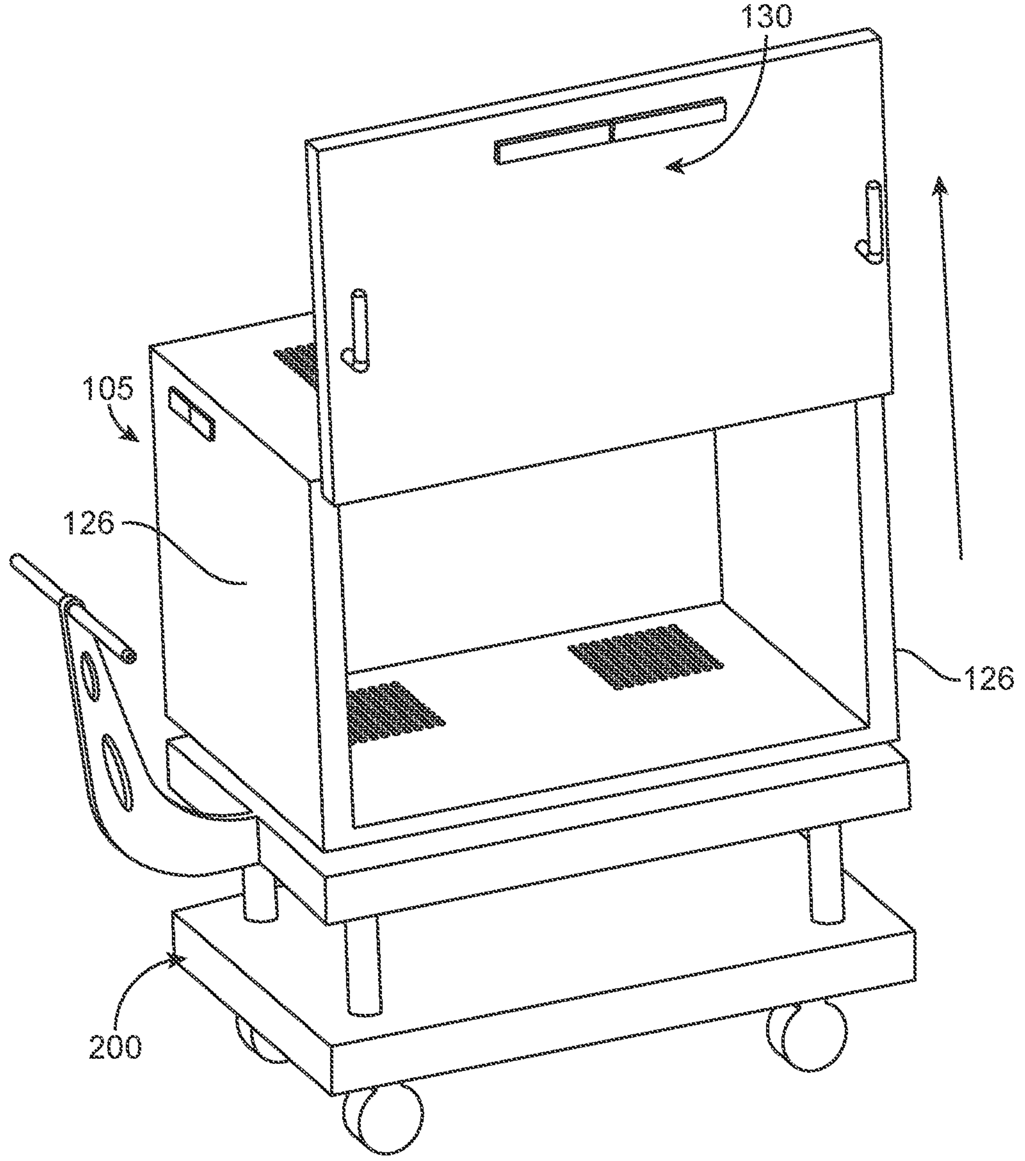

In still another embodiment of the invention, and looking now at FIGS. 16 and 17, door 130 can be opened and slid down (as in FIG. 16) or up (as in FIG. 17) along an internal or external track (not shown) positioned along the left and/or right side walls 126 of sterilization cabinet 105. Alternatively, door 130 may be swung over the top of sterilization cabinet 105 (not shown).

Figure 18:
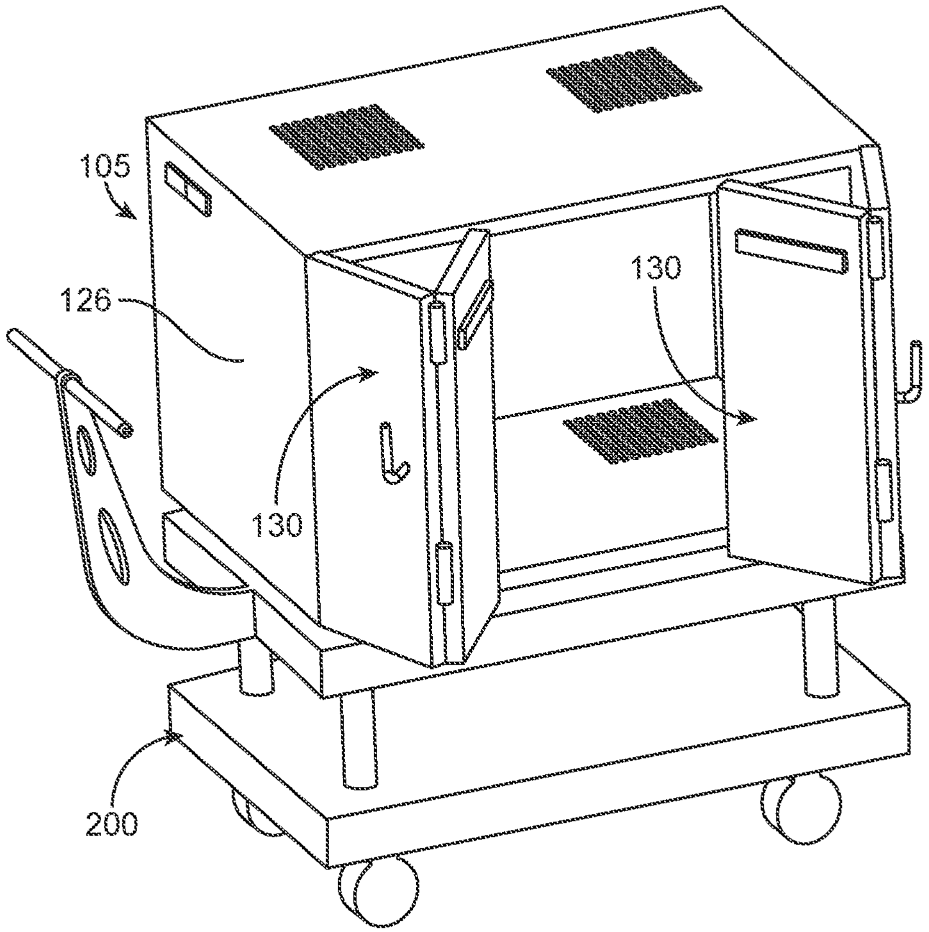

In yet another embodiment of the present invention, and looking now at FIG. 18, door 130 may comprise one or more bi-fold door(s) 130 which may be opened (and folded away) so as to expose interior chamber 110. In one preferred form of the invention, bi-fold door(s) 130 are constructed so that they may be folded back 270 degrees (e.g., in the manner described above) so that door(s) 130 may be positioned approximately parallel to side wall 126 of sterilization cabinet 105. Additionally, bi-fold door(s) 130 and side walls 126 are preferably constructed so as to allow door(s) 130 to be releasably secured to side walls 126 (e.g., with a "hook and mesh" fastener, e.g., a Velcro™ fastener) when door(s) 130 are folded back against side walls 126.

In another form of the present invention, the sterilization cabinet can have a dome closing top (not shown) rather than a door, i.e., the top of the sterilizable cabinet can move upward to expose the contents of the sterilization cabinet. The shape of the dome top is generally configured to allow for an airtight fit around the sterilization cabinet. The dome top can be made from any material including a non-solid filtration material, or a solid material with or without one or more filtered vents.

Accordingly, the dome top may be any shape that allows it to be properly fit over the top of the frame of sterilization cabinet 105. In this embodiment, the dome top can be lifted (e.g., manually, mechanically, with electronic assist, etc.) to expose the contents of sterilization cabinet 105. If desired, the dome top may be formed of a transparent material so as to allow full visibility of the contents within sterilization cabinet 105

Figure 19:
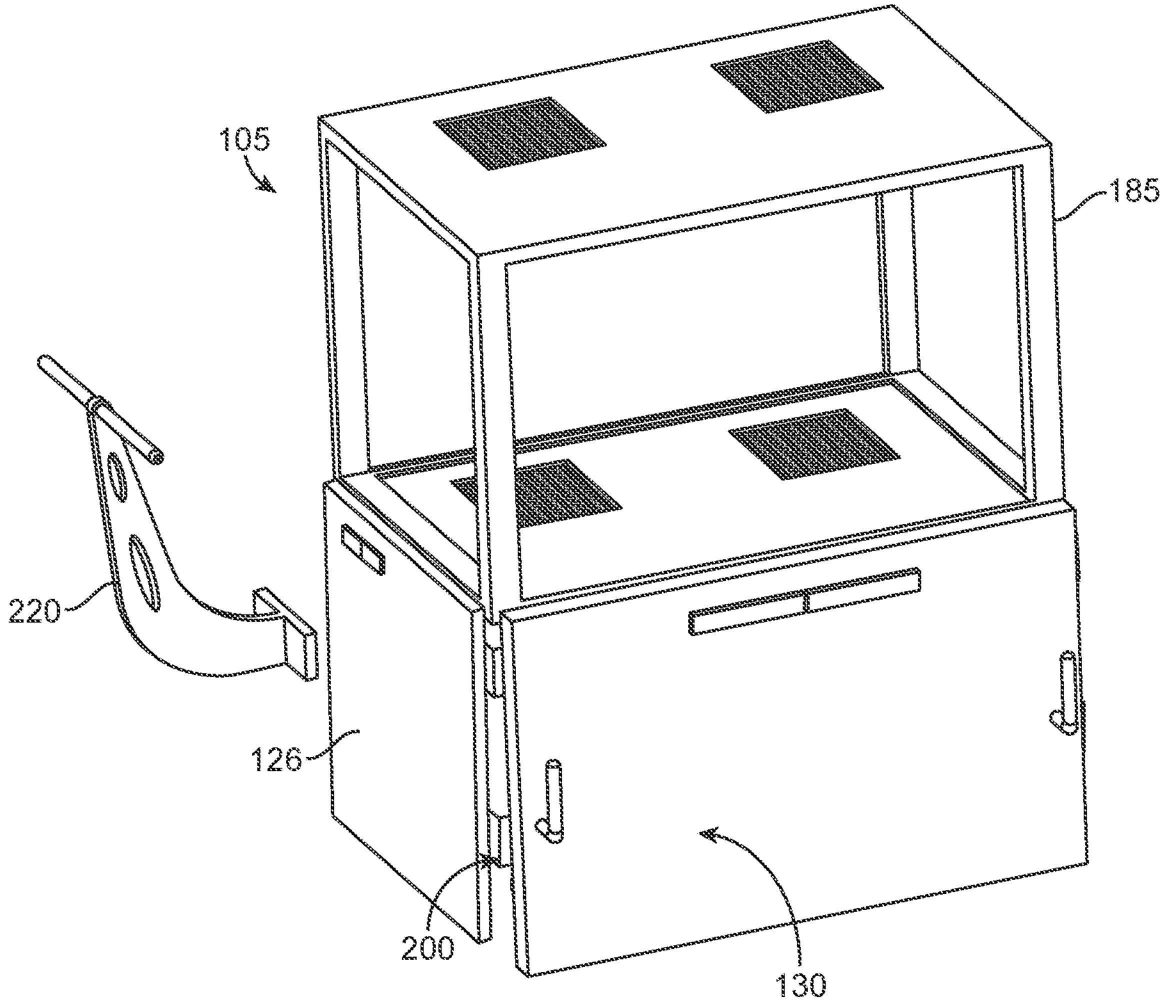

In still another form of the present invention, and looking now at FIG. 19, sterilization cabinet 105 may comprise a frame wherein back wall, side walls 126 and door(s) 130 can be loosened from frame 185 and slid down along internal or external tracks to the outside of the transfer cart 200. In this embodiment of the invention, handle 220 of transfer cart 200 may be removable so as to facilitate the smooth sliding of the side walls and/or door along the tracks.

In another preferred form of the present invention, means may be provided to enable a user to assess the contents of the sterilization cabinet without having to open the door of the sterilization cabinet.

More particularly, the entire sterilization cabinet 105 may be formed out of a transparent material (e.g., glass, a transparent polymer, etc.) so as to provide visibility to the contents within the sterilization cabinet. See, for example, FIG. 20, which shows a transparent sterilization container 105 positioned on top of transfer cart 200, and a second non-transparent sterilization container 105 positioned on top of transparent sterilization container 105.

Figure 21:
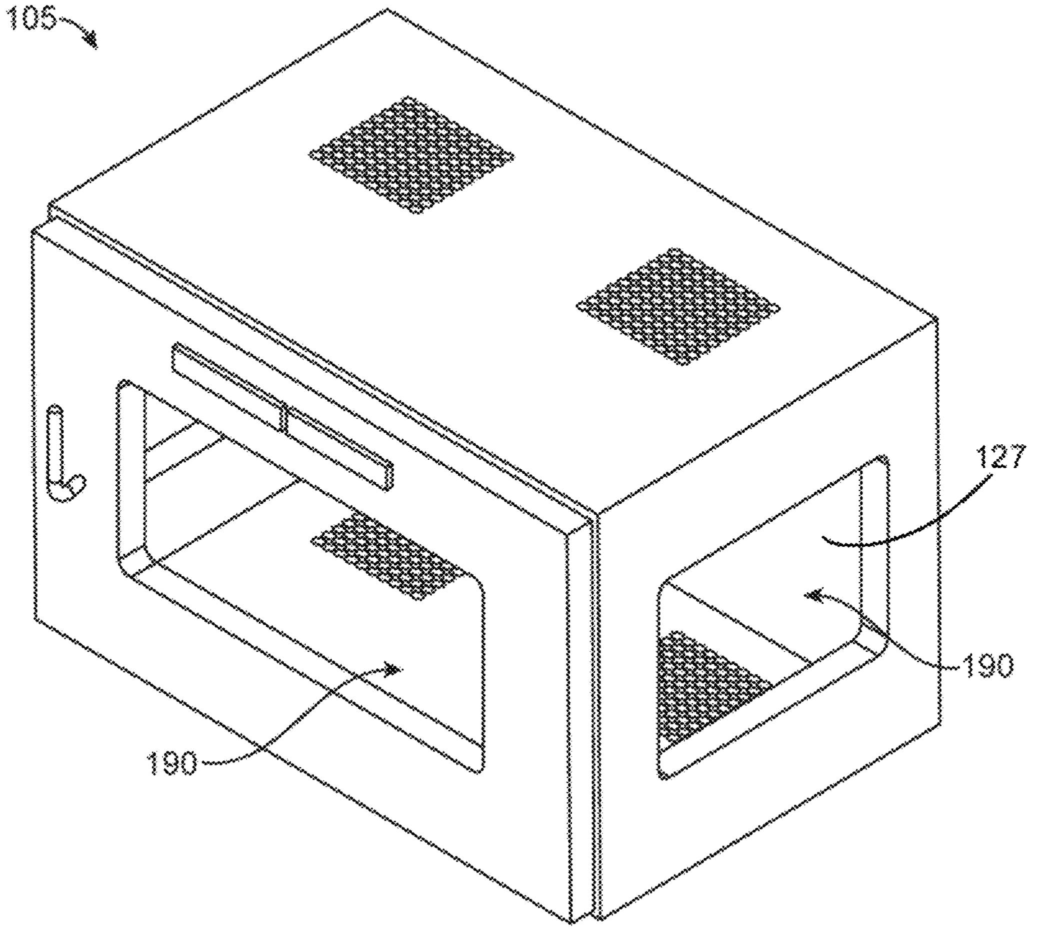
Figure 22A:
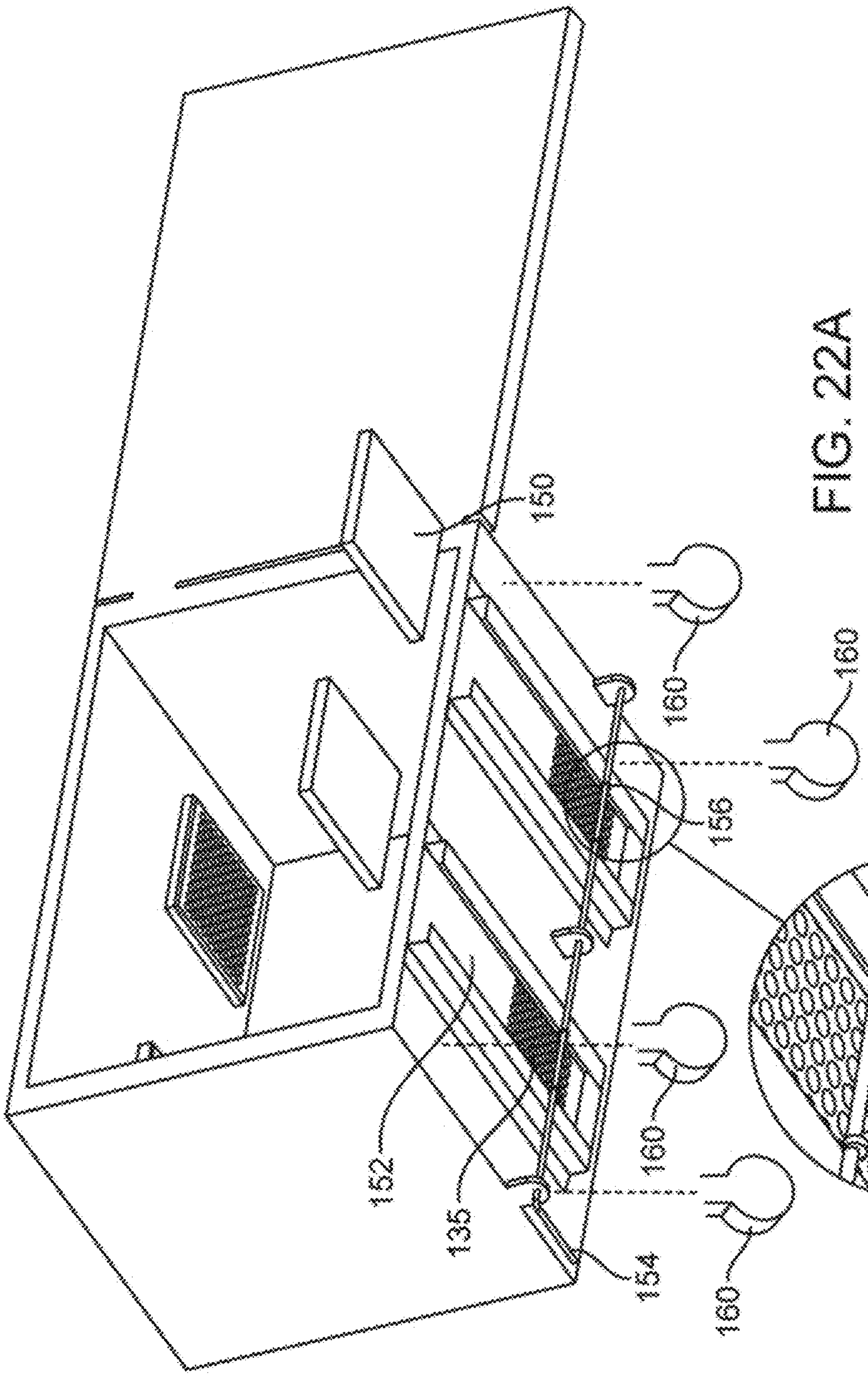
Figure 22B:
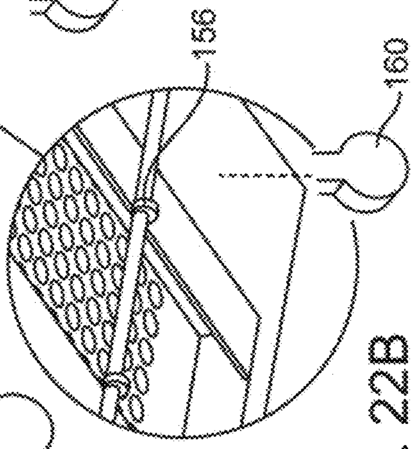

In another embodiment, and looking now at FIG. 21, sterilization cabinet 105 may be provided with one or more windows 190 (or "oven doors") located on one or more of the side walls 126, back wall 127 or door(s) 130 of sterilization cabinet 105. This allows for visibility into the cabinet to ascertain the contents of the cabinet and whether all of the desired equipment and instruments are enclosed.

If desired, the entire cabinet or window(s) 190 may be formed of a high temperature polycarbonate material and/or a "switchable" smart glass/film that changes from clear to opaque and/or another suitable material (e.g., to indicate a "sterile" or "non-sterile" state).

In another form of the present invention, an improved filter and filter port is provided in order to improve access to the filter for replacing, or otherwise accessing, the filter. Looking now at FIGS. 22A and 22B, sterilization cabinet 105 may be provided with filter ports 152 that are accessible from the outside of the cabinet, thereby allowing for easier access to check and change filters 150 (e.g., easier than with filter cover 155 FIG. 23). By way of example but not limitation, externally accessible filter port 152 may comprise a drawer-type access shelf for slidably receiving filters 150 and positioning the filter over vent 135. After being slidably placed in the desired position over vent 135 in filter port 152, filters 150 may be held in place by a locking bar 154 which controls a cam mechanism 156 (which releasably locks filters 150 in place).

Filter 150 may comprise cardboard, filter cassettes, reusable carbon filters or other filter materials and constructions known in the art. Filter 150 may also be a bi-layer filter created by sewing, gluing, encasing, crimping or pressing two layers of filter material together and forming to a desired size. Filter 150 may also be configured to change color to convey information concerning their status (e.g., a first color may indicate that a filter is suitable for use, while a second color may indicate that a filter should not be used and should be replaced, etc.). Thus, in one preferred form of the invention, the filter is manufactured using a process that incorporates chemical (s) into or onto the filter (in whatever pattern desired, including one requested by the customer) that will change color after the sterilization cabinet has been sterilized (as long as the sterilization process met certain predetermined parameters). In other words, the filters themselves become a Class 5 status indicator in addition to all of the other indicators which may be used during the sterilization process. This type of filter is a great improvement over the filters currently available on the market, as it provides a fail-safe mechanism to ensure that single use disposable filters are used only once. It also enables the operating room staff to visually confirm that the process has been accomplished by a quick glance at the large filter material.

Filters 150 may also be used for purposes other than in conjunction with an existing sterilization cabinet and/or mobile sterilization system 100.

In some applications of the present invention, it may be appropriate to not use any filters with the cabinets.

Looking again at FIG. 13, sterilization cabinet 105 may have a drain 195 positioned in the cabinet floor 125 to allow for the removal of water that may have accumulated within the cabinet during the sterilization process. In this construction, drain 195 is placed at the lowest point in the bottom of sterilization cabinet chamber 110. Preferably, bottom panel 125 is designed with a pitch to the lowest point in the panel, whether in the middle of the panel or along one side of the panel or in a corner of the panel. One or more drains may be used in each cabinet.

If desired, drain 195 may be thermostatically-controlled. In this form of the invention, drain 195 may be formed with a so-called "bimetallic" construction, e.g., a shape memory alloy such as Nitinol which can change configuration in response to temperature changes. By way of example but not limitation, drain 195 may be configured to open when the temperature within the sterilization cabinet is higher in order to release the excess water created during the sterilization process, and to close when the temperature within the sterilization cabinet is lower so as to seal the sterilization cabinet from potential containments. Alternatively, the bimetallic valve can also be controlled by pressure and time, not just temperature.

In another embodiment, drain 195 may be configured to open and close depending on the pressure level within the sterilization cabinet. By way of example but not limitation, drain 195 may be configured to open when the pressure within the sterilization cabinet is within a certain level in order to release the excess water created during the sterilization process, and to close when the pressure within the sterilization cabinet is within a certain level so as to seal the sterilization cabinet from potential containments.

In still another embodiment, drain 195 may be configured to open and close depending on the amount of time that has lapsed since the sterilization process. By way of example but not limitation, drain 195 may be configured to open during the time it takes to sterilize the contents of the sterilization cabinet in order to release the excess water created during the sterilization process, and to close after the contents of the sterilization cabinet have been sterilized so as to seal the sterilization cabinet from potential containments.

In a further embodiment of the present invention, sterilization cabinet chamber 110 comprises improved shelf management options so as to provide less cumbersome interior shelving than prior art sterilization cabinets.

Figure 23:
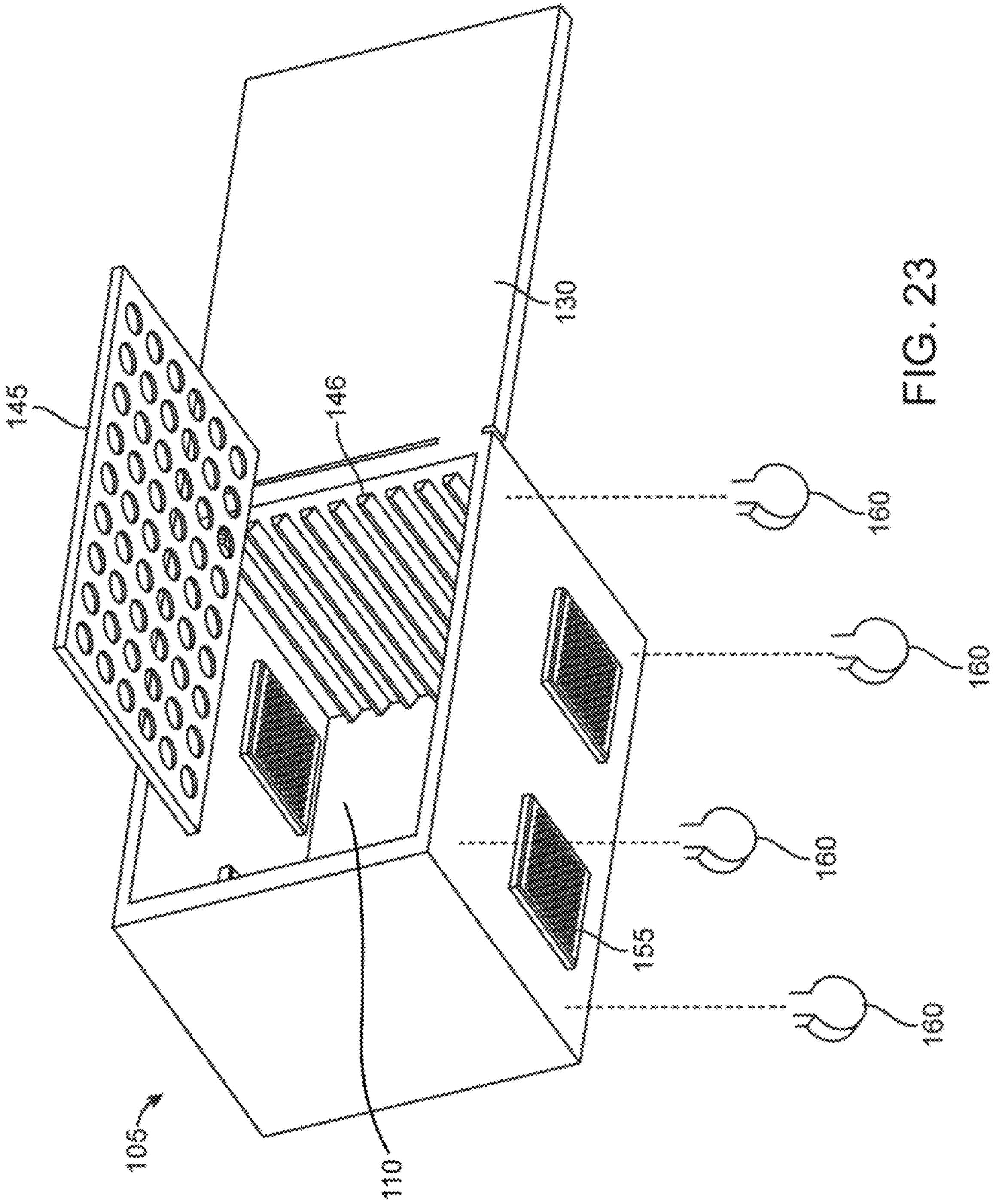

More particularly, and looking now at FIG. 23, sterilization cabinet chamber 110 may be configured with "wrinkle walls" or stamped walls 146 for ease of removing and replacing shelves 145 at multiple heights without the need for adjusting clips within the cabinet. In this aspect of the invention, shelves 145 are adjustable into varying height positions, where adjustments can be accomplished with one hand (e.g., through the use of "squeeze and release" shelving or other similar alternatives).

Figure 24:
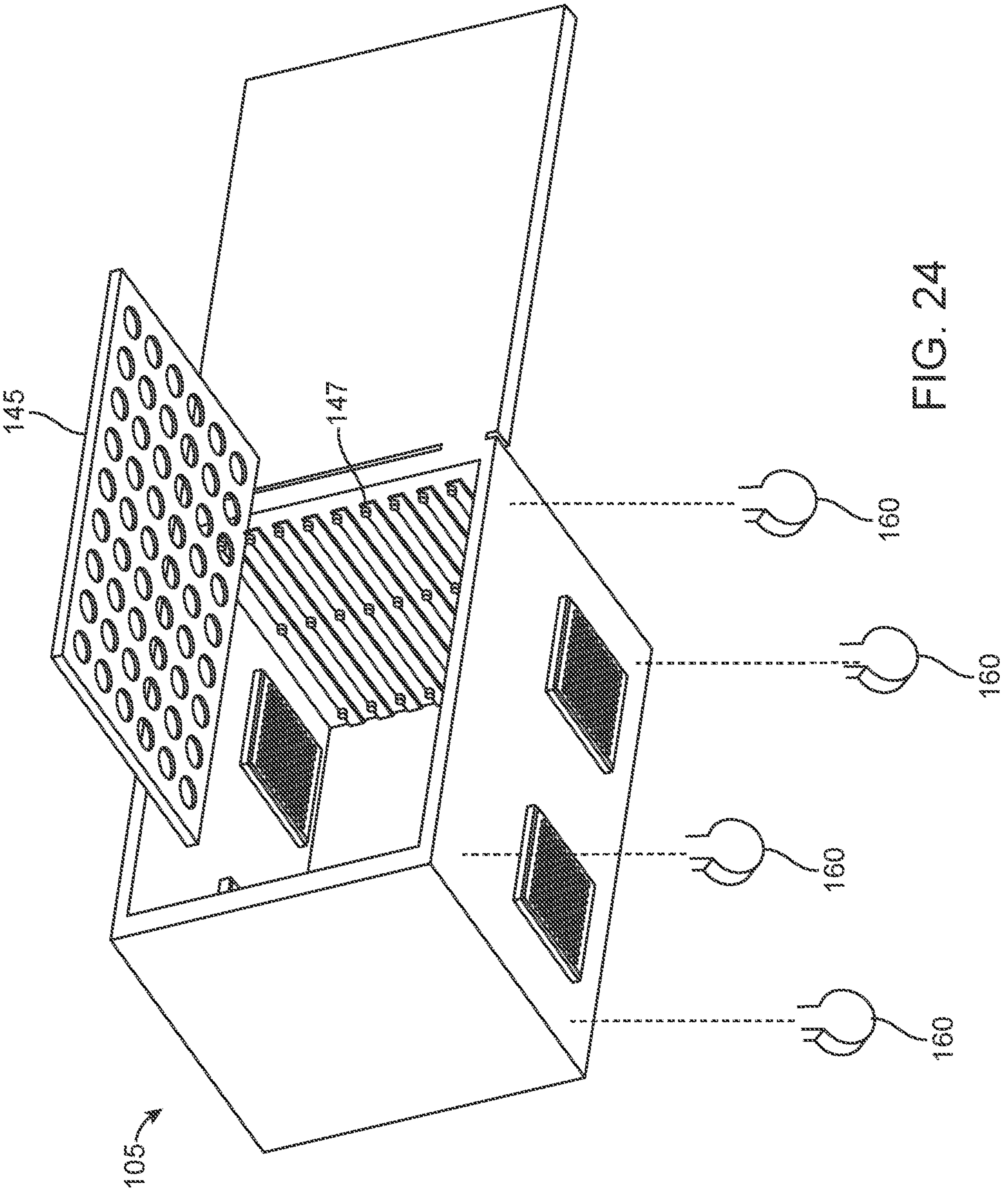

Alternatively, and looking now at FIG. 24, shelving supports 147 may be bolted to cabinet 105 so as to support shelves 145.

Figures 25A, 25B:
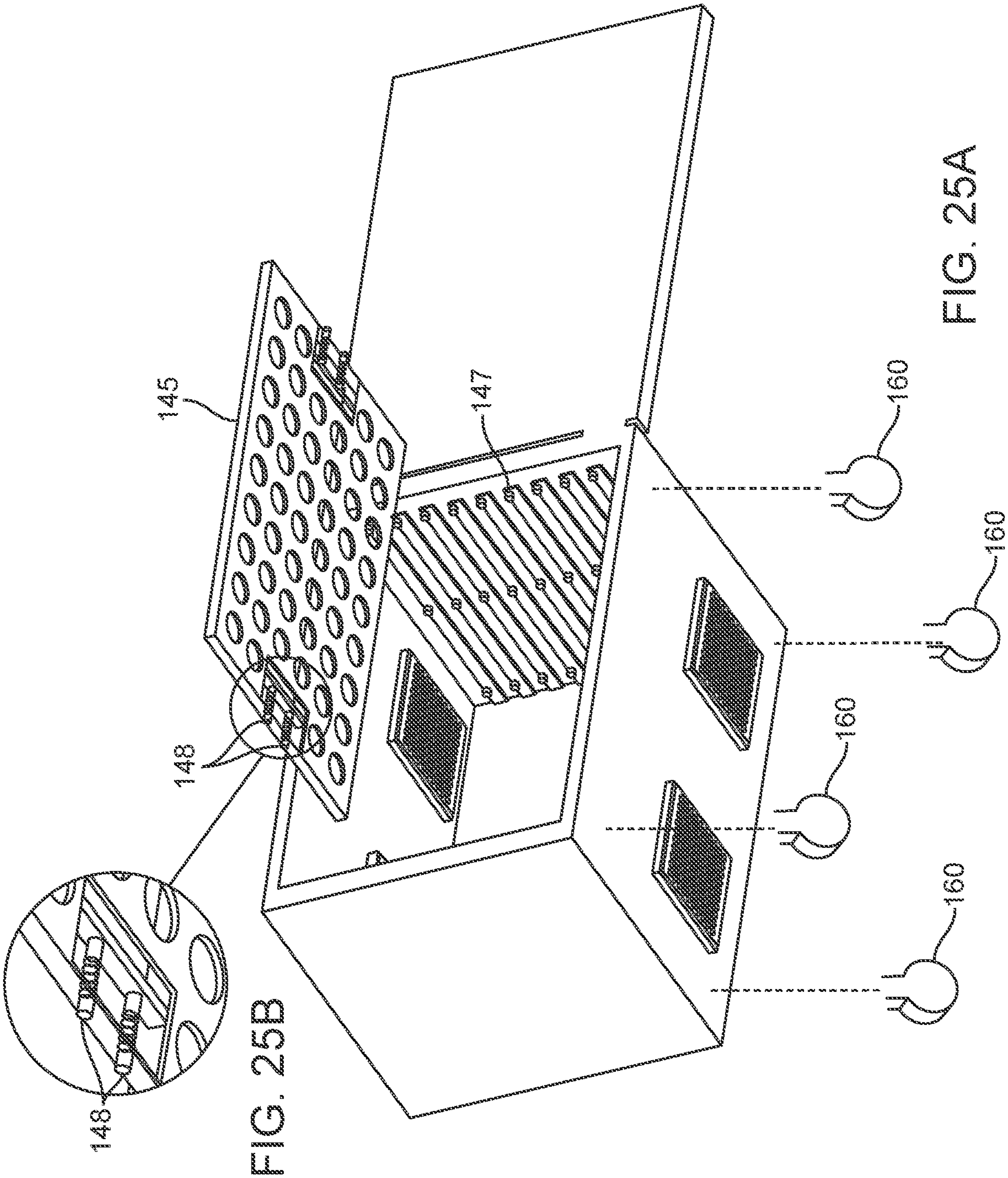

In still another aspect of the invention, and looking now at FIGS. 25A and 25B, shelves 145 may be attached to shelving supports 147 by spring-loaded pegs 148.

In another embodiment, drawer-style shelves may also be used (not shown). In addition, the shelves may be constructed of various materials which may aid in the sterilization process and/or provide other advantages (e.g., the shelves may be formed of aluminum for better heat transfer, or may be formed of materials that are less expensive, etc.).

In another embodiment, the present invention provides a sterilization cabinet which has the ability to isolate smaller areas inside of the sterilization cabinet.

Figure 26:
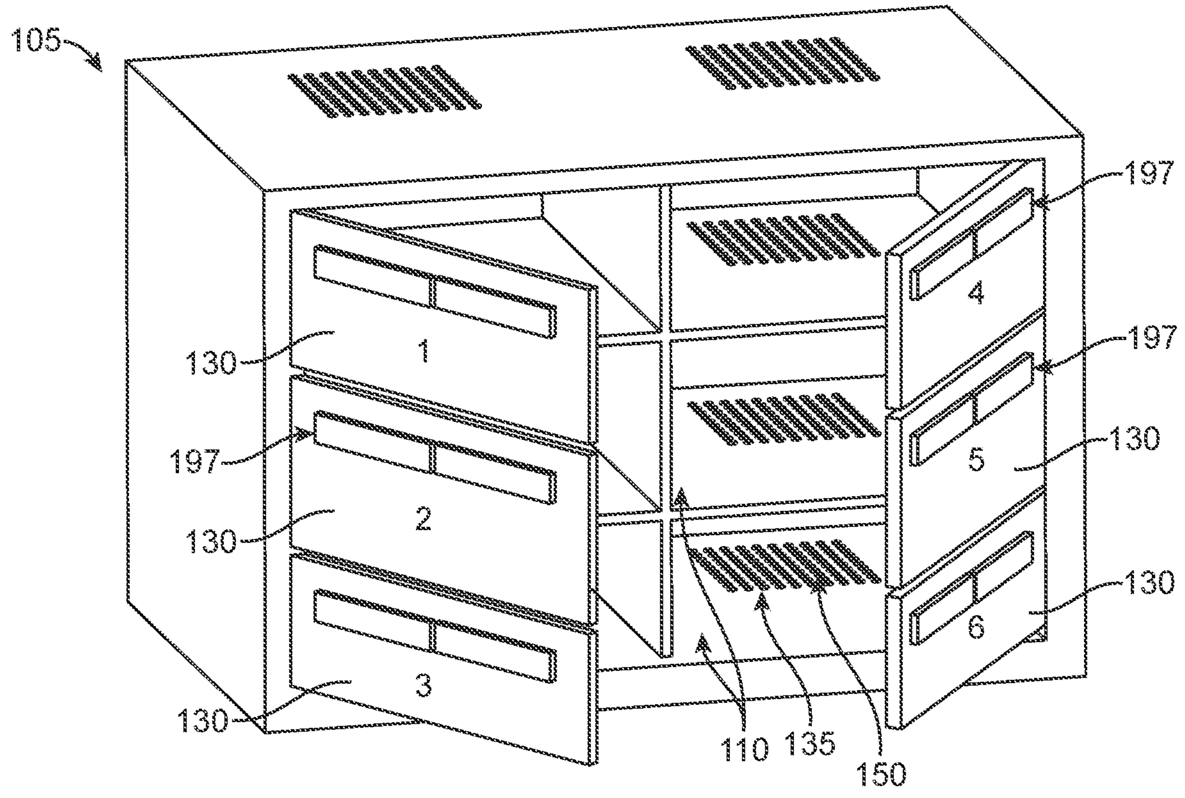
FIG. 26 is a schematic view showing a novel sterilization cabinet formed with multiple internal sterilization chambers.

More particularly, and looking now at FIG. 26, sterilization cabinet 105 is configured so as to provide multiple chambers 110 within cabinet 105. More particularly, in this form of the invention, sterilization cabinet 105 comprises separate individual chambers 110, each of which are accessible by a separate door 130. Preferably, each chamber 110 is provided with its own vent 135 and filter 150 to allow for steam or heat penetration during the sterilization process. In addition, each individual chamber 110 may have a sterile/unsterile indicator 197 (of the same or a similar type as will be described in greater detail below) to indicate the sterile/non-sterile condition of that compartment.

Compartmentalization provides the option of the contents of the several chambers 110 being used in different procedures. In other words, all chambers 110 and their contents can be sterilized at the same time, and then the contents of individual chambers 110 can be used without compromising the sterility of the other chambers 110 or their contents. By way of example but not limitation, four trays (placed in one or more chambers 110) can be brought to an operating room for a "4 tray procedure" (i.e., a medical procedure requiring those four trays of sterilized medical instruments), and another eight trays placed in a separate set of chambers within the same sterilization cabinet 105 can be brought to a second operating room for an "8 tray procedure" (i.e., a medical procedure requiring those eight trays of sterilized medical instruments). Compartmentalized sterilization cabinet 105, in combination with transfer cart 200, can thus serve as a delivery system for more than one medical procedure, providing several efficiencies including, but not limited to, requiring fewer staff to deliver the sterile trays and requiring less equipment to deliver the trays to the desired location.

In addition to the foregoing, sterilization cabinet 105 may be provided with additional features for assisting in the determination of the completion of the sterile processing or for providing additional information about the status of the cabinet (e.g., whether the sterilization cabinet is too hot to open).

By way of example but not limitation, such additional features may include indicators on the windows or panels of the cabinet that change color after sterile processing of the cabinet and then change back after the cabinet is opened (and hence rendered non-sterile).

Figure 27:
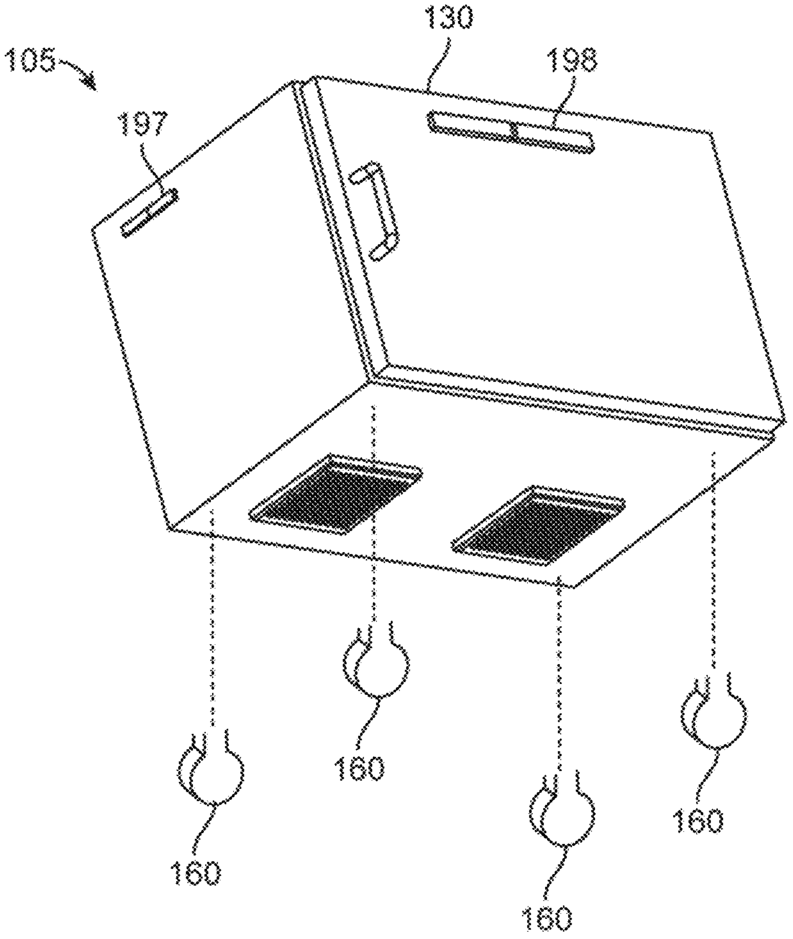
FIG. 27 is a schematic view showing a status indicator feature of the sterilization cabinet of the present invention.

In addition, and looking now at FIG. 27, an external indicator 197 positioned on the cabinet itself may indicate when the cabinet is too hot to touch (e.g., by "lighting up" or otherwise making the "hot" indicator more visually prominent than the "cold" indicator) and/or making the "hot" indicator less visually apparent when the cabinet has reached appropriate handling temperature. Similarly, another indicator 198 may indicate whether the door 130 of the cabinet has been opened (e.g., by "lighting up" or otherwise making the "UNSTERILE" indicator more visually prominent than the "STERILE" indicator). The indicators may also provide other information to a user in the manner described above (e.g., whether the door 130 has been "OPENED" or has remained "CLOSED").

Sterilization Cabinet Sizing and Configurations

Sterilization cabinet 105 can be fabricated in many sizes including, but not limited to, sterilization cabinets that can be specifically sized to receive four trays, or eight trays, or nine trays, or twelve trays, etc.

Figure 28:
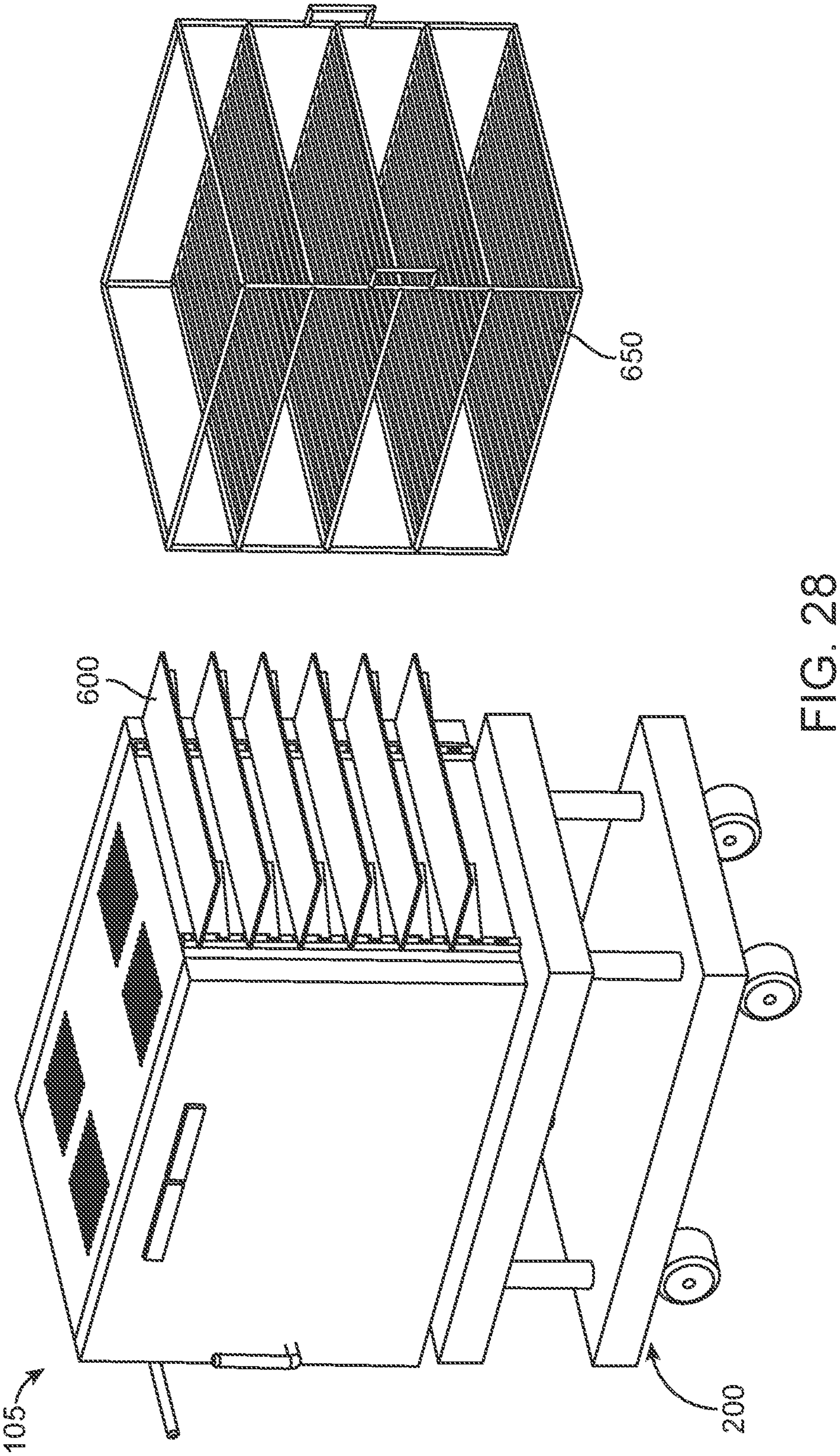
FIG. 28 is a schematic view showing a mobile sterilization system comprising external shelving.
Figures 29A, 29B, 29C, 29D:
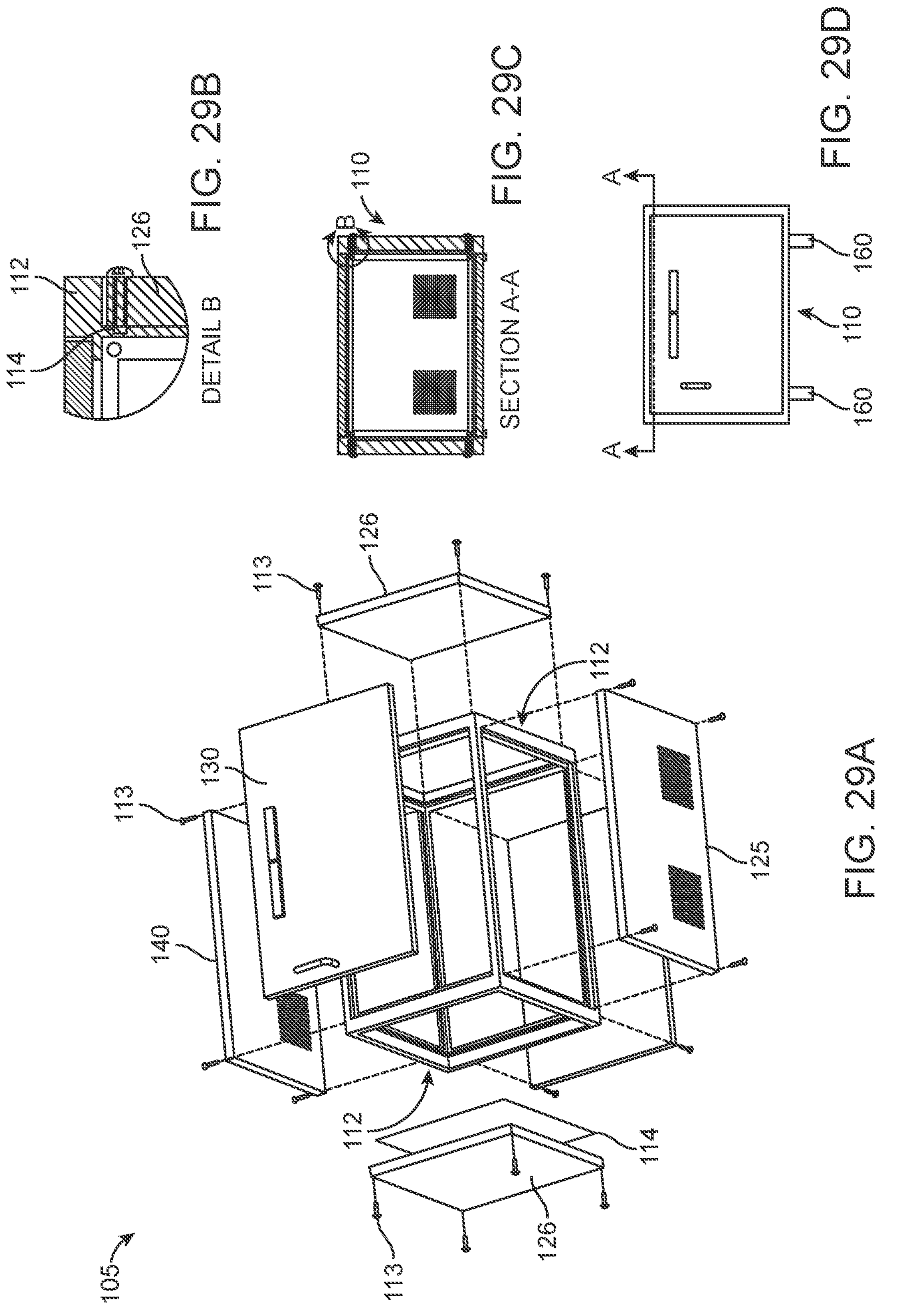
FIGS. 29A-D and 30A-D are exploded schematic views of a novel sterilization cabinet formed in accordance with the present invention.
Figure 30B:
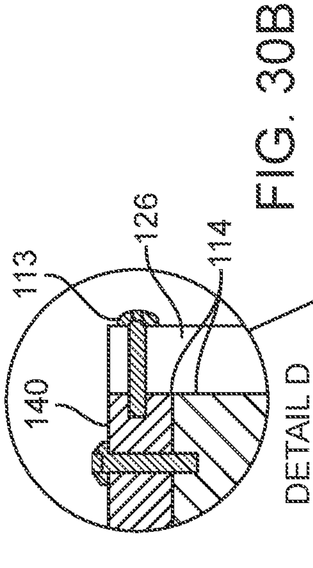
Figure 30C:
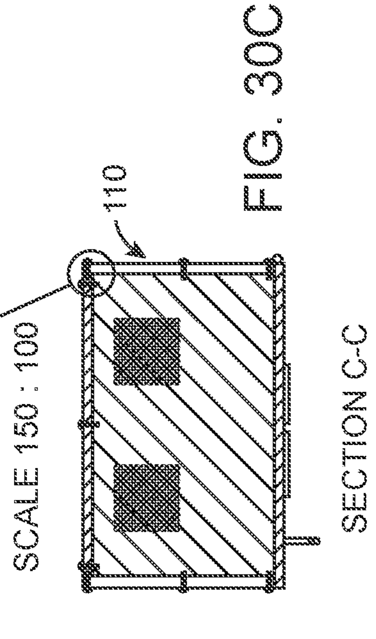
Figure 30D:
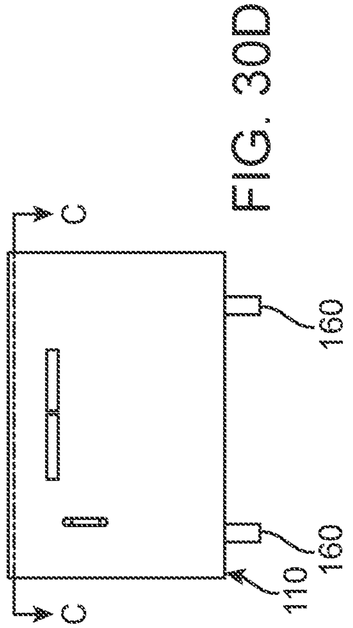
Figure 30A:
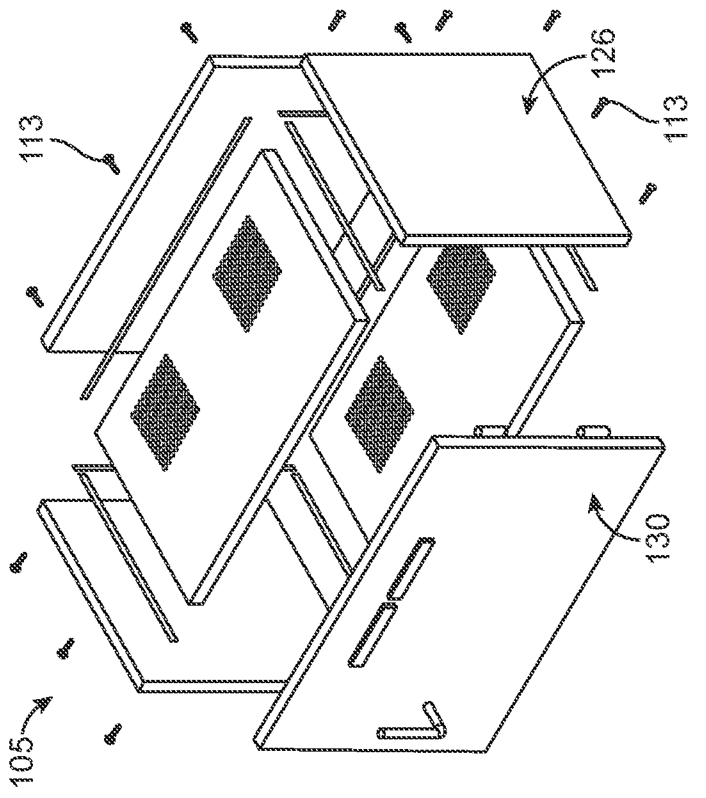
Figure 30E:
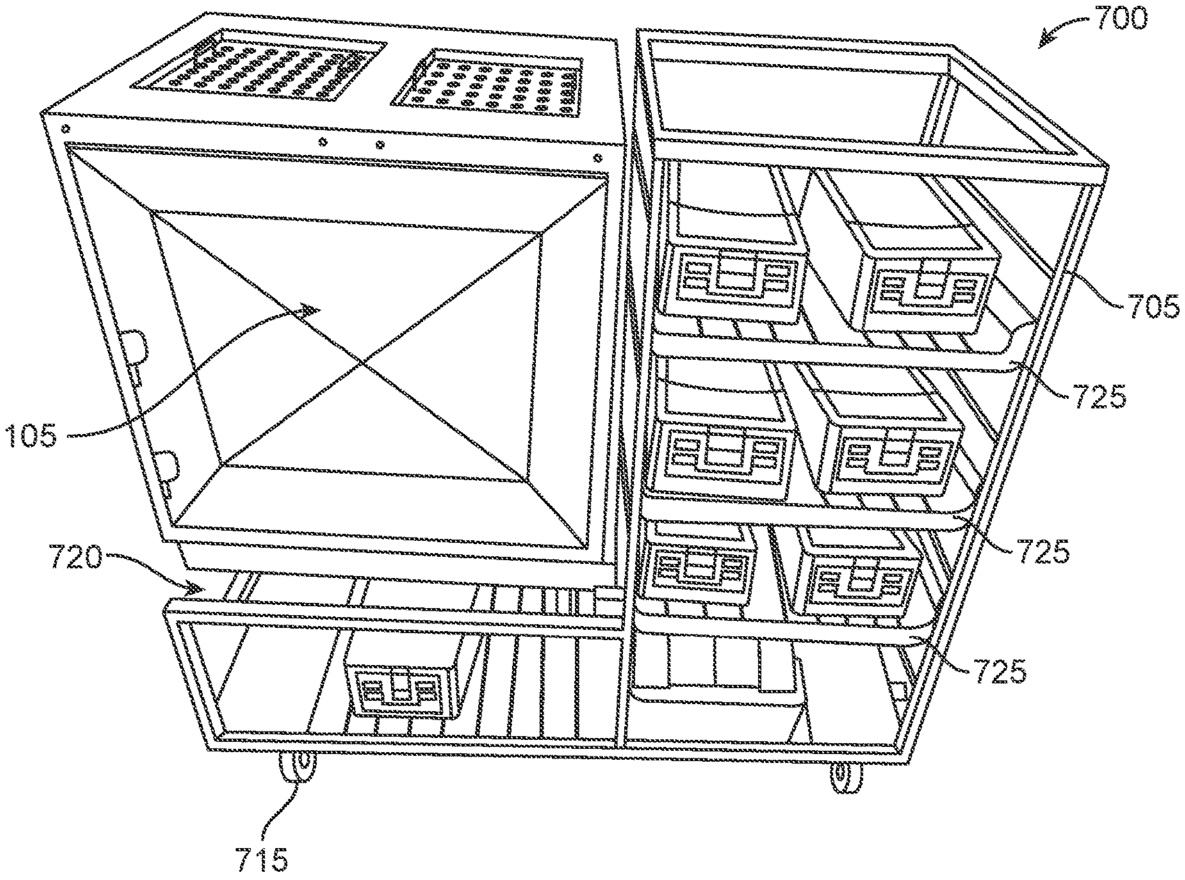
FIG. 30E is a schematic view of a novel docking station formed in accordance with the present invention.
Figure 31:
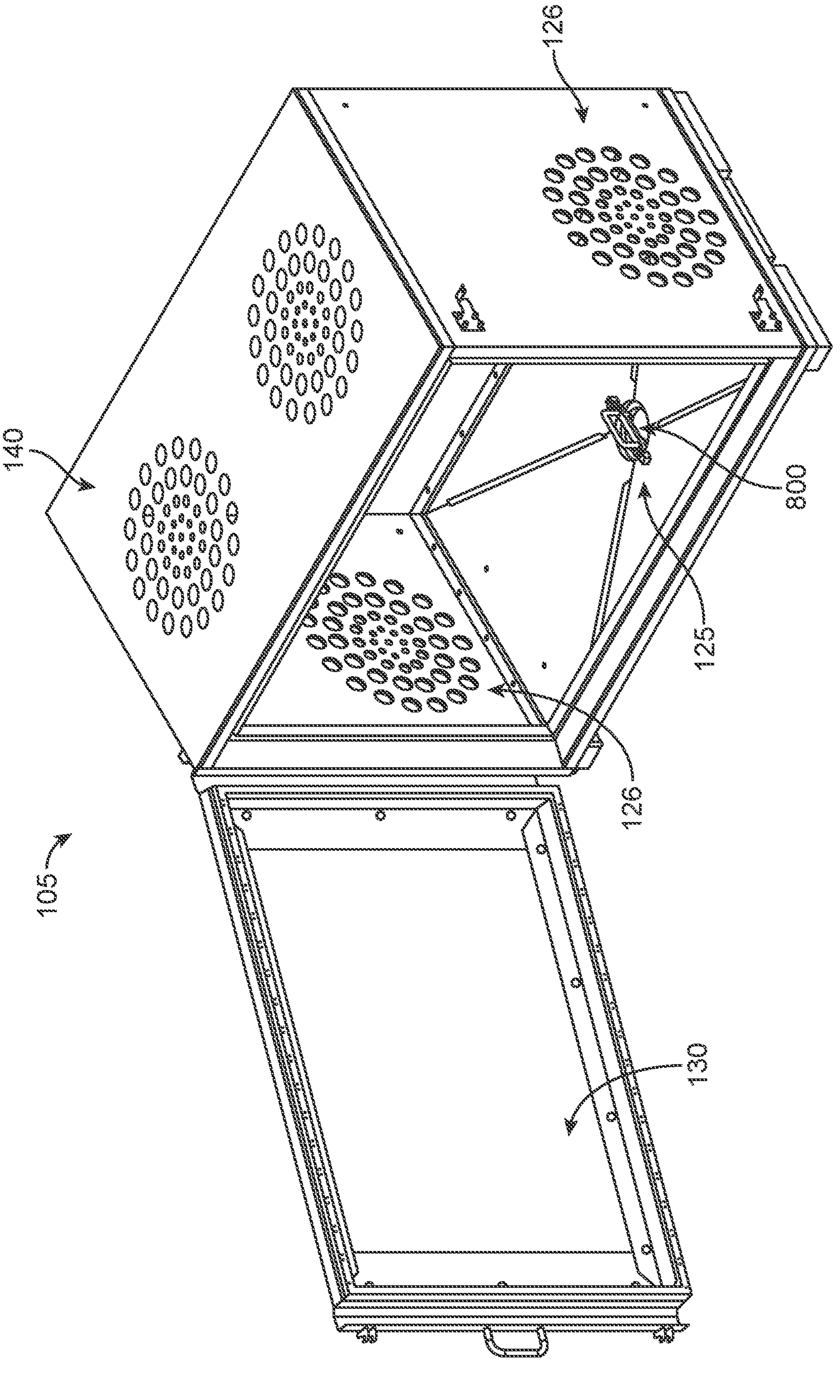
FIGS. 31-41 are photographs of an improved drain and filter assembly for the sterilization cabinet of the present invention.
Figure 32:
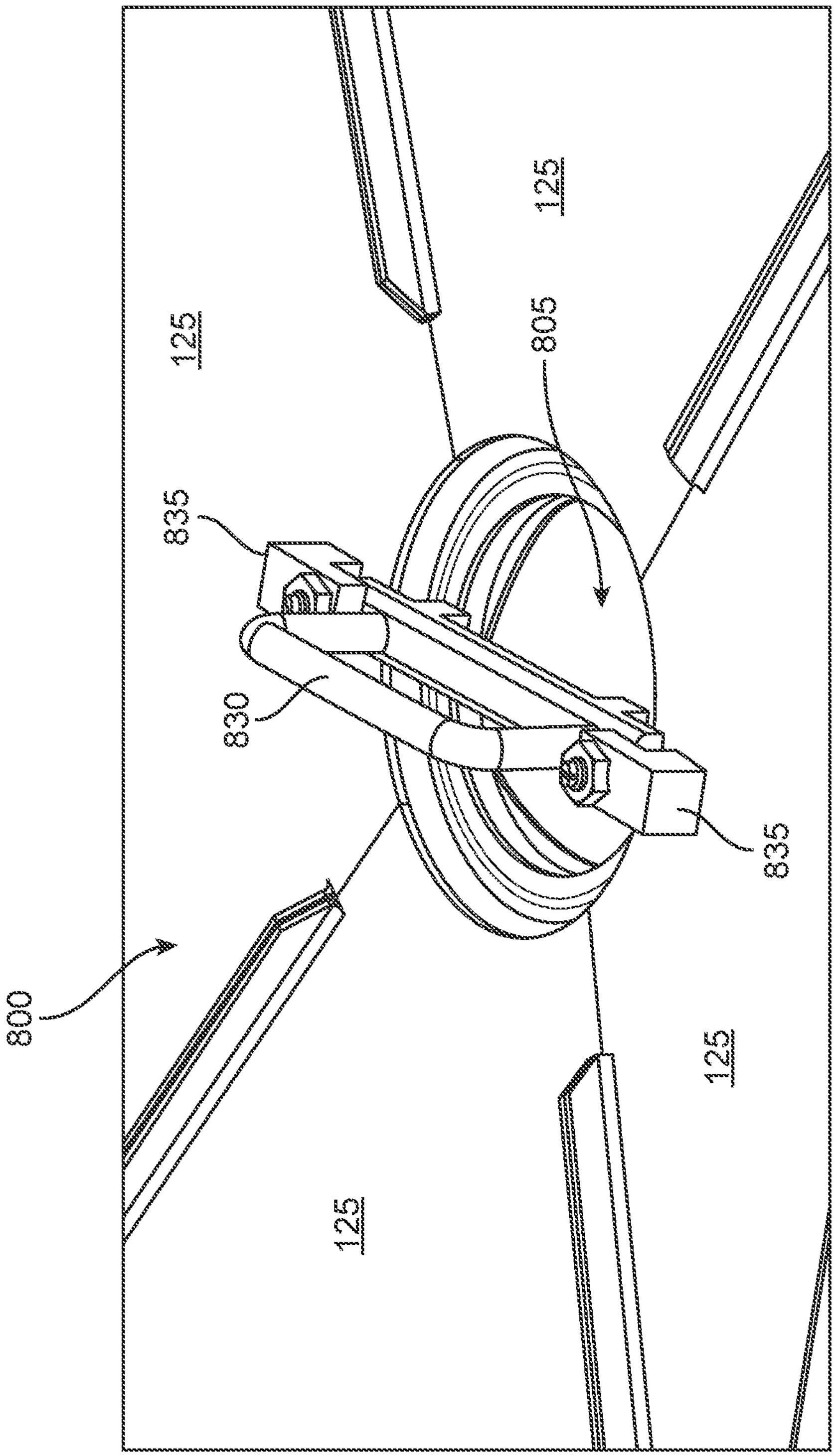
Figure 33:
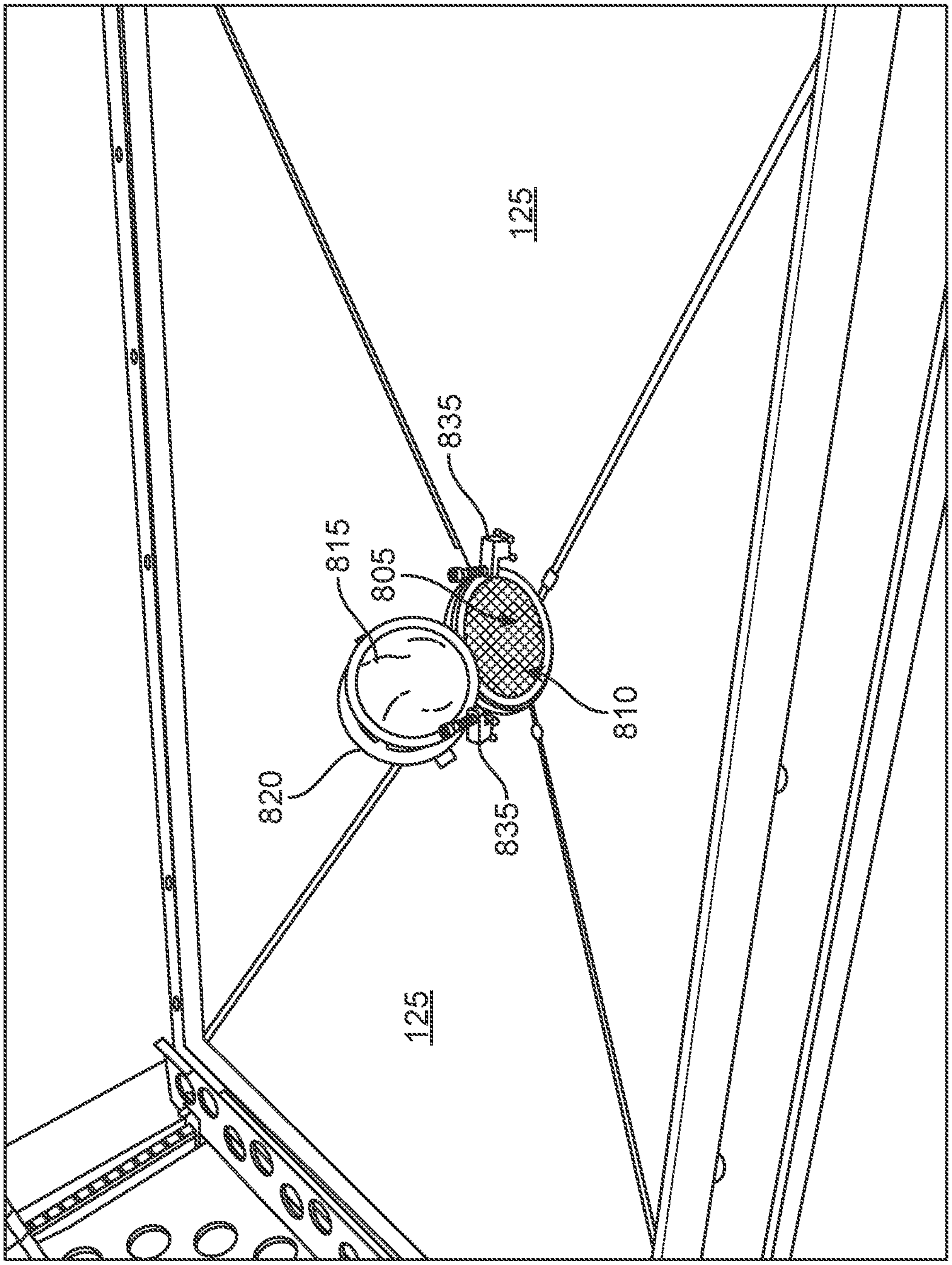
Figure 34:
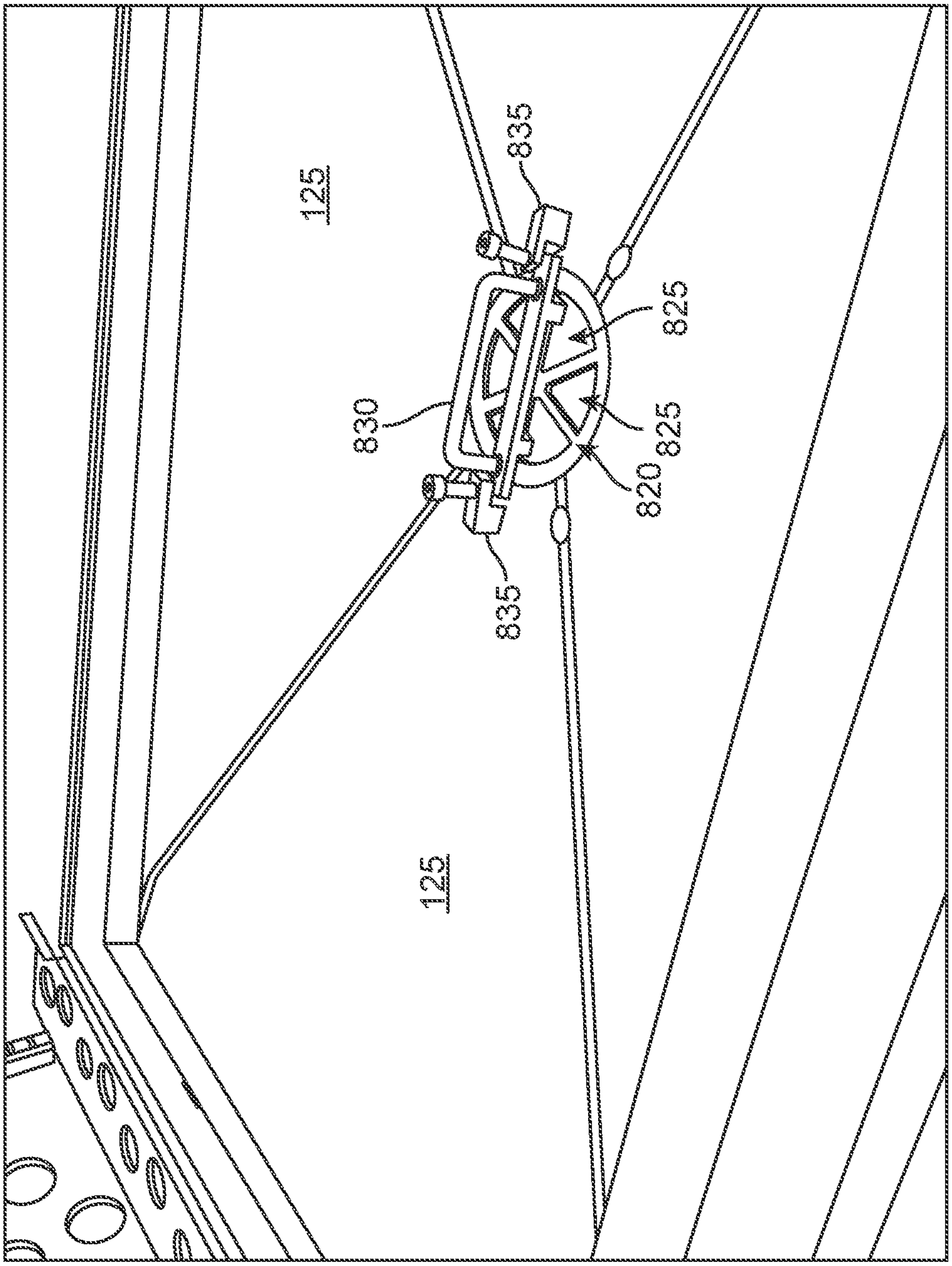
Figure 35:
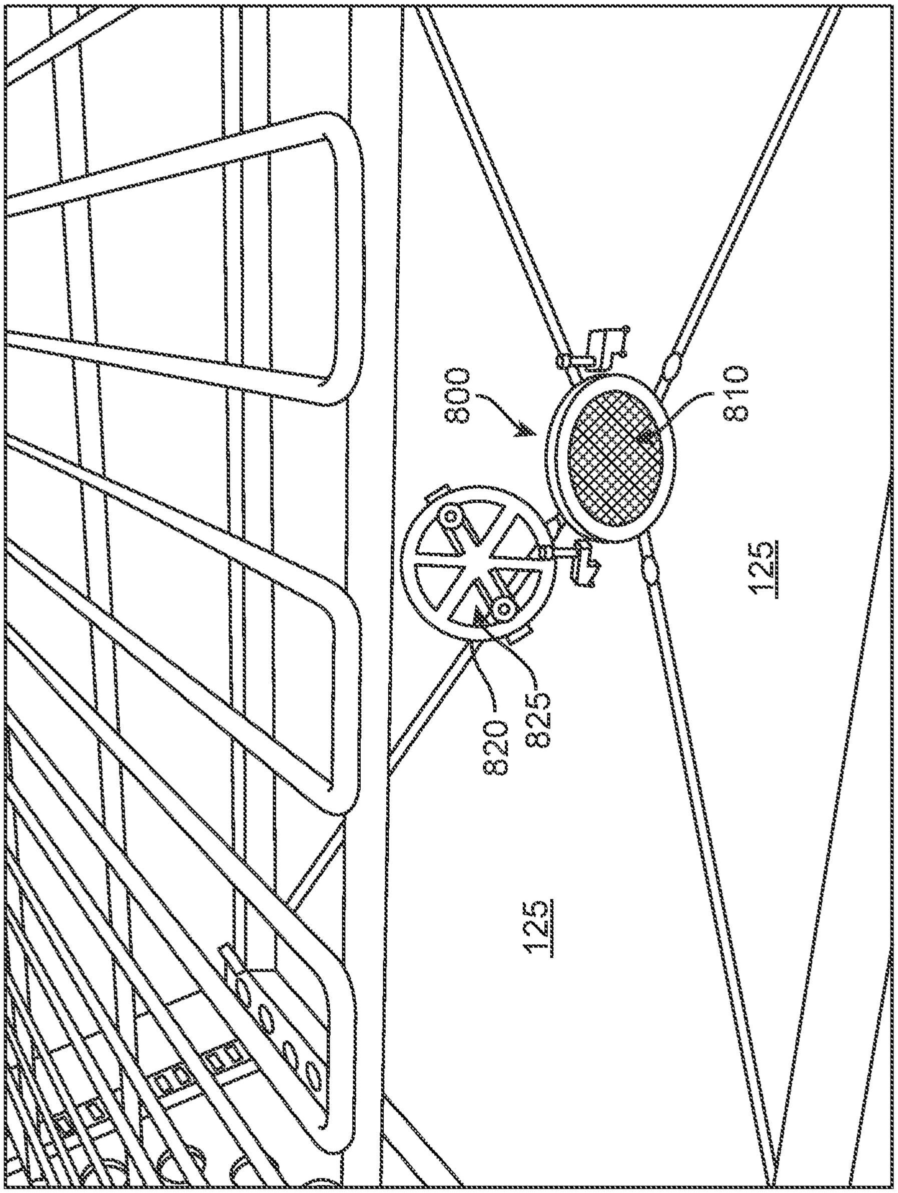
Figure 36:
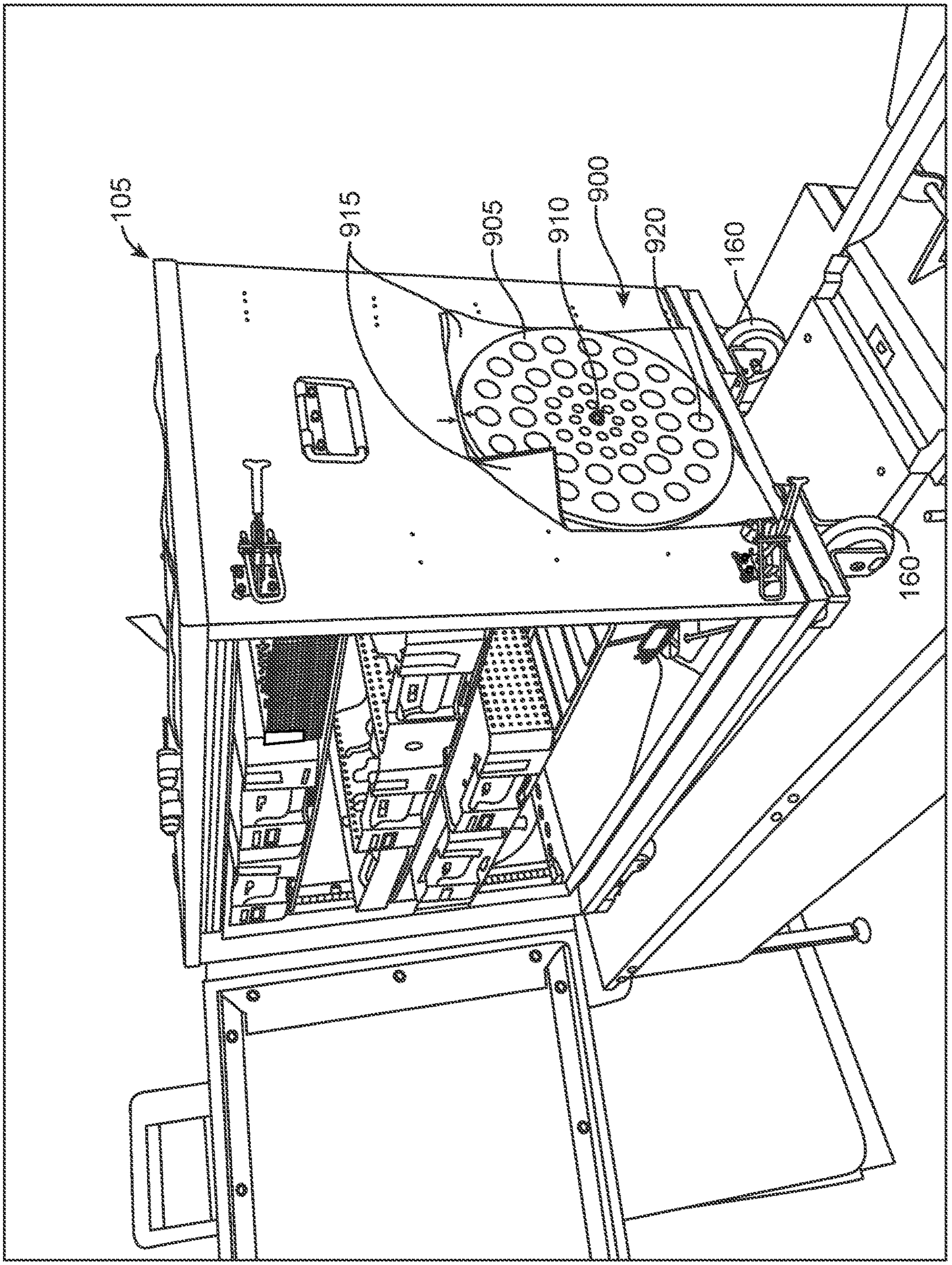
Figure 37:
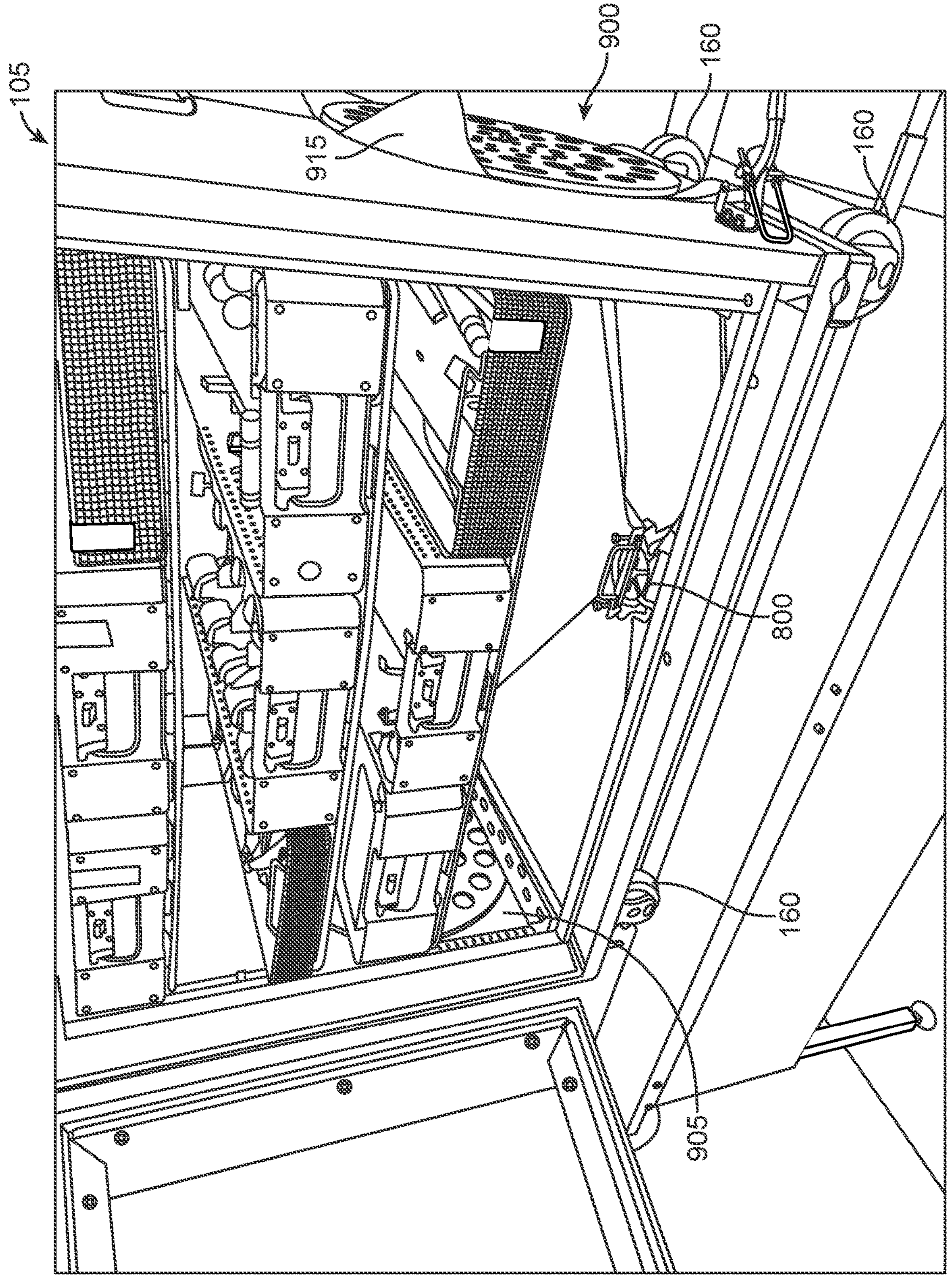
Figure 38:
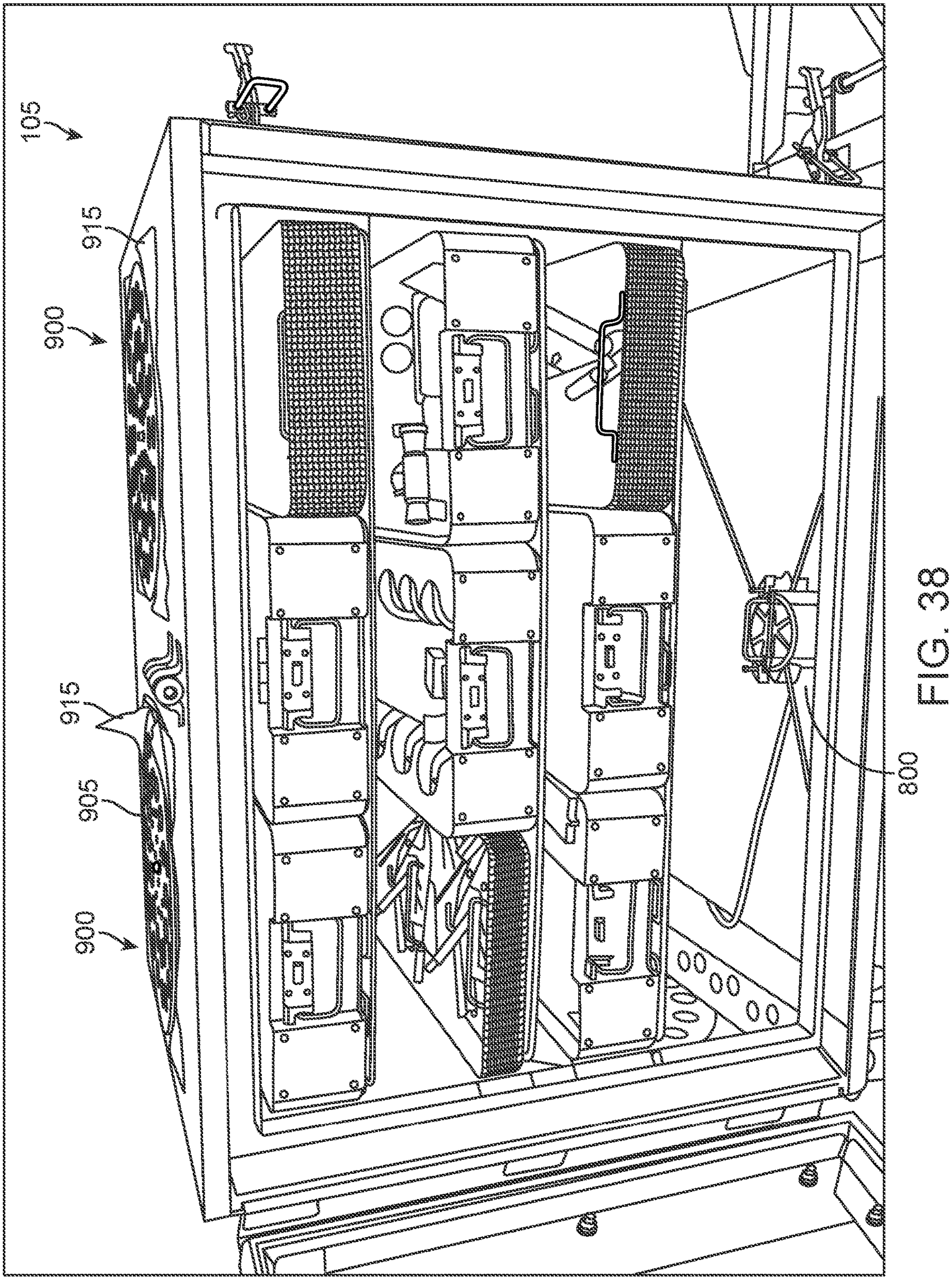
Figure 39:
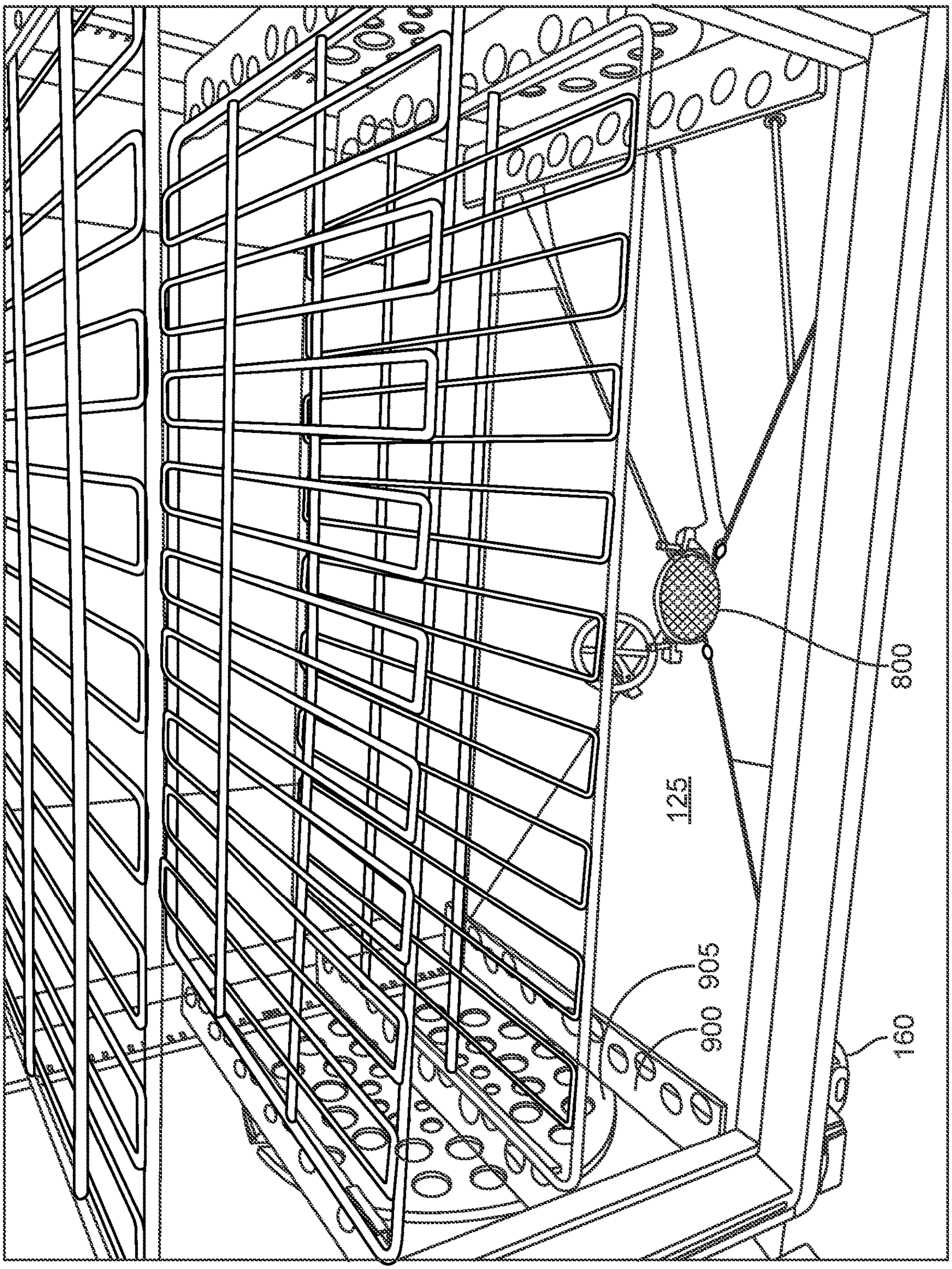
Figure 40:
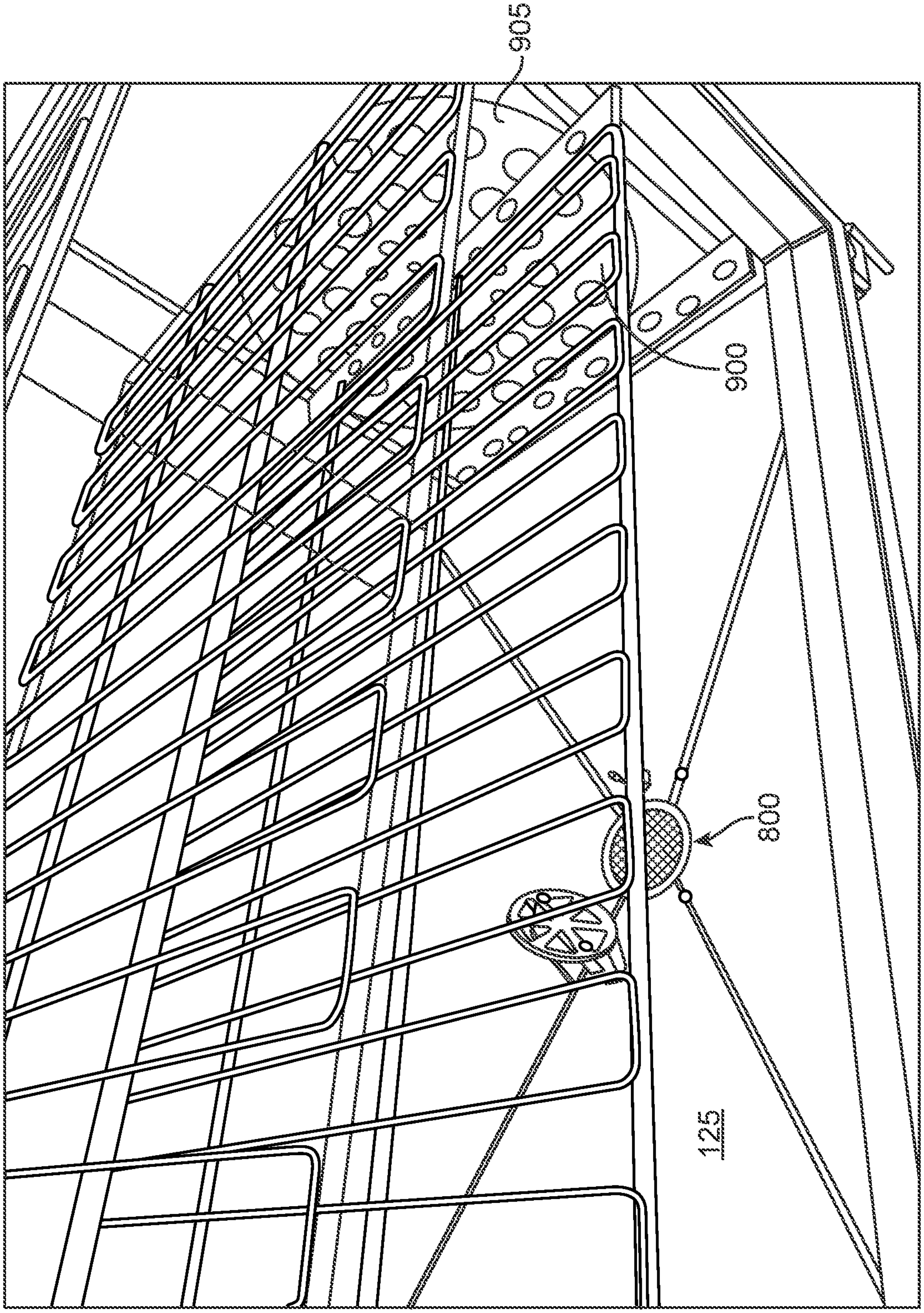
Figure 41:
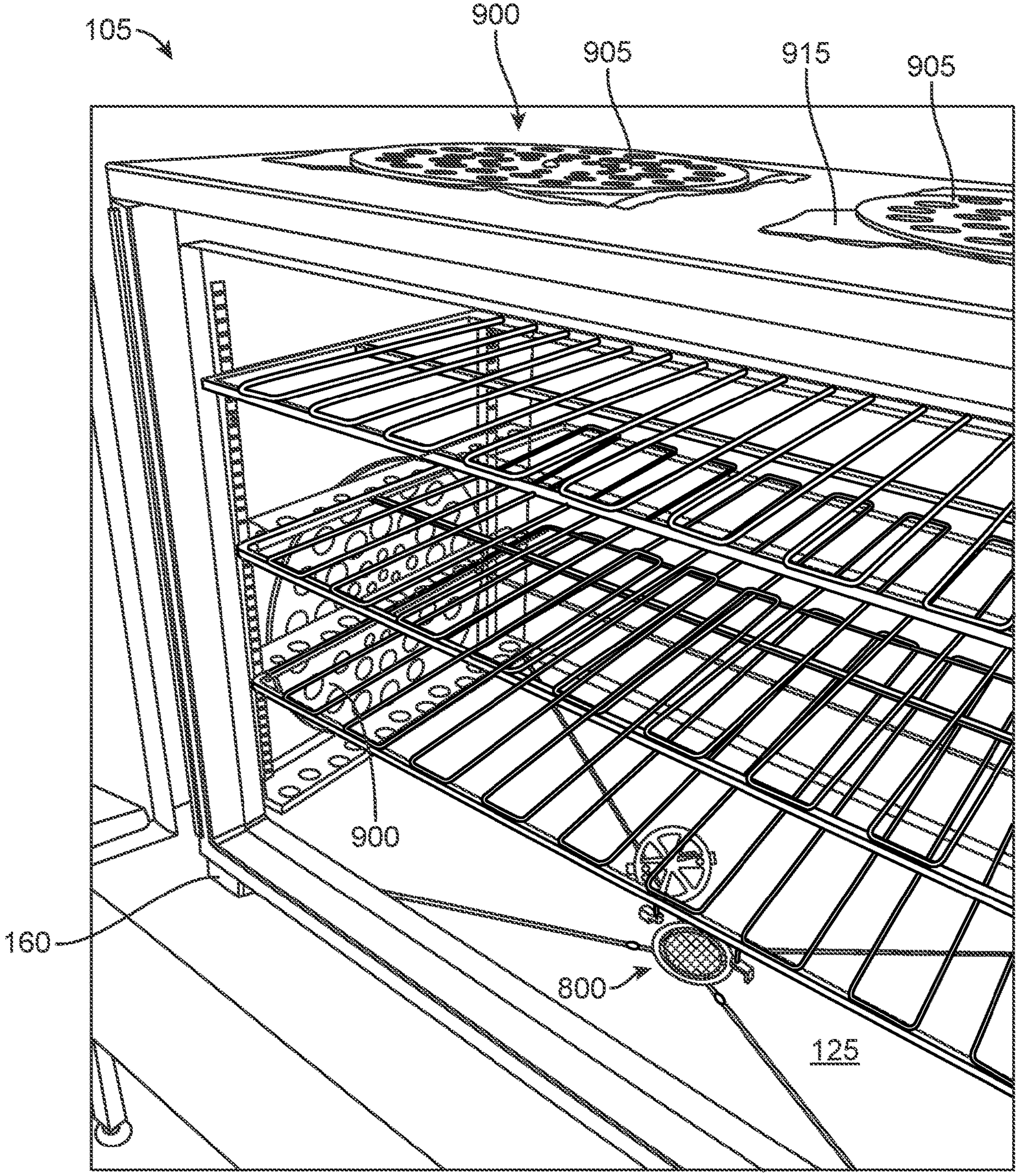
Figure 42:
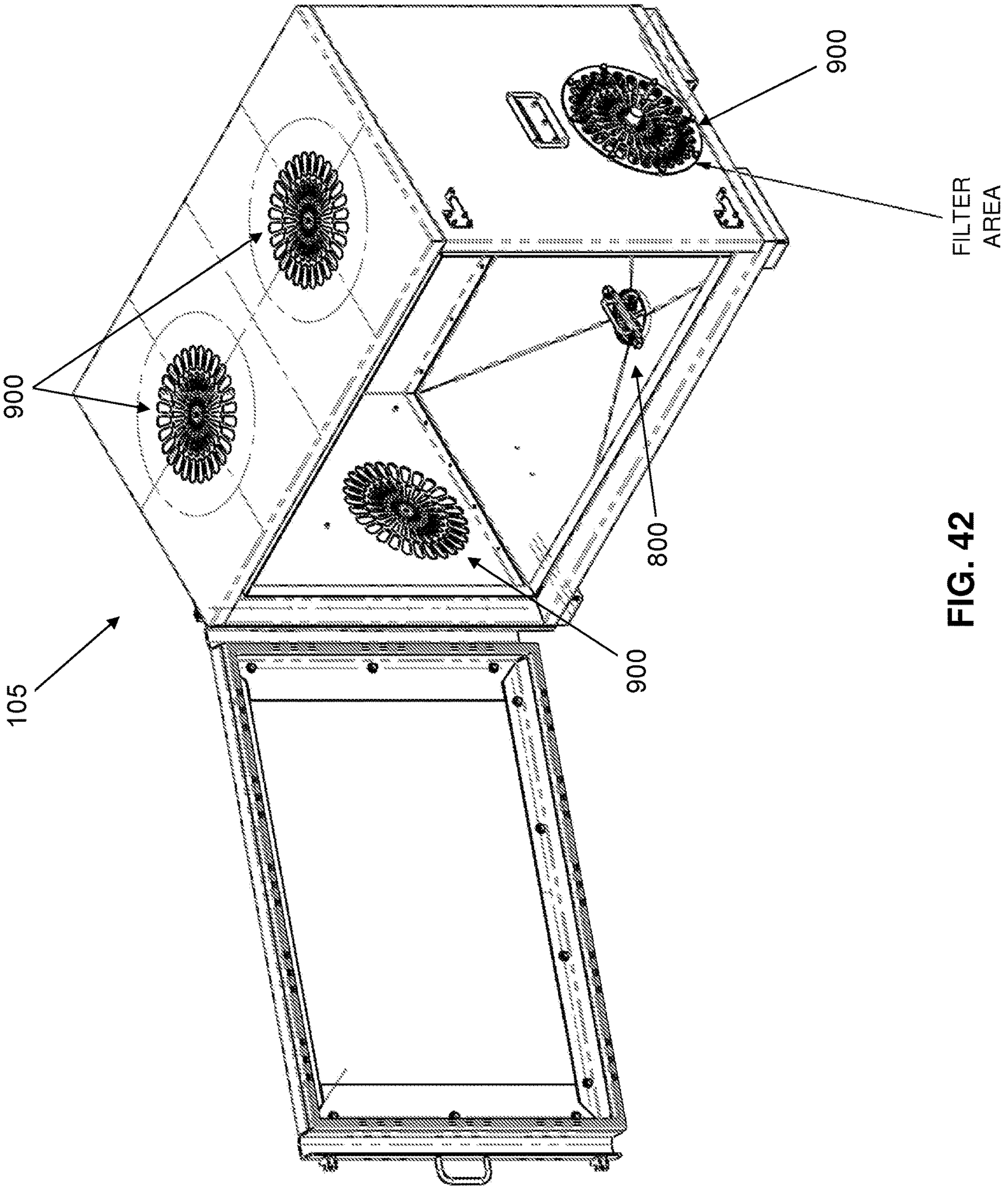
FIGS. 42-45 are schematic views of the improved drain and filter assembly of FIGS. 31-41.
Figure 43:
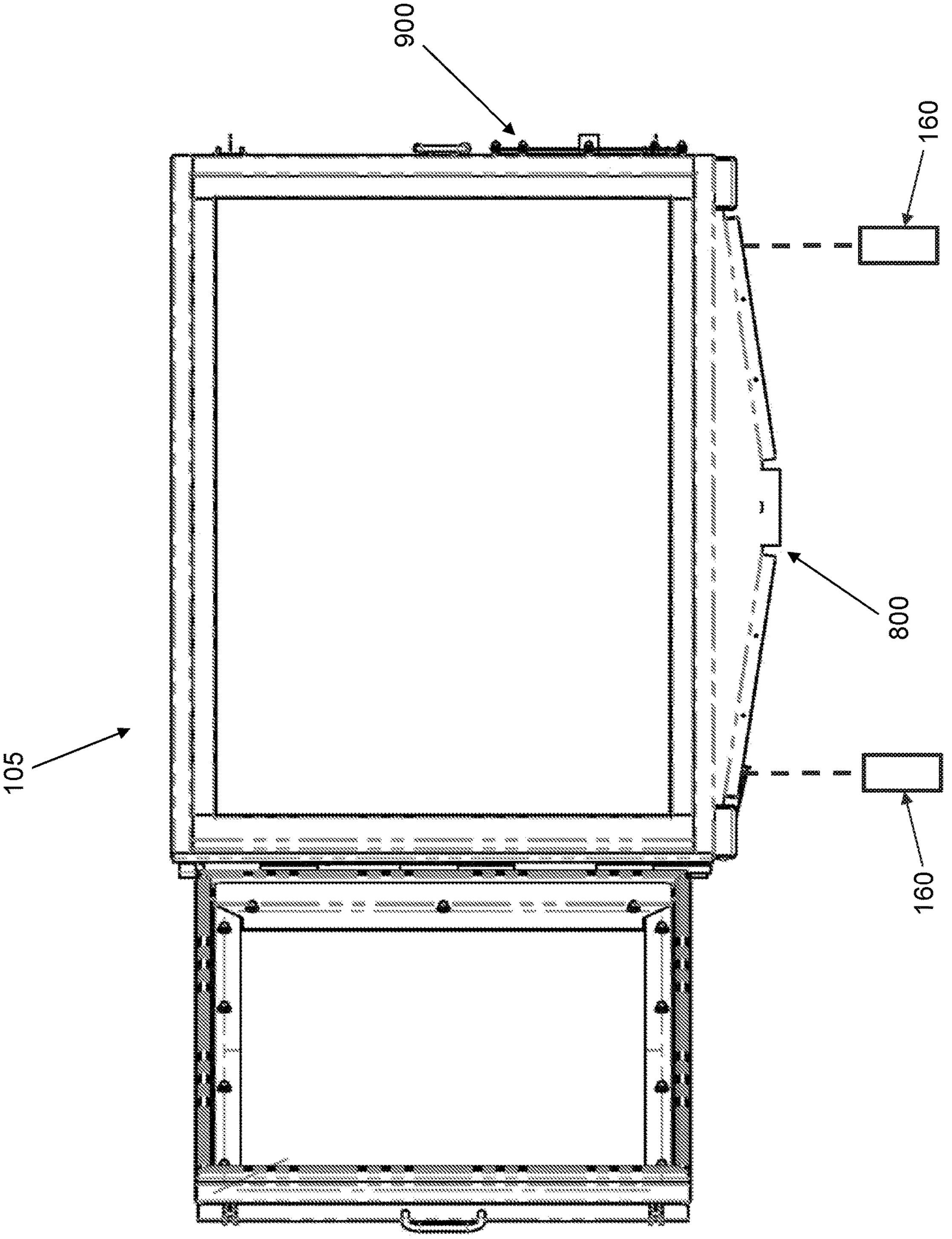
Figure 44:
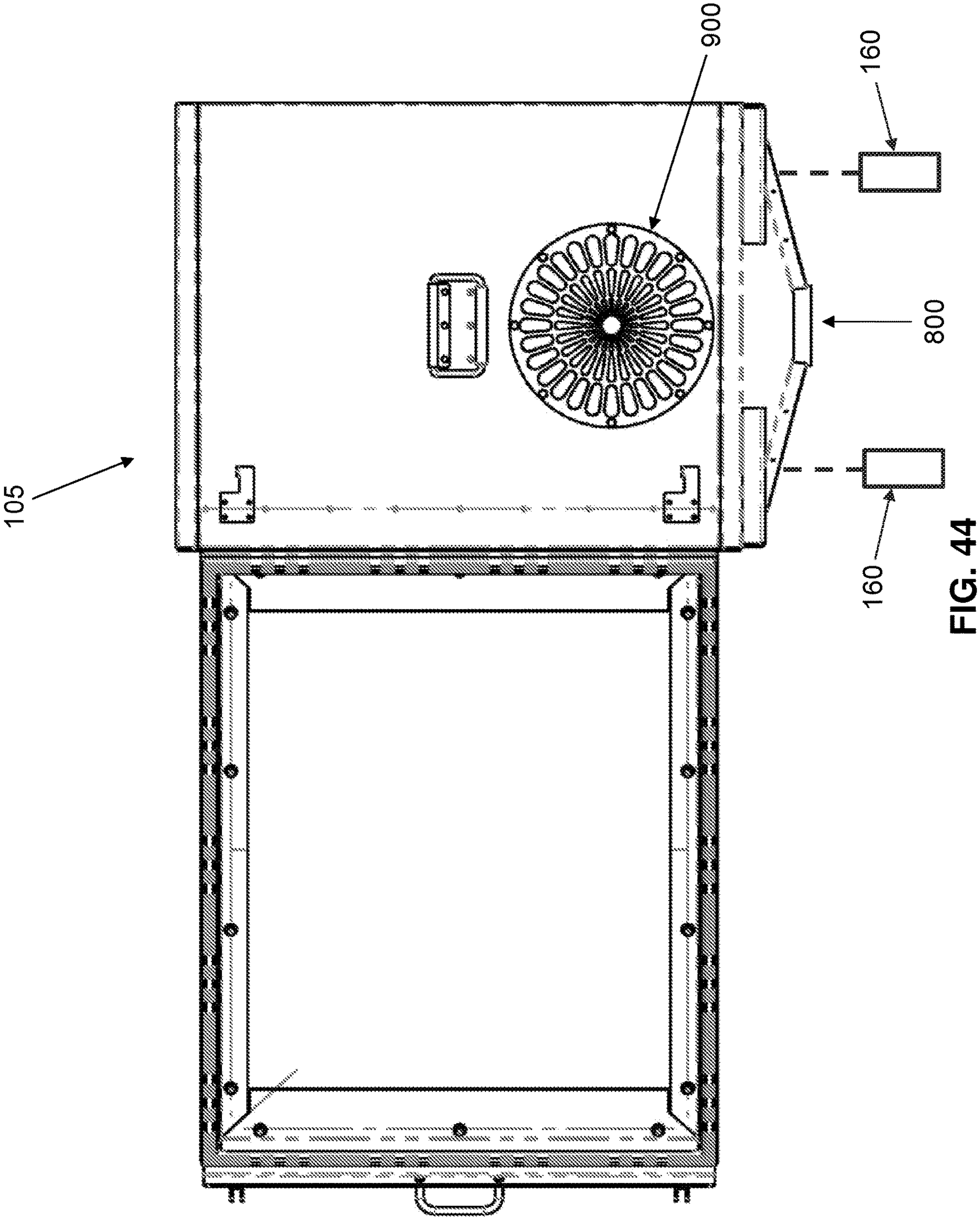
Figure 45:
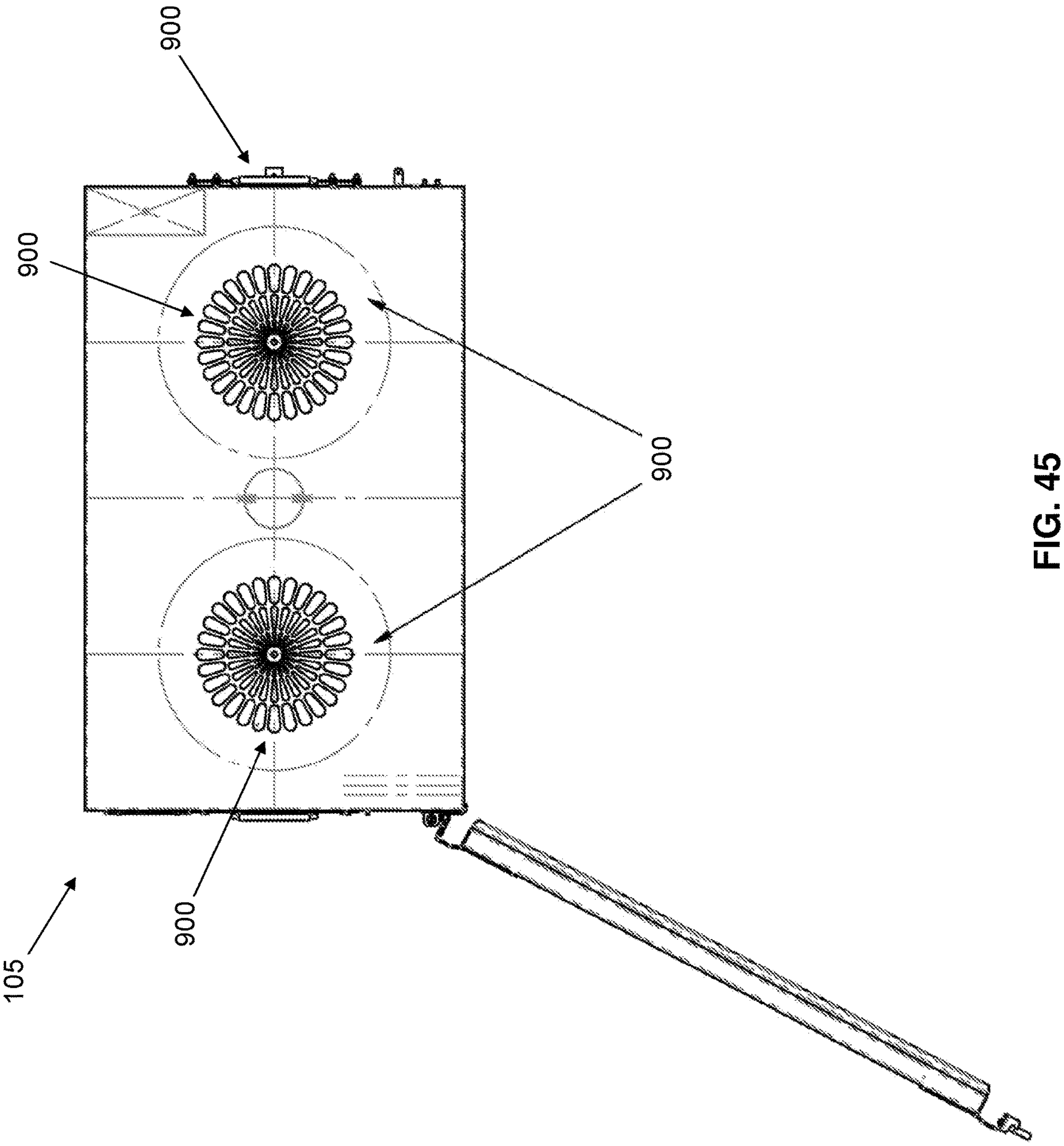

Furthermore, and looking now at FIG. 28, each size cabinet can also be manufactured with separate external shelving 600 positioned on the exterior of one or more side walls 126 for maximizing space usage (e.g., in the autoclave chamber for each cycle in the autoclave). External shelving 600 can accommodate additional trays of wrapped instruments or rigid containers and is attachable to cabinet 105 for easy unloading when the cycle is completed. External shelves 600 may be individually mounted to the outside of cabinet 105 (as in the case of external shelving 600). Alternatively, the external shelves can take the form of a rack 650 which can be removably attached (e.g., clipped to) a side wall 126 of sterilization cabinet 105. Each shelving unit may come with its own transfer cart according to the size needed, and all shelves may be compactible or foldable for easy storage when not in use.

In additional variations, instruments or medical devices in wraps, other rigid containers, or peel pouch sterilization bags can be positioned in the units described herein. Instruments or instrument trays can be wrapped, containerized, or sealed within a peel pouch (with an indicator inside as currently performed) and then placed in the unit to be sterilized. The sterilization unit 100 can include multiple sizes of wraps, containers or peel pouches/bags. In one variation, a single peel pouch/bag can contain an entire tray. In variations where the medical devices are containerized or wrapped the container or wrapping allows the devices to remain sterile after the sterilization cabinet 100 is opened since the wrap, bag, or container provides another sterile barrier for those wrapped medical items/trays. This allows the unit 100 to sterilize items for more than one specific medical procedure. The wrapped/containerized instruments or trays can be brought to another room or used for the next procedure in that same room. In another example, a user could peel pouch six trays and leave an additional 6 trays unwrapped in the sterilization unit 100. The unwrapped trays can be used on the first case when the unit is opened, and the peel pouch trays can remain in the unit 100 for a different room or for the 2nd case in the same room. The user could simply close the unit 100 and transport it to the next room or close it and park it outside the O.R. on the clean side for the second case. In another example, a surgeon may know ahead of time that only certain trays are absolutely necessary. Those trays will be sterilized in the cube unwrapped, while additional trays may be used based upon findings only after the procedure has begun. Rather than setting the sterile back table with excessive quantities of trays, if the "just in case" trays are wrapped they can be safely stored beyond the sterile field and only brought into the sterile field and unwrapped when determined to be needed during the case. In another variation, a user could wrap all trays within the unit 100 and the unit 100 could still be used as a safety method for transporting the trays, knowing it provides another sterile barrier. Such a feature can be useful for offsite sterilization.

Construction Materials

Sterilization cabinet 105 has many options with respect to the raw materials for cabinet production. In one preferred form of the invention, sterilization cabinet 105 may be manufactured out of stainless steel. However, it should be appreciated that sterilization cabinet 105 can also be manufactured out of various materials in addition to stainless steel, including but not limited to aluminum (which may allow for a lighter version of the product and the potential for multiple color options during anodizing), or a polymer.

If desired, door handle 132, deadman's safety grip 240 and any other surfaces that may be handled in order to move mobile sterilization system 100 may be covered with a disposable sanitary wrap or film in accordance with sterile procedures.

Alternative Configurations

Sterilization cabinet 105 can also be configured to be used as a "back table" during a medical procedure. More particularly, once the sterilization cabinet is opened (e.g., via either the door configurations discussed above, and/or the dome top discussed above, etc.), the shelves can be displayed to the user using a "toolbox" or "tackle box" design, swinging shelves, or movable shelf system, thereby allowing easy access to all of the inner trays.

Manufacturing Technique

Looking now at FIG. 29, there is shown an exploded diagram of an embodiment of sterilization cabinet 105 which is "bolted together" around an internal frame. More particularly, sterilization cabinet 105 may comprise a frame 112, and side walls 126, rear wall 127, top wall 140 and bottom wall 125 may be attached to frame 112 to form interior chamber 110 of cabinet 105. Each of the walls may be attached to frame 112 by bolts 113 or other suitable means. A sealant 114 or O-ring type seal (not shown) may be placed at the interface of frame 112 and between each of the walls so as to ensure an air-tight seal.

In another embodiment of the present invention, and looking now at FIG. 30, each of the walls of sterilization cabinet 105 may be bolted together without a frame. In this embodiment, each of the side, back, top and bottom panels are attached to one another with bolts 113, with a layer of sealant 114 being applied to the interface between each of the panels.

The embodiments of the invention shown in FIGS. 29 and 30 may provide additional advantages including, but not limited to, reduced shipping costs, inasmuch as the disassembled sterilization cabinet could be shipped in a smaller shipping container (e.g., with the top, bottom, side and back panels and door(s) lying flat against one another). The sterilization cabinet can then be assembled on-site by appropriately trained personnel, who could then verify proper assembly (including an air tight seal) by biological testing methods well known to those in the art.

Docking Station

Mobile sterilization system 100 may also be configured for use with an optional docking station. Looking now at FIG. 30E, docking station 700 comprises a frame 705 and wheels 715. The frame 705 provides a space 720 for receiving one or more sterilization cabinets 105. Docking station 700 preferably also comprises shelves 725 (which can receive additional sterilizable instrument containers). Docking station 700 is itself sterilizable and may be placed directly in an autoclave.

In one preferred form of the invention, transfer cart 200 and docking station 700 are configured to be releasably secured to one another. In this form of the invention, a user may bring transfer cart 200 (carrying sterilization cabinet 105) up to docking station 700 and then releasably secure transfer cart 200 to docking station 700 (or otherwise ensure that neither transfer cart 200 nor docking station 700 will move during transfer of sterilization cabinet 105 from transfer cart 200 to docking station 700); cabinet 105 may then be easily moved from transfer cart 200 onto docking station 700. Transfer cart 200 may then be detached from docking station 700 and docking station 700 (and its passenger containers) moved into the autoclave for sterilization.

Some advantages of using docking station 700 in conjunction with mobile sterilization system 100 include but are not limited to: (i) more efficient use of autoclave space inasmuch as the sterilization cabinet 105 may be placed on docking station 700 which is also loaded with additional containers requiring sterilization; and (ii) freeing up transfer cart 200 for other uses after sterilization cabinet 105 is transferred from transfer cart 200 to docking station 700.

In this respect it should be noted that, in some forms of the invention, transfer cart 200 is not intended to be sterilizable (e.g., where transfer cart 200 carries heat- and moisture-sensitive components such as electronics, etc.).

Improved Condensation Drain and Filter Ports

In still another form of the present invention, an improved condensation drain and filter port is provided for significantly enhancing the performance of sterilization cabinet 105.

More particularly, it has been discovered that the removal of condensate from a sterilization cabinet in its liquid form (as opposed to by evaporation) significantly enhances the performance of a sterilization cabinet. It has been found that steam used during the sterilization process generates a substantial amount of condensate (i.e., liquid water) during the sterilization process. The condensate flows by gravity to the lowest point of the sterilization cabinet. During the drying phase of the sterilization process, a vacuum acts on the autoclave chamber. As the pressure of sterilization cabinet is equalizing with that of the autoclave, the condensation is pulled through a drain (more particularly described below) disposed at the lowest point of the sterilization cabinet and out of sterilization cabinet.

More particularly, in another preferred embodiment of the invention, and looking now at FIGS. 31-45, there is provided an improved drain 800 configured to allow condensate to escape sterilization cabinet 105 without compromising its sterility. Drain 800 is disposed at the lowest point in bottom wall 125 of sterilization cabinet 105. Preferably, sterilization cabinet 105 comprises a pitched floor so that any condensate is directed by gravity to the lowest point in bottom wall 125.

Drain 800 comprises a recess 805 formed below the lowest point in bottom wall 125 of sterilization cabinet 105. Configuring the drain in this manner prevents any residual moisture from remaining in cabinet 105. Recess 805 may be formed of thick stainless steel or other material so as to retain heat and enhance evaporation of any condensate that has flowed into recess 805.

Drain 800 preferably comprises a grill plate/screened floor 810 disposed over recess 805. Grill plate/screened floor 810 provides a rigid platform to support a filter (as is more particularly described below). Grill plate/screened floor 810 is permeable so as to allow condensate to pass through it. A filter 815 is disposed on top of grill plate/screened floor 810. Filter 815 is configured so as to allow condensate to pass through it and out of sterilization cabinet 105 while preventing contaminants from entering sterilization cabinet 105.

A rigid filter door 820 is disposed across recess 805 and on top of filter 815, thereby capturing filter 815 between filter door 820 and grill plate/screened floor 810. Filter door 820 comprises perforations 825 to allow condensate to pass from sterilization cabinet 105 through filter door 820. Filter door 820 is also formed with handle 830, which is held in place by handle brackets 835. Handle 830 allows a user to easily remove filter door 820 (as described below) so as to provide access to filter 815 so that filter 815 may be changed as required. Filter 815 may be changed by removing filter door 820 by twisting handle 830 out from under handle brackets 835.

One or more gaskets (not shown) may be placed against one or more sides of filter 815 (e.g., between filter door 820 and filter 815, and/or between filter 815 and grill plate/screened floor 810) so as to form a seal to prevent the passage of microbial contamination.

In addition to the foregoing, it has also been discovered that it may be advantageous to configure sterilization cabinet 105 with improved filter ports 900 (FIG. 36) disposed in the side wall 126 of sterilization cabinet 105 (in lieu of or in addition to other locations) to allow for improved steam penetration and airflow and to provide an improved vent-to-volume ratio. Filter ports 900 may be configured to be circular portals in the panels of sterilization cabinet 105. Filter ports 900 are covered with circular plates 905 so as to allow for a single point of attachment 910 (e.g., at the center of the circle) and for an even compression of filter gaskets (more particularly described below).

Filter ports 900 comprise a filter 915 and a plate 905 having perforations 920, with filter 915 and plate 905 being mounted to the outside of sterilization cabinet 105, or mounted to the inside of sterilization cabinet 105, in alignment with perforations formed in the side panels of sterilization cabinet 105. Perforations 920 allow for the passage of steam into and out of the sterilization cabinet 105. One or more filters 915 are positioned intermediate the circular plate 905 and cabinet 105 and prevent the passage of microbial contamination therethrough.

Circular plates 905 are provided with gaskets (not shown) so as to create an effective seal between plate 905 and filter 915. Plates 905 are also provided with a twist handle (not shown) which allows for plate 905 to be locked into place and for easy removal when a change of filter 915 is required.

In one preferred form of the invention, filter 915 is disposed in between plate 905 and the outside of a side panel of sterilization cabinet 105 so as to allow filter 915 to be accessed from the outside of sterilization cabinet 105. In another preferred form of the invention, filter 915 is disposed intermediate plate 905 and the inside of a panel of sterilization cabinet 105 so as to allow filter 915 to be accessed from the inside of sterilization cabinet 105 for added filter protection. Filter ports 900 may also be provided with covers (not shown) to prevent damage during transportation.

Filter ports 900 and the components thereof are more consistent with the design of other rigid containers in the marketplace, thereby allowing for a crossover of intuitive training and also for a preferred manufacturing process.

FIGS. 46A-46F illustrates an improved method for maintaining and ensuring sterility of the chamber 110 of a sterilization container/cabinet 105. FIGS. 46A-46F illustrates a sterilization cabinet 105 that includes one or more vented areas or vents 430 in a panel of a wall 126, door 130, back panel or floor 125 of the cabinet. The illustrated cabinet 105 shows vents 430 in a door 130 and side walls 126 of the cabinet 105 for illustrative purposes only. Variations of the cabinet 105 can include one or more vents in any location of the cabinet's panels including the top or bottom of the cabinet 105. In addition, the vents 430, fitters 432, 434, retainer 436, and/or seal 440 can include circular shapes as illustrated or other non-circular configurations. The vents can include any fluid permeable configuration such that a sterilization agent can pass through during a sterilization cycle (including but not limited to a typical autoclave sterilization cycle). The sterilization cabinet 105 illustrated in these figures is shown without any shelving or components within the cabinet 105 for purposes of illustrating affixing the double filter to the container 105.

Figure 46A:
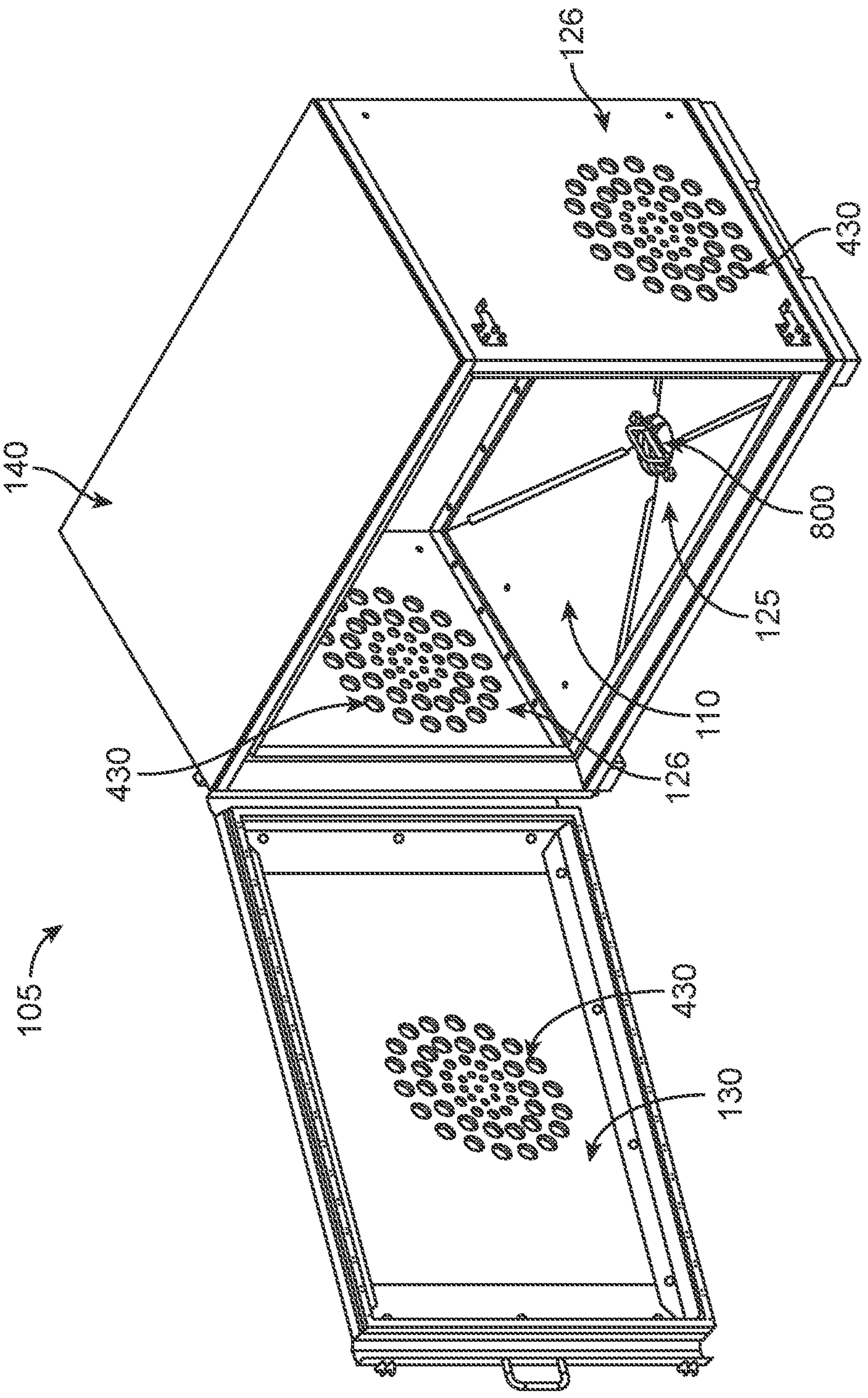
FIG. 46A-46F illustrates an improved method for maintaining and ensuring sterility of a chamber of a sterilization container/cabinet.
Figure 46B:
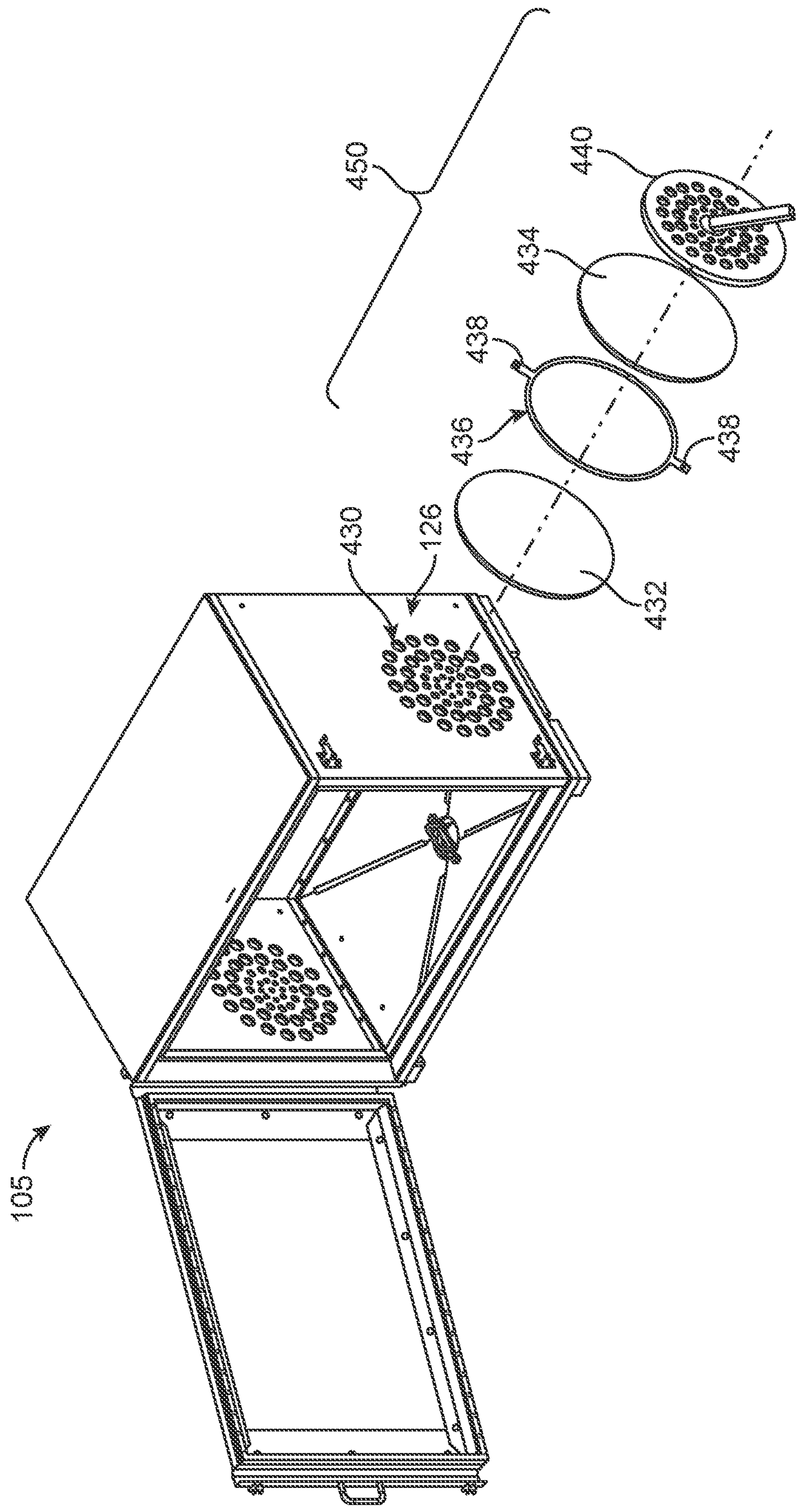

FIG. 46B illustrates an exploded view of a filter-seal assembly 450. As illustrated, the filter-seal assembly 450 includes a first filter 432, an engagement member, which in this example is shown as a retainer member/frame 436, a second filter 434 and a sealing member or filter cover 440. The filters 432, 434 can include any fluidly permeable filter material commonly used for filtration systems, especially those used for sterilization systems.

Figure 46C:
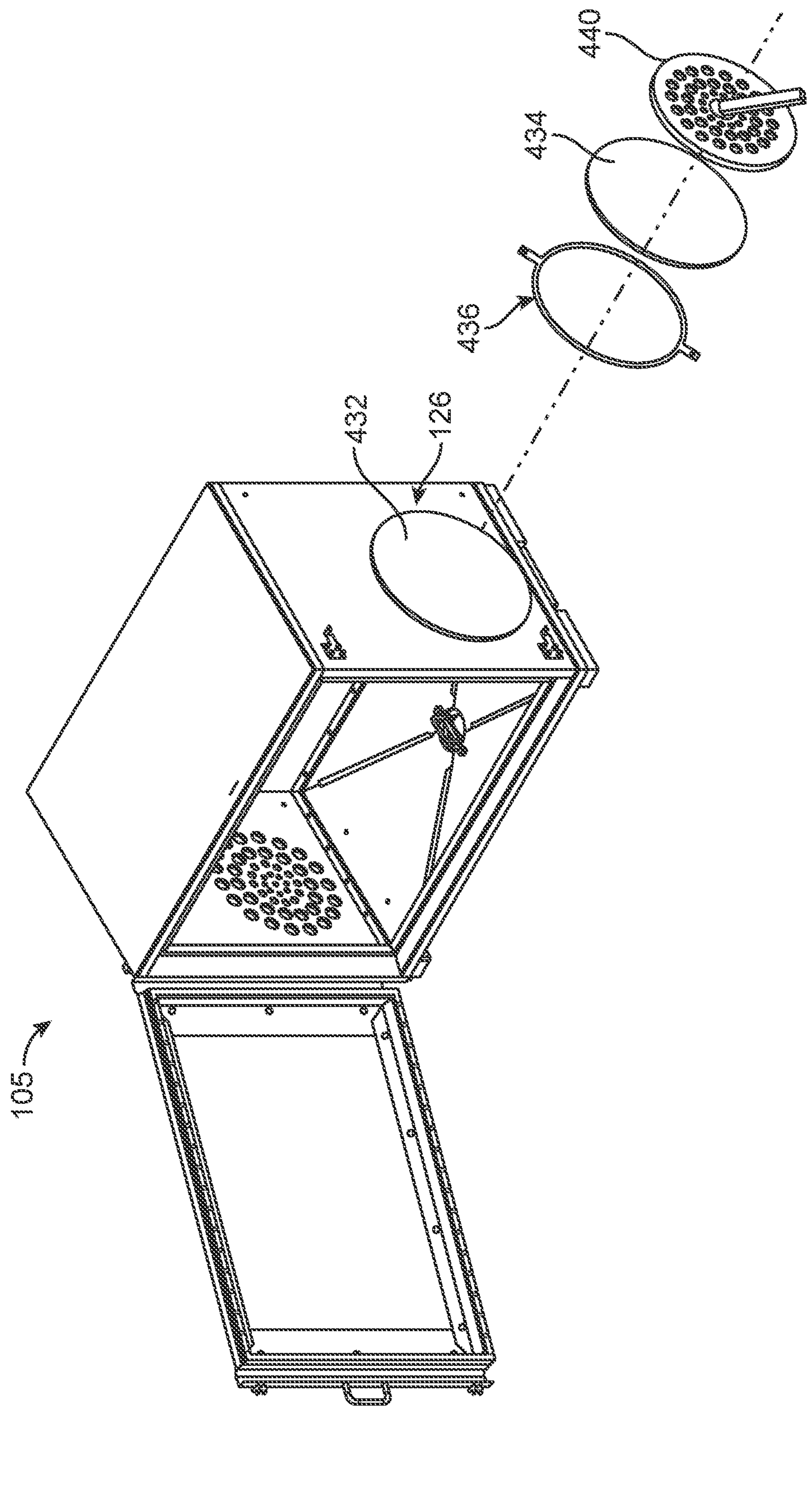
Figure 46D:
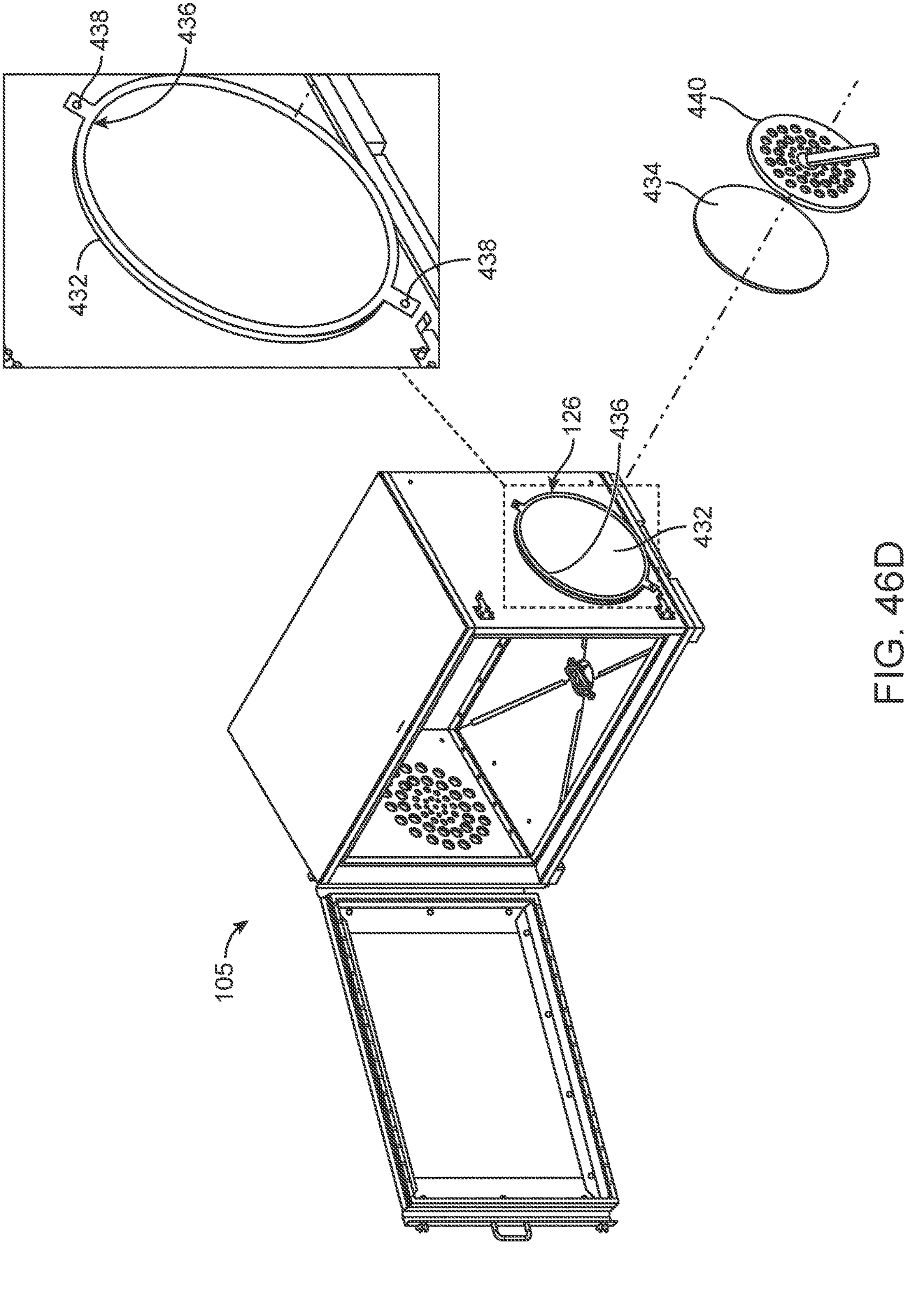

FIG. 46C shows placement of the first filter 432 against a side wall panel 126 of the unit 105. The first filter 432 encircles or spans beyond the vent area 432 so that fluid entering or exiting the adjacent vent 430 must also pass through the filter 432. FIG. 46D illustrates engaging the first filter 432 to the side panel 126. In the illustrated variation, the filter 432 is engaged to the side panel 126 using a retainer member/frame 436. The retainer member/frame 436 can be secured to the container 105/side panel 126 using standard attachment methods. For example, the panel can include one or more protrusions/threaded rods (not illustrated) that extend outward allowing openings 438 in the retainer member/frame 436 to be positioned over the protrusion such that the retainer member/frame 436 removably engages the first filter 432 to the container 105.

Figure 46E:
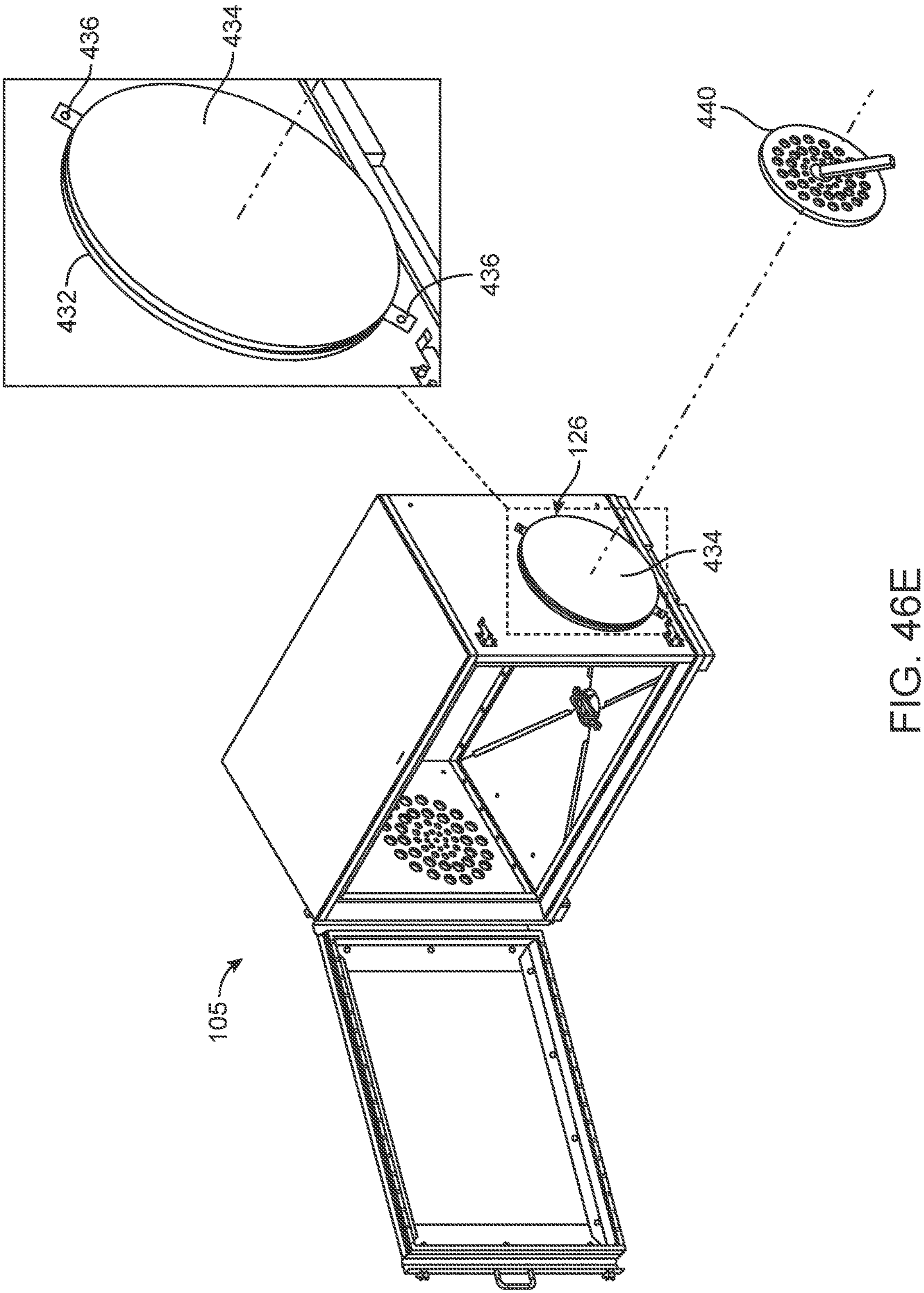

As discussed below, engaging of the first filter 432 to the container 105 is desired for checking the integrity of a seal formed by the filter-seal assembly 450 after the container 105 is processed through a sterilization cycle. The first filter 432 must remain engaged against the container 105 upon disassembly of the seal member 440 and the second filter 434. This construction/feature prevents potential contaminants from entering the container during the unloading process of the instrument tray. Any conventional means can be used to retain first filter 432 against the container 105. For example, the container 105 can include a retainer member coupled thereto by a hinge assembly (not shown). Alternatively, or in combination, the container 105 can include one or more clamping structures that releasably engages the first filter 432 against the cabinet wall 126. In certain variations, the retainer member/frame 436 extends beyond (or encircles) a perimeter of the vent 430 but remains engaged against the container 105 to sandwich the first filter 432 against the container 105. Next, as shown in FIG. 46E, the second filter 434 is positioned over the retainer member/frame 436. In the illustrated example, the perimeter of the second filter 434 is equal in to a perimeter of the first filter 432, but the second filter can extend beyond the first filter 432 or can be sized smaller than the first filter 432 as long as it engages the outward side of the retainer member/frame 436.

Figure 46F:
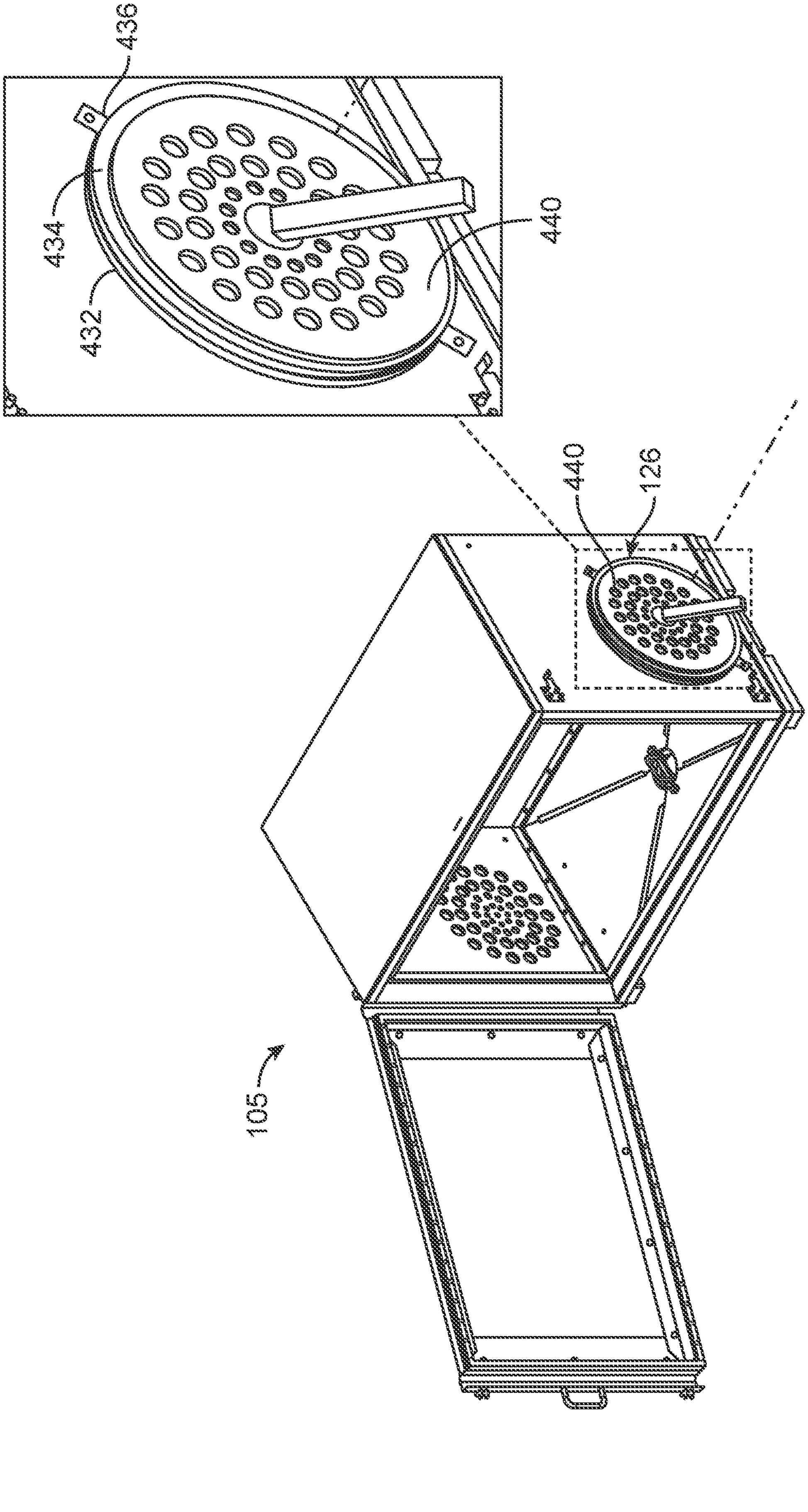

FIG. 46F illustrates securing of a filter cover 440 onto the second filter 434. The filter cover is designed to cause a seal against the sterilization container 105 such that any fluids entering or exiting the container 105 must pass through the porous/permeable region of the filter cover 440. In certain variations, securing the filter cover 440 causes an edge of the filter cover 440 to engage the second filter 434 directly against the first filter 432 and the first filter 434 against the panel 126 (or against the container 105) such that the edge of the filter cover 440 forms a seal simultaneously with both the first filter 432 and the second filter 434 against the sterilization unit 105. Alternatively, the seal can form sequentially.

In the variations illustrated in FIGS. 46A to 46F, the engagement of the first filter against the sterilization container 105 does not form a seal. Instead, it only causes retention of the filter 432 against the unit 105. The only seal formed about an individual vent is formed by the filter cover 440 as described above. The purpose of retaining the first filter against the unit is to prevent the passage of airborn contaminants from entering the container during the process of unloading the contents of the container. The remaining first filter essentially acts as a dust cover. The retention of the first filter against the unit may be accomplished by a ring or a frame of any kind, with or without a gasket forming a complete seal. The primary purpose of this dust cover is to allow thorough inspection of the integrity of the outermost filter and visual confirmation of the presence and integrity of the innermost filter, enabling the technician to have a high level of confidence that the contents are sterile. This prevents the need to set up a secondary back table until confirmation of the filter integrity can be made. The technician is able to unload the contents of the container directly to the surgical back table, eliminating a step in the process of the OR set up. There is a reasonable inference that can be made that if the outermost filter is not compromised, it is extremely unlikely that the innermost filter is compromised. The innermost filter can then be examined more closely after the contents of the container have been aseptically transferred to the back table.

Although the various illustrations show the container 105 in an open configuration, the container can be sealed with medical devices therein either before or after application of the filter seal assemblies. Once the container is secured (e.g., the door is closed and seals are formed at each filter) the container 105 is subject to one or more a sterilization cycles that sterilizes an internal region of the sterilization unit.

Once the sterilization cycle ends, the container 105 is removed from the autoclave or other sterilization apparatus. The sterilization container 105 can then be transferred to a storage area or a surgical area. Prior to opening the sterilization container 105 in a sterile area, a medical technician will check to ensure that the integrity of the filters is not compromised. The technician will then loosen the filter cover from the sterilization unit to disengage the seal of the edge from the second filter 434 (see FIG. 46E). The second filter is then detached from both the first filter and the sterilization unit (as shown in FIG. 46D), where the first filter remains engaged to the panel (in this case through the use of the retainer member/frame 436). The technician can then examine the second filter to assess it for integrity without removing the first filter from the sterilization unit. This integrity check of the second filter 434 allows confirmation that the integrity of the first filter 432 is not compromised. Because the sterilization cycle typically uses steam, high pressure and elevated temperatures, the filters 432, 434 have a tendency to stick together. The use of the double filter system described herein, which allows the first filter to remain engaged with the container 105, allows confirmation of the seal integrity without removing the filter 432 from the container 105.

Every minute of setup time in the OR is extremely costly to the facility. Steps removed from the OR setup process are valuable not only financially but also add to patient safety. Delays in room setup caused by compromised sterility of instruments are far too common. This method of thoroughly examining the outermost filter(s) first while leaving a dust cover for added protection against contaminants, then removing the contents of the container directly to the surgical back table, followed by examination of the innermost filter(s) for final confirmation that the contents remained sterile, allows for greater assurance of sterility of the instruments and a higher probability of performing best practice standards.

Immediate Use Sterilization (IUS)

The sterilization cabinets described herein are also especially suited for immediate use sterilization using steam or any other sterilizing agent that is passed into the sterilization cabinet to sterilize the medical items (including but not limited to surgical instruments, trays, implants, etc.). The sterilization agent is then evacuated from the cabinet while allowing the cabinet to remain sealed to prevent any contaminants from entering the sterilization chamber within the cabinet after the sterilization process.

Immediate use is generally defined as the shortest possible time between a sterilized item's removal from the sterilizer and its aseptic transfer to the sterile field. Immediacy implies that a sterilized item is used during the procedure for which it was sterilized and in a manner that minimizes its exposure to air and other environmental contaminants. A sterilized item intended for immediate use is not stored for future use or held from one case to another. Immediacy, rather than being defined according to a specific time frame, is established through the critical analysis and expert collaboration of the healthcare team. IUS has replaced the term "flash sterilization" which was used to describe steam sterilization cycles where unwrapped medical instruments were subjected to an abbreviated steam exposure time and then used promptly after completion of the sterilization cycle completion and without being stored. Traditional "terminal sterilization" is a term used for the process of sterilizing a medical item within a container or wrapper, or other packaging to maintain the item's sterility and allow the devices to be stored for later use. Therefore, IUS generally describes a process that is generally limited to situations when a one-of-a-kind instrument that is intended for a surgical procedure is unintentionally rendered unsterile (e.g., dropped on the floor, touched by a non-sterile item/person, etc). IUS is also for when an item or an entire tray can be found to be unsterile and there are no sterile substitutions. IUS has also been used when an instrument is not delivered to the surgical theatre in a timely fashion, or when someone simply forgot to sterilize the item. Regardless, IUS is being used more frequently than intended.

The sterilization cabinets of the present disclosure offer a significant advantage for IUS. For example, if an entire sterile field is compromised, all the trays of instruments can be returned to a sterile processing area, quickly cleaned and then processed in the sterilization cabinets. In one example, the sterilization cabinet is processed in an autoclave on a 4 minute (or to the manufacturer's IFU) sterilization cycle with little or no dry time. The sterilization cabinets described herein can accommodate anywhere from a single item to any number of trays (while not exceeding the limits on each cabinet—typically by weight).

A typical PreVacuum Steam Sterilizer's terminal sterilization cycle for orthopedic instruments, in accordance with the manufacturer's IFU, is a 4 minute sterilization cycle followed by a 30 minute dry time. Some vendors have longer indicated cycles (5 or 10 minute sterilization followed by 40 or 45 minute dry time) based upon the complexity or size of their instrument sets. Steam sterilizers generally take an hour or longer per cycle. First there is a conditioning phase that takes 15-20 minutes, during which there are several purges as the autoclave gets up to the appropriate temperature (this can vary by weight and the temperature of the items placed within the autoclave chamber). Following the conditioning phase is the sterilization phase during which steam saturates the contents of the autoclave killing bacteria to render the contents sterile. Following the sterilization phase is the drying phase, during which a vacuum is pulled under pressure multiple times to draw the steam out of the chamber at reduced temperatures, turning steam into air and water as it is pulled away from the contents.

As noted above, the design of the sterilization cabinet (e.g., the number of vent ports covered by filters as well as the sloped/pitched floor) decreases the time needed to dry the contents of the cabinet because nearly all of the moisture or condensate is removed very quickly after pulling a single vacuum following the steam sterilization cycle. In variations, the cabinets were mostly dry after a minute of dry time and fully dry within 5 minutes. This feature allows the sterilization cabinets to be used for IUS since the medical items are sterilized even if condensation remains in the cabinet. The presence of the condensation means that the items cannot be stored. But because the cabinet includes filters to keep out contaminants, the medical items sterilized in an IUS cycle can be ready for immediate use. The design of the cabinets prevents moisture or condensation from leaking out of the cabinet during removal of medical items after an IUS cycle. Unlike other IUS containment devices, the design of the cabinets continues to be an effective microbial barrier against the ingress of any contaminants during the transportation from the sterilizer to the location designated for the surgical procedure.

Figure 47A:
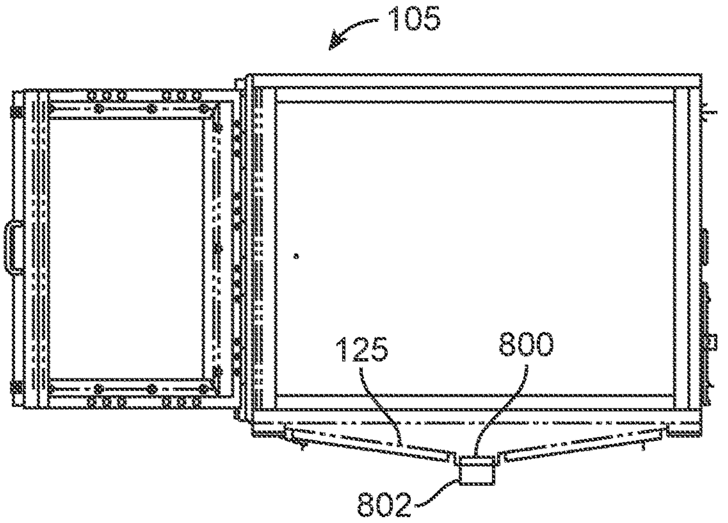
FIGS. 47A to 47C show features of sterilization cabinets that can be used for shortened sterilization cycle times and IUS.
Figure 47B:
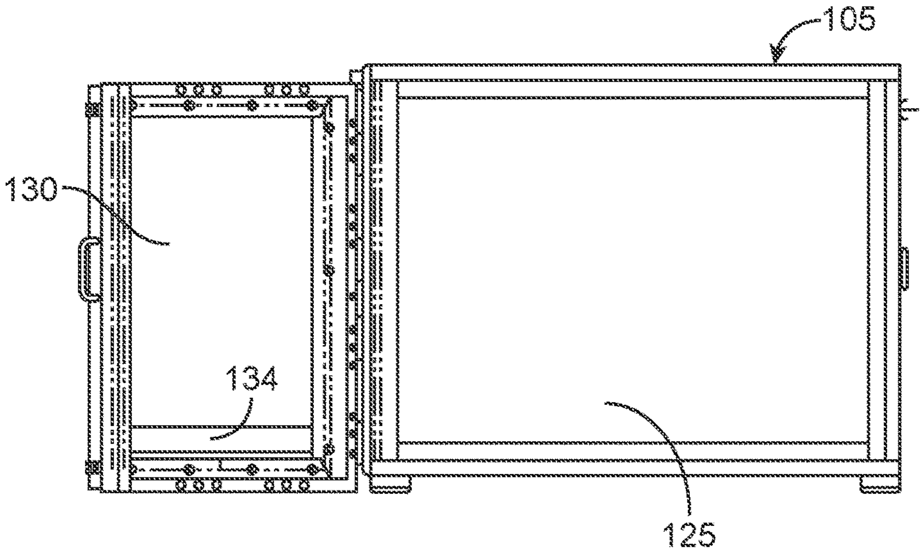
Figure 47C:
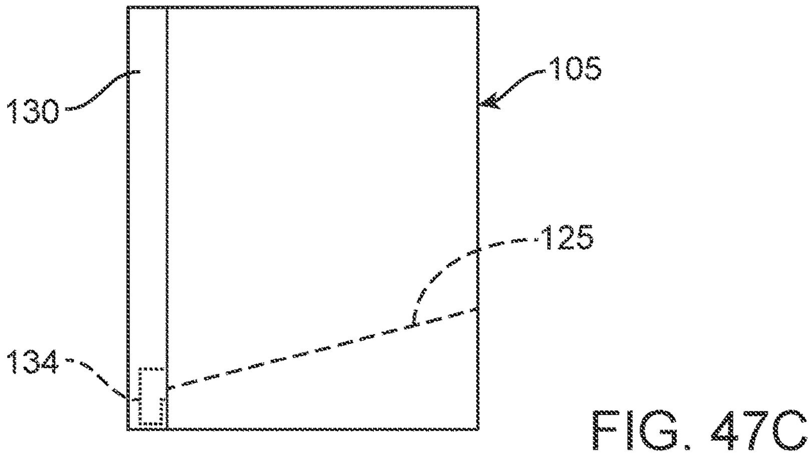

In addition to the sterilization cabinets/containers disclosed above, FIGS. 47A to 47C show features of sterilization cabinets 105 that can be used for shortened sterilization cycle times and IUS. FIG. 47A illustrates a cabinet 105 with a pitched floor 125 having a drain 800 with a condensate filter 802.

There is a need to prevent liquids from exiting the cabinet 105 if the cabinet is used in a IUS procedure since it will be undesirable to have liquid dropping or escaping from the cabinet during transportation of the cabinet from the sterilization area. In the event that condensation remains in the cabinet after a sterilization cycle, the condensate or liquid is prevented from exiting the drain 800 due to the presence of the condensate filter 802. The condensate filter may be a hydrophobic material that will not allow the passage of water from one side to the other. The condensate filter 802 can comprise a removable plug, a water trap (e.g., it absorbs water but does not release the water). Alternatively, the condensate filter 802 can comprise a thermostatically-controlled plug or valve as discussed above. Such a valve opens under the high temperatures of a steam sterilization cycle and allows condensate and air to be pulled out during a vacuum cycle. Once the temperature drops, the thermostatically controlled condensate filter 802 closes to prevent further liquids from exiting. Such a valve may also open and close as a function of pressure, time and/or temperature or a combination of any or all three.

FIG. 47B illustrates a pitched floor 125 that directs condensate towards a front opening of the cabinet 105 towards a water trap 134. In this variation, the water trap 134 is located in a door 130 of the cabinet 105. Because the cabinet design 105 eliminates most condensation after the vacuum cycle, the remaining condensation can fit within the water trap 134. Alternatively, the water trap can be located within the cabinet 105 but below the floor 125 of the cabinet.

In another variation, the water trap can comprise a hydrophobic material or a material that absorbs liquids to prevent liquids from leaking when the door is opened.

Figure 48A:
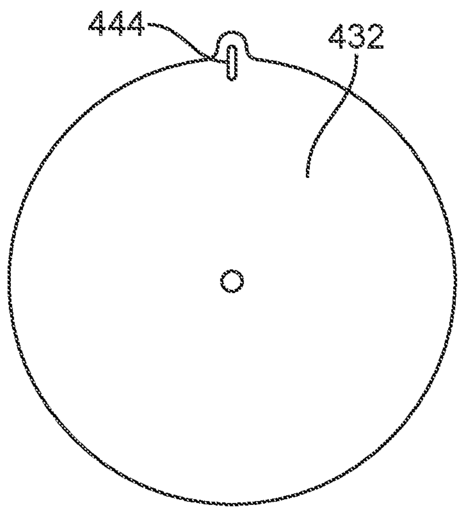
FIG. 48A-48D illustrates an improved filter for use with a double filter sterilization unit.
Figure 48B:
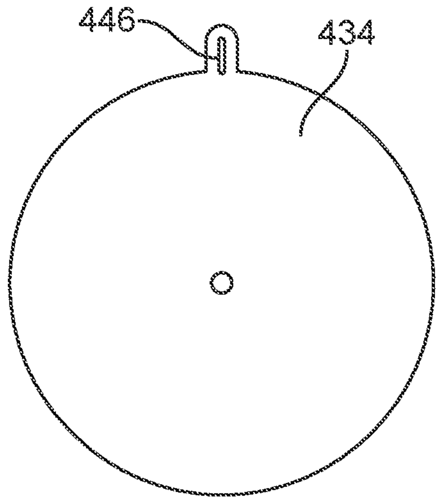
Figure 48C:
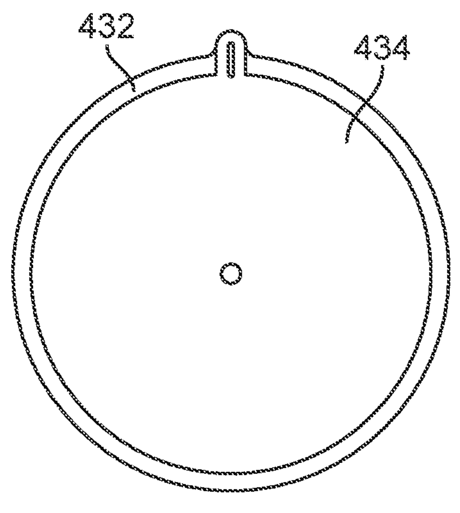
Figure 48D:
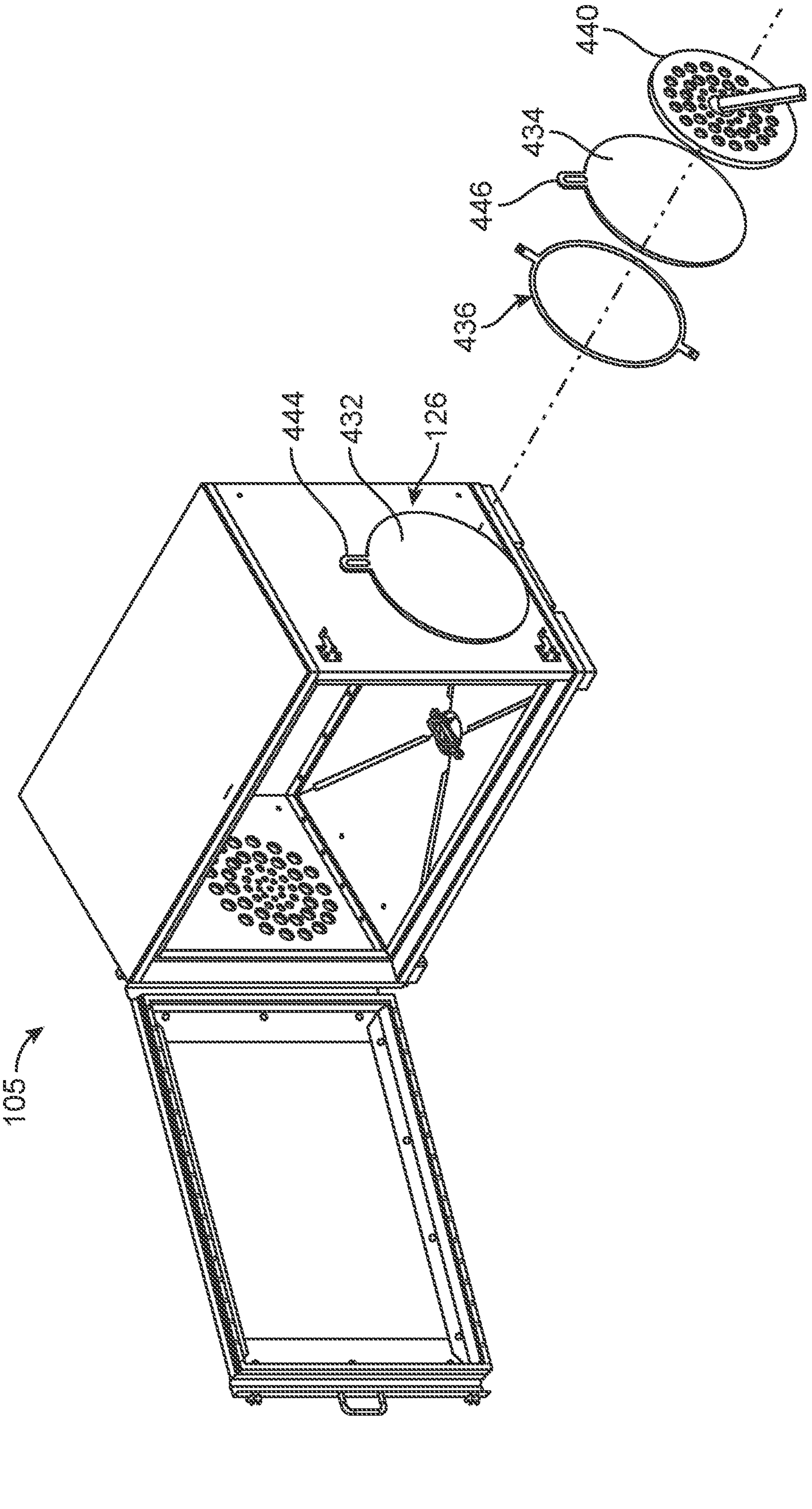

FIGS. 48A-48D illustrate another variation of a double filter configuration for use in a double filter system as described above. In this variation, a first filter 432, is positioned on a sterilization unit 126 by positioning a slit 444 or mounting opening onto a projection (not shown) extending from a wall of the unit 126. As shown, a second filter 434, which is smaller in diameter than the first filter 432, also includes an opening or slit 446. The filters 432 and 434 are mounted in the same manner as described above, but the slit 444 allows for the filter to be positioned by an operator such that the filter 432 does not need to be held against the unit as the ring 436 is affixed to the unit 126. Once the ring 436 is secured over filter 432, the second filter 434can be positioned over the first filter 432 and ring. Such a configuration is shown in FIG. 48C (the ring is omitted for purposes of illustration). Mounting of the second filter 434 can be accomplished by positioning the slit 446 over the same projection that held the first filter. Variations of the filters can include any number of slits/features that secure the filter to the unit to prepare for sealing of the filters. Once the second filter 434 is mounted, the final seal 440 can be positioned over the second filter 434 to form a seal against the unit 126, which sandwiches the filters 432 and 434 between the wall of the unit and the seal.

In another variation, any of the filters used in the system can comprise a PTFE (Polytetraflouroethylene) material. For example, the inner or outer filters described above, and or the drain filter can be fabricated from PTFE. PTFE is hydrophobic so water does not wet the filter but does allow for continued airflow. Wet filters are rejected by OR personnel as this is considered to create a pathway for bacteria; thus contents are considered unsterile. Water is able to pass through the PTFE filters when under pressure in the autoclave.

In another variation, any of the filters used in the system can comprise a PTFE (Polytetraflouroethylene) material. For example, the inner or outer filters described above, and or the drain filter can be fabricated from PTFE. PTFE is hydrophobic so water does not wet the filter but does allow for continued airflow. Wet filters are rejected by OR personnel as this is considered to create a pathway for bacteria, thus contents are considered unsterile. Water is able to pass through the PTFE filters when under pressure in the autoclave.

One variation of filter is fabricated from PTFE in a fine powder resin form, expanding it into a 3-D web-like structure creating billions of microscopic pores. This membrane may then be laminated onto another filter material. These pores can prevent particles larger than 0.2 microns (or 0.45, 1.0 depending on the structure) from passing through the filter. This microscopic barrier to microbes allows for air flow but, even in the event moisture is retained within the container, the barrier will not be compromised by becoming wet. Since PTFE has a high flow rate and broad chemical compatibility, the filter can be used with multiple sterilants (other than steam). In another variation, the filters can comprise oleophobic PTFE membranes as well. Such a filter repels oil as well as water.)

The PTFE filters can be single use or reusable. In the event these filters are reusable, the system may include an additional disposable microfiber filter element as a pre-filter to allow for extended life—less "clogging" of the reusable filter by high levels of solid particles.

In another variation, the filter can comprise a PES (polyethersulfone) membrane, either disposable or reusable, that allows for even higher throughput of sterilants (including steam). While PES is hydrophyllic and will become wet with water, it is likely that PES filters could allow for a faster drying time so sterilized contents would be completely dry before use.

Modifications

It should also be understood that many additional changes in the details, materials, steps and arrangements of parts, which have been herein described and illustrated in order to explain the nature of the present invention, may be made by those skilled in the art while still remaining within the principles and scope of the invention.

The invention claimed is:

1. A method of sterilizing medical instruments using immediate use sterilization, comprising:

positioning at least one medical instrument within an enclosed sterilization area of a sterilization cabinet, the sterilization cabinet includes a plurality of walls and a floor, an opening to permit access to the enclosed sterilization area, a door configured to close the sterilization cabinet by forming a seal that closes the opening, at least one vent in the sterilization cabinet, a filter covering the at least one vent on an exterior of the sterilization cabinet, where the sterilization cabinet includes a drain in the floor having a porous hydrophobic condensate filter in fluid communication with the drain;

closing the door on the sterilization cabinet to seal the enclosed sterilization area;

positioning the sterilization cabinet in an autoclave;

initiating a sterilization cycle to sterilize the at least one medical instrument within the sterilization cabinet by subjecting the sterilization cabinet to at least one steam application within the autoclave;

initiating a drying cycle, the drying cycle comprising drawing a vacuum within the enclosed sterilization area to pull condensate away from the at least one medical instrument wherein any condensate remaining within the enclosed sterilization area is driven by gravity to a region of the sterilization cabinet that prevents flowing of the condensate out of the opening when the door is opened, wherein the drying cycle lasts about 5 minutes or less; and;

after removing the sterilization cabinet from the autoclave, immediately relocating the sterilization cabinet from the autoclave to a staging area such that the at least one medical instrument (i) is available for immediate use and (ii) has been sterilized to remain stored within the enclosed sterilization area for future use, wherein the condensate filter prevents any microbes from entering the enclosed sterilization area.

2. The method of claim 1, further comprising positioning at least one tamper evident lock on the door after closing the door.

3. The method of claim 1, wherein relocating the sterilization cabinet from the autoclave to the staging area occurs prior to finishing a drying cycle of the autoclave.

4. The method of claim 1, wherein the floor is angled towards the door and the door comprises a fluid trap to collect any condensate which prevents flowing of the condensate out of the opening when the door is opened.

5. The method of claim 1, wherein relocating the sterilization cabinet from the autoclave occurs after initiating a shortened dry cycle of the autoclave by drawing the vacuum within the sterilization cabinet a single time.

6. The method of claim 1, wherein the floor is angled to collect the condensate away from the opening such that to prevent flowing of the condensate out of the opening when the door is opened.

7. The method of claim 1, wherein a floor of the sterilization cabinet is pitched causing any condensate remaining within the enclosed sterilization area to be driven by gravity to a lowest portion the floor.

8. The method of claim 7, wherein the floor is pitched toward the drain such that condensate is directed by gravity towards the drain.

9. The method of claim 1, wherein the porous hydrophobic condensate filter is positioned on an exterior of the sterilization cabinet.

10. The method of claim 1, wherein the sterilization cycle lasts for a duration of around 3 minutes.

11. The method of claim 1, wherein the sterilization cycle lasts for a duration of around 4 minutes.

12. A method of sterilizing a medical item using immediate use steam sterilization, comprising:

providing a sterilization cabinet having a chamber with a plurality of walls surrounding the chamber, where the plurality of walls form an opening for placement of the medical item within the chamber, the sterilization cabinet is configured to use gravity to direct a condensate that is generated during a sterilization process along a floor of the sterilization cabinet to a lowest point in the sterilization cabinet comprising a drain, where the drain is in fluid communication with a porous hydrophobic condensate filter;

closing a door to the sterilization cabinet when the medical item is within the chamber to seal the chamber;

positioning the sterilization cabinet within a sterilization unit;

initiating the sterilization unit to perform a sterilization cycle;

initiating a drying cycle, the drying cycle comprising applying a single vacuum cycle to the sterilization cabinet to pull air and the condensate out of the sterilization cabinet such that condensate remains in the chamber;

removing the sterilization cabinet from the sterilization unit; and after removing the sterilization cabinet from the sterilization unit, immediately delivering the medical item to a surgical area for immediate use without storing the medical item, wherein the condensate filter prevents any microbes from entering the sterilization cabinet, and wherein the medical item remains sterile in the sterilization cabinet to be available for immediate use and has been sterilized to remain in the sterilization cabinet to be stored for future use.

13. The method of claim 12, further comprising removing the medical item from the sterilization cabinet while condensate remains in the sterilization cabinet.

14. The method of claim 12, to wherein applying the single vacuum cycle to the sterilization cabinet to pull air and condensate out of the sterilization cabinet causes condensate to accumulate in a region that prevents flowing of the condensate out of the opening when the door is opened.

15. The method of claim 12, wherein the sterilization unit comprises an autoclave.

16. The method of claim 12, further comprising positioning at least one tamper evident lock on the door after closing the door.

17. The method of claim 12, wherein relocating the sterilization cabinet from the sterilization unit to the staging area occurs prior to completion of a drying cycle of the sterilization unit.

18. The method of claim 12, wherein the floor is angled to collect the condensate away from the opening such that to prevent flowing of the condensate out of the opening when the door is opened.

19. The method of claim 12, wherein a floor of the sterilization cabinet is pitched causing any condensate remaining within the chamber when to be driven by gravity to a lowest portion the floor.

20. The method of claim 12, wherein the floor is pitched toward the drain such that condensate is directed by gravity towards the drain, and wherein the drain is covered by a filter.

21. The method of claim 12, wherein the condensate filter is positioned on an exterior of the sterilization cabinet.

22. The method of claim 12, wherein the drying cycle lasts for a duration of about 5 minutes or less.

23. The method of claim 12, wherein the sterilization cycle lasts for a duration of around 3 minutes.

24. The method of claim 12, wherein the sterilization cycle lasts for a duration of around 4 minutes.

* * * * *